(12) United States Patent
Nishimura et al.

(10) Patent No.: US 6,713,472 B1
(45) Date of Patent: Mar. 30, 2004

(54) THIAZINE OR PYRAZINE DERIVATIVES

(75) Inventors: Kazuo Nishimura, Osaka (JP); Masakazu Ban, Osaka (JP); Ken-ichi Fujimura, Osaka (JP); Naoyuki Kobayashi, Osaka (JP); Masanori Hori, Osaka (JP); Eiko Matsumoto, Ashiya (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 4 days.

(21) Appl. No.: 10/031,540

(22) PCT Filed: Jul. 26, 2000

(86) PCT No.: PCT/JP00/04964

§ 371 (c)(1),
(2), (4) Date: Jan. 18, 2002

(87) PCT Pub. No.: WO01/07419

PCT Pub. Date: Feb. 1, 2001

(30) Foreign Application Priority Data

Jul. 26, 1999 (JP) ............................................ 11-210907

(51) Int. Cl.[7] .................. C07D 241/08; C07D 401/12; C07D 401/14; A61K 31/496; A61P 9/04
(52) U.S. Cl. .................. 514/211.15; 544/60; 544/120; 544/355; 544/295; 544/405; 544/408; 514/227.8; 514/235.8; 514/252.11; 514/255.05; 514/252.1; 514/218; 514/217.05; 540/544; 540/575; 540/598
(58) Field of Search .......................... 544/60, 120, 355, 544/295, 405, 408; 514/227.8, 235.8, 252.11, 255.05, 252.1, 218, 211.15, 217.05; 540/544, 575, 598

(56) References Cited

U.S. PATENT DOCUMENTS 5,908,843 A  6/1999 Gante et al. ................. 514/255

6,211,183 B1  4/2001 Marlowe et al. ........ 514/255.02

FOREIGN PATENT DOCUMENTS

| EP | 0 608 759 A | 8/1994 |
| EP | 0 643 072 A | 3/1995 |
| EP | 0 666 261 A | 8/1995 |
| JP | 58-35176 A | 3/1983 |
| JP | 2-275869 A | 11/1990 |
| WO | WO 98/46591 A | 10/1998 |

OTHER PUBLICATIONS (Takai S, Jin D, and Miyazaki M., Abstarct of Nippon Yakurigaku Zasshi, Oct. 1999; 114 Suppl 1:41p–47P.*

* cited by examiner

Primary Examiner—Mark L Berch
Assistant Examiner—Kahsay Habte
(74) Attorney, Agent, or Firm—Frishauf, Holtz, Goodman & Chick, P.C.

(57) ABSTRACT

A compound which is a chymase inhibitor and which is represented by a formula [I] and salts thereof. In the formula [I], X is $R^6-(A_2)_n-N$, $R^1$ and $R^2$ are H, alkyl, cycloalkyl or aryl, $R^3$ and $R^4$ are H, alkyl, cycloalkyl, aryl or aromatic heterocycle, $R^5$ is H, alkyl, cycloalkyl, aryl or $-A_3-A_4-R^7$, $R^6$ is H, alkyl, cycloalkyl, OH, alkoxy, aryl, aryloxy or an aromatic heterocycle, $R^7$ is H, alkyl, OH, alkoxy, aryl, aryloxy, amino, alkylamino, arylamino, an aromatic heterocycle or a nonaromatic heterocycle, $A_1$ is alkylene, $A_2$ is carbonyl or sulfonyl, $A_3$ is alkylene, $A_4$ is carbonyl or oxalyl and n is o or 1. The formula [I] is

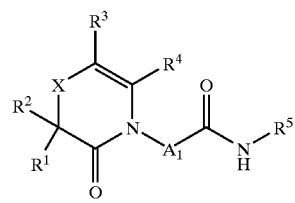

[I]

16 Claims, No Drawings

THIAZINE OR PYRAZINE DERIVATIVES

TECHNICAL FIELD

The present invention relates to novel 3-oxo-3,4-dihydro-2H-1,4-thiazine derivatives or 2-oxo-1,2,3,4-tetrahydropyrazine derivatives being useful as pharmaceuticals.

BACKGROUND ART

Compounds having 3-oxo-3,4-dihydro-2H-1,4-thiazine or 2-oxo-1,2,3,4-tetrahydropyrazine as a main skeleton, which are compounds having one double bond in their ring, have scarcely been studied. There were only reports concerning a study of introducing a phenyl group into the 5th-position of 3-oxo-3,4-dihydro-2H-1,4-thiazine derivatives (Japanese Laid-open Patent Publication No. 275869/1990), a study of synthesis of 2-oxo-1,2,3,4-tetrahydropyrazine derivatives as synthetic intermediates of 1,5-imino-3-benzoazocine derivatives aiming at analgesics or antitussives (Japanese Laid-open Patent Publication No. 35176/1983) and the like.

Much less, there has been no report relating to a study wherein various substituents are introduced into a nitrogen atom at the 4th-position of the 3-oxo-3,4-dihydro-2H-1,4-thiazine derivatives or into a nitrogen atom at the 1st-position of the 2-oxo-1,2,3,4-tetrahydropyrazine derivatives and their pharmaceutical utility is examined. In particular, compounds having carboxy-lower alkylene converted into amide, which are subjects of the present invention, have not been studied at all.

It is a very interesting subject to synthesize novel compounds having 3-oxo-3,4-dihydro-2H-1,4-thiazine or 2-oxo-1,2,3,4-tetrahydropyrazine as a main skeleton wherein various substituents are introduced into the nitrogen atom in their ring and to study their pharmaceutical utility.

DISCLOSURE OF THE INVENTION

The present inventors studied preparation of various novel compounds having 3-oxo-3,4-dihydro-2H-1,4-thiazine or 2-oxo-1,2,3,4-tetrahydropyrazine as a main skeleton. Targets of the study are 1) to prepare novel compounds wherein carboxy-lower alkylene converted into amide is introduced into a nitrogen atom at the 4th-position of 3-oxo-3,4-dihydro-2H-1,4-thiazine derivatives or into a nitrogen atom at the 1st-position of 2-oxo-1,2,3,4-tetrahydropyrazine derivatives, and 2) to prepare novel compounds wherein various substituents are introduced into a nitrogen atom at the 4th-position of the 2-oxo-1,2,3,4-tetrahydropyrazine derivatives. As a result, the present inventors succeeded in preparing many novel compounds as mentioned later. Studying their pharmacological actions, these novel compounds were found to exhibit chymase inhibitory effects and to be useful as pharmaceuticals. The present inventors succeeded also in preparing novel compounds which are useful as synthetic intermediates in a process of the preparation of the above-mentioned 3-oxo-3,4-dihydro-2H-1,4-thiazine derivatives or 2-oxo-1,2,3,4-tetrahydropyrazine derivatives.

The present invention relates to compounds represented by the following general formula [I] and salts thereof (hereinafter referred to as "the present compound" as far as there is no proviso), pharmaceutical compositions comprising them as active ingredients, and compounds represented by the general formula [II] being useful as synthetic intermediates of the present compound and salts of the intermediates (hereinafter referred to as "the present synthetic intermediate" as far as there is no proviso),

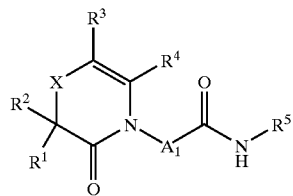

wherein

X is S or $R^6$—$(A_2)_n$—N, $R^1$ and $R^2$, being the same or different, are hydrogen, lower alkyl, cycloalkyl or aryl, $R^3$ and $R^4$, being the same or different, are hydrogen, lower alkyl, cycloalkyl, aryl or aromatic heterocycles, $R^5$ is hydrogen, lower alkyl, cycloalkyl, aryl or —$A_3$—$A_4$—$R^7$, $R^6$ is hydrogen, lower alkyl, cycloalkyl, hydroxy, lower alkoxy, aryl, aryloxy or an aromatic heterocycle, $R^7$ is hydrogen, lower alkyl, hydroxy, lower alkoxy, aryl, aryloxy, amino, lower alkylamino, arylamino, an aromatic heterocycle or a nonaromatic heterocycle, n is 0 or 1, $A_1$ is lower alkylene, $A_2$ is carbonyl or sulfonyl, $A_3$ is lower alkylene, and $A_4$ is carbonyl or oxalyl.

Each lower alkyl defined above can be substituted by halogen, hydroxy, lower alkoxy, aryl or aryloxy.

Each lower alkoxy defined above can be substituted by aryl.

Each lower alkylene defined above can be substituted by aryl. The same definitions are applied hereinafter.

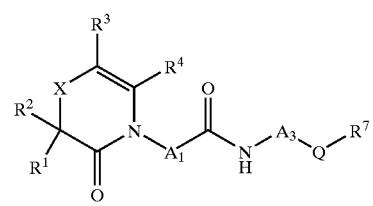

[wherein Q is —CH(OH)CO— or —CH(OH)—. The same definition is applied hereinafter.]

The groups defined above have the following meanings through the whole present specification.

The halogen is fluorine, chlorine, bromine or iodine.

The lower alkyl is straight-chain or branched alkyl having one to six carbon atoms such as methyl, ethyl, propyl, isopropyl, butyl, isobutyl, sec-butyl, tert-butyl, pentyl, isopentyl, hexyl or isohexyl. The lower alkyl can be substituted by halogen, cycloalkyl, hydroxy, lower alkoxy, aryl or aryloxy.

The cycloalkyl is cycloalkyl having three to eight carbon atoms such as cyclopropyl, cyclobutyl, cyclopentyl, cyclohexyl, cycloheptyl or cyclooctyl. The cycloalkyl can be substituted by halogen, lower alkyl, cycloalkyl, hydroxy, lower alkoxy, aryl or aryloxy.

The lower alkoxy is straight-chain or branched alkoxy having one to six carbon atoms such as methoxy, ethoxy, propoxy, isopropoxy, t-butoxy or hexyloxy. The lower alkoxy can be substituted by halogen, cycloalkyl, hydroxy, lower alkoxy, aryl or aryloxy.

The lower alkylene is straight-chain or branched alkylene having one to six carbon atoms such as methylene, ethylene, trimethylene, tetramethylene, pentamethylene, hexamethylene, methylmethylene, dimethylmethylene, ethylmethylene, propylmethylene, isopropylmethylene, butylmethylene, isobutylmethylene, sec-butylmethylene, tert-butylmethylene, tert-butylethylene, dimethylethylene, ethylethylene, propylethylene, isopropylethylene, methyltrimethylene or propylene. The lower alkylene can be substituted by halogen, cycloalkyl, hydroxy, lower alkoxy, aryl or aryloxy.

The aryl is a monocyclic or condensed aromatic hydrocarbon such as phenyl or naphthyl. The aryl can be substituted by halogen, lower alkyl, cycloalkyl, hydroxy, lower alkoxy, aryl, aryloxy, acyl or nitro.

The aromatic heterocycle is an aromatic heterocycle having one heteroatom in the ring such as pyrrole, furan, thiophene or pyridine; an azole aromatic heterocycle such as imidazole, oxazole, thiazole, pyrazole, isoxazole or isothiazole; an aromatic heterocycle having two nitrogen atoms in the ring such as pyrazine or pyrimidine; or a condensed aromatic heterocycle such as indole, isoindole, benzimidazole, benzoxazole, benzothiazole or quinoline. Each aromatic heterocycle can be substituted by halogen, lower alkyl, cycloalkyl, hydroxy, lower alkoxy, aryl, aryloxy or acyl.

The nonaromatic heterocycle is a saturated nonaromatic heterocycle having one heteroatom in the ring such as pyrrolidine, tetrahydrofuran, tetrahydrothiophene, piperidine, tetrahydropyran or homopiperazine; a saturated nonaromatic heterocycle having two heteroatoms in the ring such as imidazolidine, oxazolidine, thiazolidine, pyrazolidine, piperazine, morpholine, thiomorpholine, homopiperidine or homomorpholine; an unsaturated nonaromatic heterocycle having one heteroatom in the ring such as pyrroline, dihydrofuran, dihydrothiophene, tetrahydropiperidine, dihydropiperidine, dihydropyran or pyran; or an unsaturated nonaromatic heterocycle having two heteroatoms such as imidazoline, oxazoline, thiazoline or pyrazoline. Each nonaromatic heterocycle can be substituted by halogen, lower alkyl, cycloalkyl, hydroxy, lower alkoxy, aryl, aryloxy or carbamoyl.

The acyl is lower alkanoyl having two to six carbon atoms such as acetyl, propionyl, butyryl, pivaloyl or pentanecarbonyl, or benzoyl. The phenyl ring of the benzoyl can be substituted by halogen, lower alkyl, cycloalkyl, hydroxy, lower alkoxy, aryl, aryloxy, acyl or nitro.

When the present compound or the present synthetic intermediate has free hydroxy or free amino, —NHR (wherein R is lower alkyl) or imino, they can be protected with a general protecting group.

General protecting groups of hydroxy can be used as the protecting group of hydroxy. Specific examples of the protecting group are acyl such as formyl, lower alkanoyl, halogeno-lower alkanoyl or benzoyl; alkoxycarbonyl such as lower alkoxycarbonyl or phenyl-lower alkoxycarbonyl; substituted alkyl derivatives such as allyl, lower alkoxy-lower alkyl, substituted lower alkoxy-lower alkyl, phenyl-lower alkyl, tetrahydropyranyl and tetrahydrofuranyl; and substituted silyl such as lower alkylsilyl or phenylsilyl. Each phenyl ring of the above-mentioned benzoyl, phenyl-lower alkoxycarbonyl, phenyl-lower alkyl and phenylsilyl can be substituted by halogen, lower alkyl, lower alkoxy or nitro.

More specific examples of the protecting group of hydroxy are acyl such as formyl, acetyl, pivaloyl, monochloroacetyl, trichloroacetyl, trifluoroacetyl, benzoyl, methoxycarbonyl, ethoxycarbonyl, isobutoxycarbonyl, t-butoxycarbonyl or benzyloxycarbonyl; substituted alkyl derivatives such as allyl, methoxymethyl, 1-ethoxyethyl, 2-methoxyethoxymethyl, benzyloxymethyl, benzyl, 4-methoxybenzyl, trityl, 2-tetrahydropyranyl and 2-tetrahydrofuranyl; and substituted silyl such as trimethylsilyl, triethylsilyl, triisopropylsilyl, t-butyldimethylsilyl or t-butyldiphenylsilyl.

The protecting groups of amino or imino can be those which are widely used as protecting groups of amine. Specific examples of the protecting group are acyl such as formyl, lower alkanoyl, halogeno-lower alkanoyl, benzoyl, lower alkoxycarbonyl, substituted lower alkoxycarbonyl or phenoxycarbonyl; substituted alkyl derivatives such as allyl, phenyl-lower alkyl and benzoyl-lower alkyl; substituted sulfonyl such as lower alkylsulfonyl or phenylsulfonyl; and lower alkoxy. Each phenyl ring of the above-mentioned benzoyl, phenoxycarbonyl, phenyl-lower alkyl, benzoyl-lower alkyl and phenylsulfonyl can be substituted by halogen, lower alkyl, lower alkoxy or nitro.

More specific examples of the protecting group of amino or imino are acyl such as formyl, acetyl, trichloroacetyl, trifluoroacetyl, benzoyl, methoxycarbonyl, ethoxycarbonyl, isobutoxycarbonyl, t-butoxycarbonyl, allyloxycarbonyl, 2,2,2-trichloroethoxycarbonyl, benzyloxycarbonyl, diphenylmethoxycarbonyl or phenoxycarbonyl; substituted alkyl derivatives such as allyl, benzyl and trityl; and substituted sulfonyl such as benzenesulfonyl, 2,4,6-trimethylbenzenesulfonyl or toluenesulfonyl.

Preferred examples of the present compound are compounds wherein the group(s) is (are) the followings in the compounds represented by the general formula [I] or salts thereof, (1a) X is a group selected from S and $R^6$—$(A_2)_n$—N; and/or (2a) $R^1$ and $R^2$, being the same or different, are groups selected from hydrogen, lower alkyl, cycloalkyl and aryl, wherein the lower alkyl can be substituted by a group selected from hydroxy and lower alkoxy; and/or (3a) $R^3$ and $R^4$, being the same or different, are groups or rings selected from hydrogen, lower alkyl, aryl and aromatic heterocycles, wherein the aryl can be substituted by a group selected from halogen, lower alkoxy and lower alkoxycarbonyl, and the lower alkoxy can be substituted by aryl; and/or (4a) $R^5$ is —$A_3$—$A_4$—$R^7$; and/or (5a) $R^6$ is a group or a ring selected from hydrogen, lower alkyl, cycloalkyl, lower alkoxy, aryl and aromatic heterocycles, wherein the lower alkyl can be substituted by a group selected from alkoxy, aryl and aryloxy, each lower alkoxy can be substituted by aryl, and each aryl can be substituted by a group selected from halogen, lower alkoxy and nitro; and/or (6a) $R^7$ is a group or a ring selected from hydrogen, lower alkyl, hydroxy, lower alkoxy, aryloxy, amino, lower alkylamino, aromatic heterocycles and nonaromatic heterocycles, wherein the cycloalkyl can be substituted by lower alkyl, the lower alkyl can be substituted by halogen or hydroxy, and the nonaromatic heterocycles can be substituted by lower alkyl, cycloalkyl or aminocarbonyl; and/or (7a) n is 1; and/or (8a) $A_1$ is lower alkylene, wherein the lower alkylene can be substituted by aryl; and/or (9a) $A_2$ is a group selected from carbonyl and sulfonyl; and/or (10a) $A_3$ is lower alkylene, wherein the lower alkylene can be substituted by aryl, and the aryl can be substituted by halogen; and/or (11a) $A_4$ is a group selected from carbonyl and oxalyl.
Namely,
Compounds defined by above (1a) in the compounds represented by the general formula [I] or salts thereof,
Compounds defined by above (2a) in the compounds represented by the general formula [I] or salts thereof,
Compounds defined by above (3a) in the compounds represented by the general formula [I] or salts thereof,
Compounds defined by above (4a) in the compounds represented by the general formula [I] or salts thereof,
Compounds defined by above (5a) in the compounds represented by the general formula [I] or salts thereof,
Compounds defined by above (6a) in the compounds represented by the general formula [I] or salts thereof,
Compounds defined by above (7a) in the compounds represented by the general formula [I] or salts thereof,
Compounds defined by above (8a) in the compounds represented by the general formula [I] or salts thereof,
Compounds defined by above (9a) in the compounds represented by the general formula [I] or salts thereof,
Compounds defined by above (10a) in the compounds represented by the general formula [I] or salts thereof,
Compounds defined by above (11a) in the compounds represented by the general formula [I] or salts thereof, and
Compounds defined by any combinations of two or more of above (1a), (2a), (3a), (4a), (5a), (6a), (7a), (8a), (9a), (10a) and (11a) in the compounds represented by the general formula [I] or salts thereof.

More preferred examples of the present compound are compounds wherein the group(s) is (are) the followings in the compounds represented by the general formula [I] or salts thereof;
(1a) X is a group selected from S and $R^6$—$(A_2)_n$—N; and/or
(2a) $R^1$ and $R^2$, being the same or different, are groups selected from hydrogen and lower alkyl; and/or
(3a) $R^3$ and $R^4$, being the same or different, are groups selected from hydrogen and aryl, wherein the aryl can be substituted by a group selected from halogen, lower alkoxy and lower alkoxycarbonyl, and the lower alkoxy can be substituted by aryl; and/or
(4a) $R^5$ is —$A_3$—$A_4$—$R^7$; and/or
(5a) $R^6$ is a group selected from lower alkyl, lower alkoxy, aryl and aromatic heterocycles, wherein the lower alkyl can be substituted by a group selected from lower alkoxy, aryl and aryloxy; and/or
(6a) $R^7$ is a group selected from lower alkyl, lower alkoxy, aromatic heterocycles and nonaromatic heterocycles, wherein the lower alkyl can be substituted by halogen, and the nonaromatic heterocycles can be substituted by lower alkyl; and/or
(7a) n is 1; and/or
(8a) $A_1$ is lower alkylene; and/or
(9a) $A_2$ is a group selected from carbonyl and sulfonyl; and/or
(10a) $A_3$ is lower alkylene, wherein the lower alkylene can be substituted by aryl; and/or
(11a) $A_4$ is a group selected from carbonyl and oxalyl.
Namely,
Compounds defined by above (1a) in the compounds represented by the general formula [I] or salts thereof,
Compounds defined by above (2a) in the compounds represented by the general formula [I] or salts thereof,
Compounds defined by above (3a) in the compounds represented by the general formula [I] or salts thereof,
Compounds defined by above (4a) in the compounds represented by the general formula [I] or salts thereof,
Compounds defined by above (5a) in the compounds represented by the general formula [I] or salts thereof,
Compounds defined by above (6a) in the compounds represented by the general formula [I] or salts thereof,
Compounds defined by above (7a) in the compounds represented by the general formula [I] or salts thereof,
Compounds defined by above (8a) in the compounds represented by the general formula [I] or salts thereof,
Compounds defined by above (9a) in the compounds represented by the general formula [I] or salts thereof,
Compounds defined by above (10a) in the compounds represented by the general formula [I] or salts thereof,
Compounds defined by above (11a) in the compounds represented by the general formula [I] or salts thereof, and
Compounds defined by any combinations of two or more of above (1a), (2a), (3a), (4a), (5a), (6a), (7a), (8a), (9a), (10a) and (11a) in the compounds represented by the general formula [I] or salts thereof.

Further preferred examples of the present compound are compounds wherein the group(s) is (are) the followings in the compounds represented by the general formula [I] or salts thereof
(1a) X is a group selected from S and $R^6$—$(A_2)_n$—N; and/or
(2a) $R^1$ and $R^2$, being the same or different, are groups selected from hydrogen and isopropyl; and/or
(3a) $R^3$ and $R^4$, being the same or different, are groups selected from hydrogen and phenyl; and/or
(4a) $R^5$ is —$A_3$—$A_4$—$R^7$; and/or
(5a) $R^6$ is a group or a ring selected from methyl, ethyl, isopropyl, t-butyl, methoxymethyl, phenyl, phenethyl, benzyloxy and pyridine; and/or
(6a) $R^7$ is a group or a ring selected from methyl, trifluoromethyl, heptafluoromethyl, methoxy, isopropyloxy, pyrrolidine, dihydrofuran, oxazoline, 4,4-dimethyloxazoline, thiazoline, 5,5-dimethylthiazoline, piperidine, piperazine, morpholine, oxazole, thiazole and benzothiazole; and/or
(7a) n is 1; and/or
(8a) $A_1$ is methylene; and/or
(9a) $A_2$ is a group selected from carbonyl and sulfonyl; and/or
(10a) $A_3$ is phenylmethylmethylene; and/or
(11a) $A_4$ is a group selected from carbonyl and oxalyl.
Namely,
Compounds defined by above (1a) in the compounds represented by the general formula [I] or salts thereof,
Compounds defined by above (2a) in the compounds represented by the general formula [I] or salts thereof,
Compounds defined by above (3a) in the compounds represented by the general formula [I] or salts thereof,
Compounds defined by above (4a) in the compounds represented by the general formula [I] or salts thereof,
Compounds defined by above (5a) in the compounds represented by the general formula [I] or salts thereof,
Compounds defined by above (6a) in the compounds represented by the general formula [I] or salts thereof,
Compounds defined by above (7a) in the compounds represented by the general formula [I] or salts thereof,
Compounds defined by above (8a) in the compounds represented by the general formula [I] or salts thereof,
Compounds defined by above (9a) in the compounds represented by the general formula [I] or salts thereof, Compounds defined by above (10a) in the compounds represented by the general formula [I] or salts thereof, Compounds defined by above (11a) in the compounds represented by the general formula [I] or salts thereof, and Compounds defined by any combinations of two or more of above (1a), (2a), (3a), (4a), (5a), (6a), (7a), (8a), (9a), (10a) and (11a) in the compounds represented by the general formula [I] or salts thereof.

The most preferred examples of the present compound are compounds wherein the group(s) is (are) the followings in the compounds represented by the general formula [I] or salts thereof, (1a) X is a group selected from S and $R^6$—$(A_2)_n$—N; and/or (2a) $R^1$ and $R^2$, being the same or different, are groups selected from hydrogen and isopropyl; and/or (3a) $R^3$ and $R^4$, being the same or different, are groups selected from hydrogen and phenyl; and/or (4a) $R^5$ is —$A_3$—$A_4$—$R^7$; and/or (5a) $R^6$ is a group or a ring selected from methyl, phenyl and pyridine; and/or (6a) $R^7$ is a group or a ring selected from trifluoromethyl, isopropyloxy, oxazoline, thiazoline, 4,4-dimethyloxazoline, 5,5-dimethylthiazoline and benzothiazole; and/or (7a) n is 1; and/or (8a) $A_1$ is methylene; and/or (9a) $A_2$ is carbonyl; and/or (10a) $A_3$ is phenylmethylmethylene; and/or (11a) $A_4$ is a group selected from carbonyl and oxalyl.

Namely,

Compounds defined by above (1a) in the compounds represented by the general formula [I] or salts thereof, Compounds defined by above (2a) in the compounds represented by the general formula [I] or salts thereof, Compounds defined by above (3a) in the compounds represented by the general formula [I] or salts thereof, Compounds defined by above (4a) in the compounds represented by the general formula [I] or salts thereof, Compounds defined by above (5a) in the compounds represented by the general formula [I] or salts thereof, Compounds defined by above (6a) in the compounds represented by the general formula [I] or salts thereof, Compounds defined by above (7a) in the compounds represented by the general formula [I] or salts thereof, Compounds defined by above (8a) in the compounds represented by the general formula [I] or salts thereof, Compounds defined by above (9a) in the compounds represented by the general formula [I] or salts thereof, Compounds defined by above (10a) in the compounds represented by the general formula [I] or salts thereof, Compounds defined by above (11a) in the compounds represented by the general formula [I] or salts thereof, and Compounds defined by any combinations of two or more of above (1a), (2a), (3a), (4a), (5a), (6a), (7a), (8a), (9a), (10a) and (11a) in the compounds represented by the general formula [I] or salts thereof.

The salts in the present invention refer to any pharmaceutically acceptable salts and are exemplified by salts with an inorganic acid such as hydrochloric acid, nitric acid or sulfuric acid, salts with an organic acid such as acetic acid, fumaric acid, maleic acid or tartaric acid, salts with an alkaline metal or an alkaline earth metal such as sodium, potassium or calcium, quaternary salts with an organohalogen compound, and the like.

Preferred examples of the quaternary salt are quaternary salts with an alkyl halide derivative. Specific examples of the quaternary salt are quaternary salts with methyl iodide, benzyl bromide, methyl bromoacetate, 2-bromoacetamide, 2-iodoacetamide, 4-bromo-2-methyl-2-butene, farnesyl bromide, geranyl bromide or the like.

Further, some of the present compounds or the present intermediates have asymmetric carbon atoms. When there are geometric isomers or optical isomers, these isomers are also included in the scope of the present invention. The present compounds or the present intermediates can take the form of solvates such as hydrates.

The present compounds represented by the general formula [I] can be synthesized, for example, by the following typical method or according to this method.

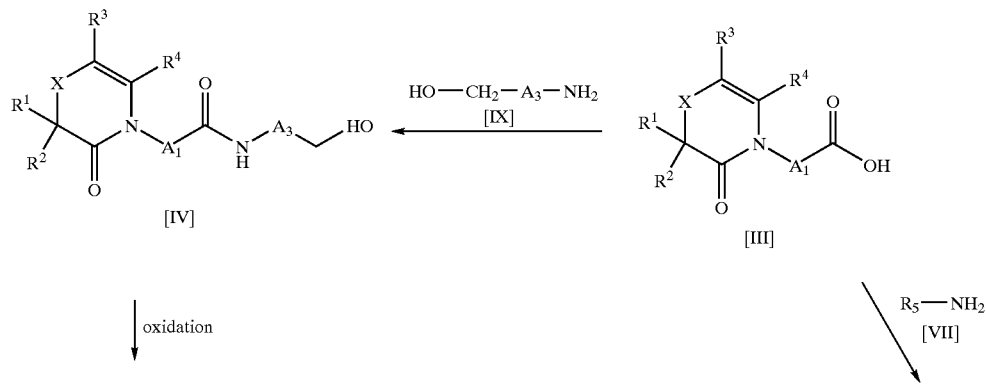

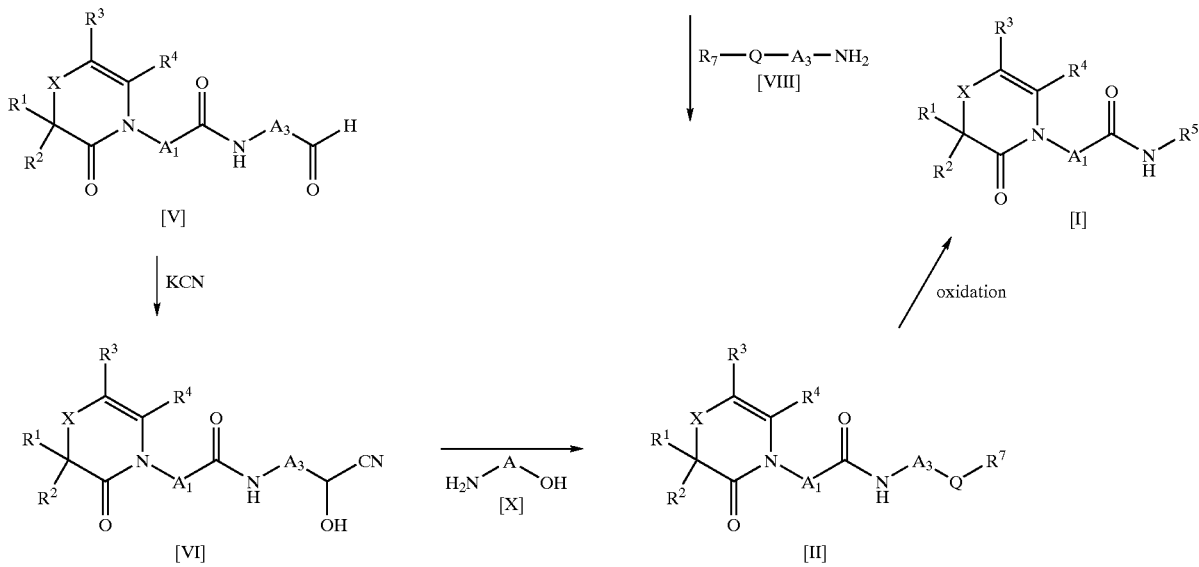

The above-mentioned method includes the following three synthetic routes.
Synthetic route A: compound [III]→compound [I]
Synthetic route B: compound [III]→compound [II] →compound [I]
Synthetic route C: compound [III]→compound [IV] →compound [V]→compound [VI]→compound [II] →compound [I]

These synthetic routes are specifically described hereinafter.

Synthetic Method A

The compound [III] and the amine derivative [VII] are condensed by a general method for formation of amide linkage to give the present compound [I]. Specific examples of the method are a method using a dehydrating condensing agent such as 1-(3-dimethylaminopropyl)-3-ethylcarbodiimide hydrochloride or 1,3-dicyclohexylcarbodiimide, and a method using mixed acid anhydride such as isobutyl chloroformate.

Synthetic Method B

The compound [III] and the amine derivative [VIII] are condensed by a method similar to the synthetic method A to give the present synthetic intermediate [II]. Then, the hydroxyl group of the compound [II] is oxidized by a general oxidation method (for example, Swern oxidation method, Moffatt oxidation method, Dess-Martin oxidation method or the like) to give the present compound [I].

Synthetic Method C

The compound [III] and the amine derivative [IX] are condensed by a method similar to the synthetic method A to give the compound [IV]. Then, the hydroxyl group of the compound [IV] is oxidized by a general oxidation method (for example, Swern oxidation method, Moffatt oxidation method, Dess-Martin oxidation method or the like) to give the compound [V]. Further, the compound [V] is reacted with potassium cyanide to give the cyanohydrin derivative [VI]. Then, the compound [VI] is reacted with acetyl chloride and a lower alcohol (for example, ethanol or the like) to convert it into an iminoester derivative, and this derivative is reacted with the aminoalcohol derivative [X] to give the present synthetic intermediate [II]. Then, this intermediate is oxidized by the same oxidation method as the synthetic method B to give the present compound [I].

The amine derivatives [VII], [VIII] and [IX] to be used in these methods can be synthesized by the method described in WO 93/25574 or J. Med. Chem., 33, 2707–2714 (1990).

The above-mentioned compound [III] can be synthesized, for example, by the following typical method or similar methods.

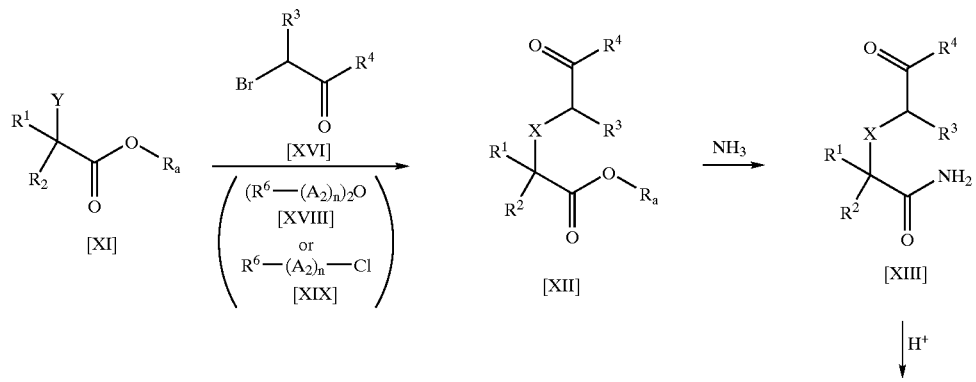

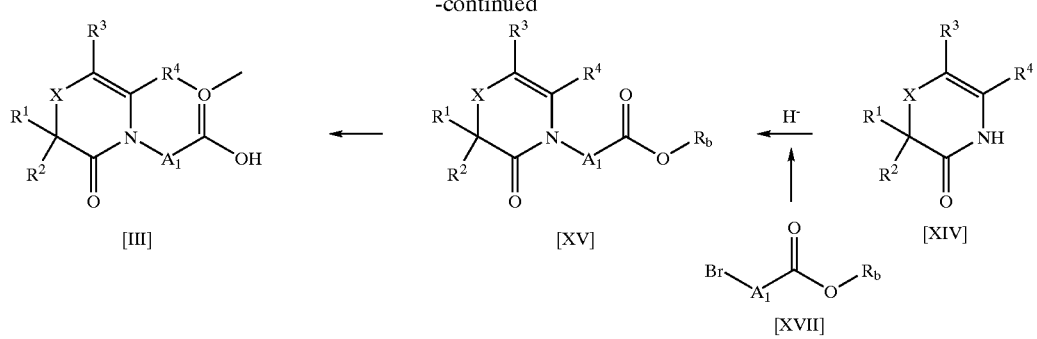

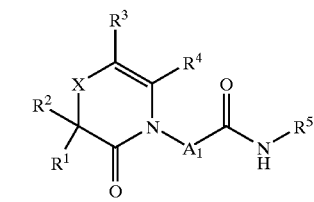

In the above synthetic route, X is S or $R^6$—$(A_2)_n$—N, and Y is —SH, —$NH_2$ or —NHR (wherein R is $R^6$—$(A_2)_n$). $R_a$ and $R_b$, being the same or different, are lower alkyl.

This synthetic route is described specifically.

The compound [XI] is reacted with the compound [XVI] under a basic condition to give the compound [XII]. (When Y is —$NH_2$, the compound [XI] is reacted with the compound [XVI] and then with the acid anhydride [XVIII] or the acid chloride [XIX] to give the compound [XII].) Then, the compound [XII] is reacted with ammonia to convert it into the amide derivative [XIII], and this derivative is cyclized by refluxing it under an acidic condition to give the compound [XIV]. Then, after adding a metal hydride, the compound [XIV] is reacted with the compound [XVII] to give the compound [XV]. The ester moiety of the compound [XV] is hydrolyzed under a basic condition to give the compound [III].

The compound [III] can also be synthesized by a method described in Japanese Laid-open Patent Publication No. 35176/1983.

The compound [II] is a novel compound and a useful synthetic intermediate of the present compound [I]. In the formula, X, $R^1$, $R^2$, $R^3$, $R^4$, $R^7$, $A_1$ and $A_3$ have the same definitions as in the general formula [I]. Preferred examples of the present synthetic intermediate [II] are compounds corresponding to the above-mentioned preferred examples of the present compound [I].

The compounds [I] and [II] obtained by the above-mentioned methods can be converted into the above-mentioned salts by the conventional method. As mentioned above, when there are diastereomers and optical isomers in the compounds represented by the general formulae, all these isomers are included in the present invention. When an optically active starting material is used, a single diastereomer and a single optical isomer are obtained. When a racemate is used as a starting material, respective isomers can be separated by general methods such as optical resolution methods.

As described in the section of "Background Art", compounds having 3-oxo-3,4-dihydro-2H-1,4-thiazine or 2-oxo-1,2,3,4-tetrahydropyrazine as a main skeleton have scarcely been studied.

Namely, the present compounds are novel compounds which are unknown in literatures. Features of their chemical structure composing a main skeleton are shown in the general formula [I]. The targets of the study are 1) to prepare the novel compounds wherein carboxy-lower alkylene converted into amide is introduced into the nitrogen atom at the 4th-position of the 3-oxo-3,4-dihydro-2H-1,4-thiazine derivatives or into the nitrogen atom at the 1st-position of the 2-oxo-1,2,3,4-tetrahydropyrazine derivatives, and 2) to prepare the novel compounds wherein the various substituents are introduced into the nitrogen atom at the 4th-position of the 2-oxo-1,2,3,4-tetrahydropyrazine derivatives.

Focusing attention on these two points and studying precisely, the present inventors have succeeded in preparing the many novel compounds.

Administration methods of drugs can be a method of administering active compounds themselves or a method of administering the drugs in the form to be decomposed in vivo and to be converted into the active compounds, namely in the form of prodrugs. Both are widely used. The present compounds have a carboxyl group in their molecule. The present compounds can be administered in the form of the carboxylic acid and also in the form of an ester which can be converted into the carboxylic acid by hydrolysis. When the present compounds have an amino group or a hydroxyl group in their molecule, the present compounds can be administered with these groups protected with suitable protecting groups.

Further, in order to find utility of the present compounds, chymase inhibitory effects of the present compounds were studied. Details will be described later in the part of "Pharmacological Test". The present compounds exhibited excellent chymase inhibitory effects. Chymase has been reported to exist in systemic tissues such as gut, skin and lung centering around tissues of cardiovascular system and to participate in outbreaks of physiologic functions such as cardiovascular lesion, inflammation, immune functions and tissue remodeling (Journal of Clinical and Experimental Medicine, 743 (10), 743 (1995)). Chymase has been reported to participate also in outbreaks of cardiac infarction, heart failure, blood vessel restenosis after PTCA and the like (Blood Vessel & Endothelium, 5 (5), 37 (1995)), hypertension (FEBS Lett., 406, 301(1997)), diabetes complication (Biol. Chem., Hoppe Seyler (GERMANY, WEST), 369 Suppl., p299), allergic diseases (Nobuhiko Katsunuma, "Intracellular Proteolysis", p. 101–106), asthma (J. Pharmacol. Exp. Ther., 244 (1), 133 (1987)) and the like. Chymase inhibitors are expected to be effective in treating these diseases.

The present compound can be administered orally or parenterally. Examples of dosage forms are tablets, capsules, granules, powders, injections, eyedrops and the like. The present compound can be formulated into preparations by the conventional methods. For example, oral preparations such as tablets, capsules, granules and powders can be prepared by using optionally a diluent such as lactose, crystalline cellulose, starch or vegetable oil; a lubricant such as magnesium stearate or talc; a binder such as hydroxypropylcellulose or polyvinyl pyrrolidone; a disintegrator such as calcium carboxymethylcellulose or low-substituted hydroxypropylmethylcellulose; a coating agent such as hydroxypropylmethylcellulose, macrogol or silicone resin; or a film forming agent such as a gelatin film. Eyedrops can be prepared by using optionally an isotonic agent such as sodium chloride or concentrated glycerine; a buffer such as sodium phosphate or sodium acetate; a surfactant such as polyoxyethylenesorbitan monooleate, polyoxyl 40 stearate or polyoxyethylene hydrogenated castor oil; a stabilizer such as sodium citrate or disodium edetate; or a preservative such as benzalkonium chloride or paraben. pH can be in a range acceptable for ophthalmic preparations, and it is more preferably in a range of 4 to 8.

The dosage of the present compound can be selected suitably depending on symptoms, age, dosage form and the like. In case of the oral preparations, the present compound can be administered once to several times per day with a daily dose of 0.1 to 5000 mg, preferably 1 to 1000 mg.

BEST MODE FOR CARRYING OUT THE INVENTION

Examples of preparations and formulations and results of pharmacological test of the present invention are shown below. These examples do not limit the scope of the invention, but are intended to make the invention more clearly understandable.

REFERENCE EXAMPLES

Preparation of Compounds

The following Reference Examples 1 to 33 show examples of the synthesis of the amine derivatives [VII] or the aminoalcohol derivatives [VIII] described in detail in the section of "Disclosure of the Invention".

Reference Example 1

(2S)-2-(tert-Butoxycarbonyl)amino-3-phenyl-1-propanol (Reference compound No. 1-1)

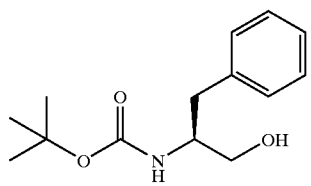

A solution of di-tert-butyl dicarbonate (1.44 g) in tetrahydrofuran (5 ml) is added dropwise to a solution of (2S)-2-amino-3-phenyl-1-propanol (1.00 g) in tetrahydrofuran (15 ml), and the mixture is stirred for 30 minutes. Then, the reaction mixture is concentrated under reduced pressure, and the resulting residue is purified by silica gel column chromatography to give the titled reference compound (1.70 g).

mp 95.2–96.7° C.

$[\alpha]_D^{20}$ –26.9° (c=1.0, methanol)

IR(KBr,cm$^{-1}$)3355,1688,1529,1444,1367,1316,1270, 1252,1169,1006,702

The following compound is obtained by a method similar to Reference Example 1.

(2S)-2-(tert-Butoxycarbonyl)amino-4-methyl-1-pentanol (Reference compound No. 1-2)

$[\alpha]_D^{20}$ –25.2° (c=1.0, methanol)

IR(Film,cm$^{-1}$)3337,2957,2870,1685,1522,1469

Reference Example 2

(2S)-2-(tert-Butoxycarbonyl)amino-3-phenylpropanal (Reference compound No. 2-1)

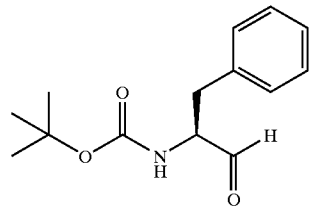

Triethylamine (17 ml) is added to a solution of (2S)-2-(tert-butoxycarbonyl)amino-3-phenyl-1-propanol (5.00 g, Reference compound No. 1-1) in dimethyl sulfoxide (100 ml). Then, a sulfur trioxide-pyridine complex (11.1 g) is added to the mixture, and the whole is stirred for 40 minutes. Water is added to the reaction mixture, and the whole is extracted with diethyl ether. The extract is washed with a saturated aqueous ammonium chloride solution, water, a saturated aqueous sodium hydrogencarbonate solution and saturated brine successively and dried over anhydrous magnesium sulfate. The extract is concentrated under reduced pressure, and the resulting residue is purified by silica gel column chromatography to give the titled reference compound (4.48 g).

IR(KBr,cm$^{-1}$)1731,1672,1561

The following compounds are obtained by a method similar to

Reference Example 2

(2S)-2-(tert-Butoxycarbonyl)amino-4-methylpentanal (Reference compound No. 2-2)

$[\alpha]_D^{20}$ +1.8° (c=0.99, chloroform)

IR(Film,cm$^{-1}$)3349,2960,2871,1708,1512,1391

(2S)-2-(Benzyloxycarbonyl)amino-3-phenylpropanal (Reference compound No. 2-3)

IR(Film,cm$^{-1}$)3331,3063,3030,2949,1706,1604,1585, 1517,1454

Reference Example 3

(2RS,3S)-3-(tert-Butoxycarbonyl)amino-2-hydroxy-4-phenylbutanenitrile (Reference compound No. 3-1)

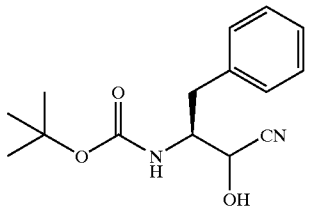

A solution of sodium hydrogensulfite (0.92 g) in water (5 ml) is added to a suspension of (2S)-2-(tert-butoxycarbonyl)amino-3-phenylpropanal (2.00 g, Reference compound No. 2-1) in water (20 ml) under ice cooling, then the temperature is raised to room temperature, and the mixture is stirred overnight. Ethyl acetate (100 ml) is added to the mixture, and the whole is stirred for one hour. Then, a solution of potassium cyanide (0.58 g) in water (5 ml) is added thereto, and the whole is further stirred for four hours. The reaction mixture is extracted with ethyl acetate, and the extract is washed with saturated brine. The extract is dried over anhydrous magnesium sulfate and concentrated under reduced pressure to give the titled reference compound (1.18 g).

The following compounds are obtained by a method similar to Reference Example 3.

(2RS,3S)-3-(tert-Butoxycarbonyl)amino-2-hydroxy-5-methylhexanenitrile (Reference compound No. 3-2)

IR(Film,cm$^{-1}$)3350,2960,2872,2248,1688,1523,1454, 1393

(2RS,3S)-3-(tert-Butoxycarbonyl)amino-4-(4-chlorophenyl)-2-hydroxybutanenitrile (Reference compound No. 3-3)

mp 110–119.5° C.

IR(KBr,cm$^{-1}$)3499,3381,2955,2932,2253,1684,1512

(2RS,3S)-3-(tert-Butoxycarbonyl)amino-2-hydroxy-5-phenylpentanenitrile (Reference compound No. 3-4)

mp 62.0–73.0° C.

IR(KBr,cm$^{-1}$)3499,3381,2955,2932,2253,1684,1512

(2RS,3S)-3-(Benzyloxycarbonyl)amino-2-hydroxy-4-phenylbutanenitrile (Reference compound No. 3-5)

IR(Film,cm$^{-1}$)3331,3063,3030,2949,1706,1604,1585, 1517,1454

Reference Example 4

Isopropyl (2RS,3S)-3-amino-2-hydroxy-4-phenylbutyrate (Reference compound No. 4-1)

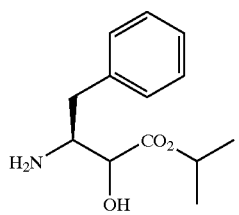

A solution of (2RS,3S)-3-(tert-butoxycarbonyl)amino-2-hydroxy-4-phenylbutanenitrile (1.00 g, Reference compound No. 3-1) in isopropanol (40 ml) is saturated with hydrogen chloride under ice cooling, then the temperature is raised to room temperature, and the solution is stirred overnight. The reaction mixture is concentrated under reduced pressure, 0.1 N hydrochloric acid is added to the resulting residue, and the whole is stirred at room temperature for 20 minutes. The reaction mixture is washed with diethyl ether, a saturated aqueous sodium hydrogencarbonate solution is added to the reaction mixture to basify the system, and the whole is extracted with ethyl acetate. The extract is washed with water and saturated brine successively and dried over anhydrous magnesium sulfate. The extract is concentrated under reduced pressure to give the titled reference compound (0.54 g).

The following compounds are obtained by a method similar to Reference Example 4.

Isopropyl (2RS,3S)-3-amino-2-hydroxy-5-methylhexanoate (Reference compound No. 4-2)

IR(Film,cm$^{-1}$)3360,3298,2956,2870,1733,1590,1468, 1386

Isopropyl (2RS,3S)-3-amino-4-(4-chlorophenyl)-2-hydroxybutyrate (Reference compound No. 4-3)

IR(KBr,cm$^{-1}$)3360,3302,2983,2836,1732,1594,1491, 1229,1207

Isopropyl (2RS,3S)-3-amino-2-hydroxy-5-phenylvalerate (Reference compound No. 4-4)

IR(Film,cm$^{-1}$)3499,3381,2955,2932,2253,1684,1512

Reference Example 5

Benzyl (2RS,3S)-3-amino-2-hydroxy-4-phenylbutyrate p-toluenesulfonate (Reference compound No. 5-1)

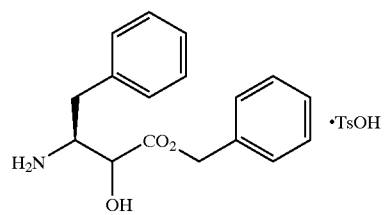

A solution of isopropyl (2RS,3S)-3-amino-2-hydroxy-4-phenylbutyrate (1.42 g, Reference compound No. 4-1), p-toluenesulfonic acid monohydrate (1.37 g) and benzyl alcohol (6 ml) in benzene (20 ml) is subjected to azeotropic distillation overnight with a Dean-Stark apparatus, and water and isopropanol are separated. Diethyl ether is added to the reaction mixture, and precipitated crystals are filtered off to give the titled reference compound (1.68 g).

mp 135.0–150.0° C.

IR(KBr,cm$^{-1}$)3335,2923,1742,1631,1499,1172,1125, 1037,1012,815,699,679

Reference Example 6

(2S)-2-(tert-Butoxycarbonyl)amino-3-(4-chlorophenyl) propionic acid (Reference compound No. 6-1)

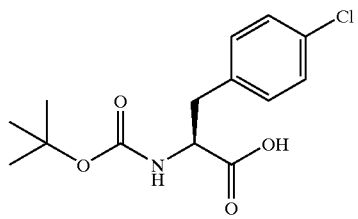

Triethylamine (1.05 ml) is added to a suspension of p-chlorophenylalanine (1.00 g) in water (5 ml). Then, a solution of di-tert-butyl dicarbonate (1.20 g) in tetrahydrofuran (5 ml) is added to the mixture, and the whole is stirred for three hours. The reaction mixture is concentrated under reduced pressure, an aqueous citric acid solution is added to the resulting residue, and the whole is extracted with ethyl acetate. The extract is washed with water and saturated brine successively and dried over anhydrous magnesium sulfate. The extract is concentrated under reduced pressure to give the titled reference compound (1.47 g).

mp 108.9–112.4° C.
$[\alpha]_D^{20}$+12.7° (c=1.0, methanol)
IR(KBr,cm$^{-1}$)3347,2990,2930,1713,1689,1522

The following compound is obtained by a method similar to Reference Example 6.

(2S)-2-(tert-Butoxycarbonyl)amino-4-phenylbutyric acid (Reference compound No. 6-2)
$[\alpha]_D^{20}$+31.5° (c=0.54, chloroform)
IR(Film,cm$^{-1}$)3322,2978,1716,1497,1455,1368

Reference Example 7

N$^1$-Methyl-N$^1$-methoxy-(2S)-2-(tert-butoxycarbonyl) amino-3-(4-chlorophenyl)propionamide (Reference compound No. 7-1)

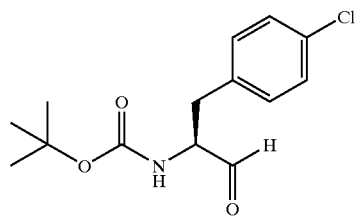

Carbonyldiimidazole (876 mg) is added to a solution of (2S)-2-(tert-butoxycarbonyl)amino-3-(4-chlorophenyl) propionic acid (1.35 g, Reference compound No. 6-1) in tetrahydrofuran (10 ml), and the mixture is stirred for 30 minutes. To the mixture is added a solution of N,O-dimethylhydroxylamine hydrochloride (483 mg) and diisopropylethylamine (941 μl) in dimethylformamide (5 ml), and the whole is stirred for three days. Ethyl acetate is added to the reaction mixture, and the whole is washed with water, 1 N hydrochloric acid, saturated aqueous sodium hydrogencarbonate solution and saturated brine successively. The organic layer is dried over anhydrous magnesium sulfate and concentrated under reduced pressure to give the titled reference compound (1.53 g).

mp 59.5–61.1° C.
$[\alpha]_D^{20}$+2.6° (c=1.0, methanol)
IR(KBr,cm$^{-1}$)3352,2983,1703,1652,1510

The following compound is obtained by a method similar to Reference Example 7.

N$^1$-Methyl-N$^1$-methoxy-(2S)-2-(tert-butoxycarbonyl) amino-4-phenylbutyramide (Reference compound No. 7-2)
$[\alpha]_D^{20}$+35.9° (c=1.0, methanol)
IR(Film,cm$^{-1}$)3324,2976,2934,1712,1662,1497

Reference Example 8

(2S)-2-(tert-Butoxycarbonyl)amino-3-(4-chlorophenyl) propanal (Reference compound No. 8-1)

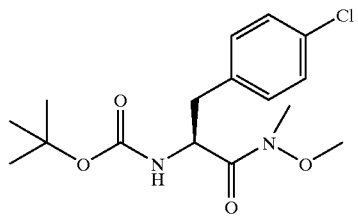

A suspension of lithium aluminum hydride (183 mg) in diethyl ether (7.5 ml) is cooled to −15° C., and a solution of N$^1$-methyl-N$^1$-methoxy-(2S)-2-(tert-butoxycarbonyl) amino-3-(4-chlorophenyl)propionamide (1.5 g, Reference compound No. 7-1) in diethyl ether (7.5 ml) is added to the suspension. The temperature is raised to −5° C., and the mixture is stirred for 30 minutes. Ethyl acetate (4 ml) is added to the reaction mixture, the whole is stirred for five minutes, and a 5% aqueous potassium hydrogensulfite solution (10 ml) is added thereto. Ethyl acetate is added to the reaction mixture, and the whole is washed with 1 N hydrochloric acid, water, a saturated aqueous sodium hydrogencarbonate solution and saturated brine successively and dried over anhydrous magnesium sulfate. The organic layer is concentrated under reduced pressure to give the titled reference compound (1.16 g).

mp 117.3–120.5° C.
$[\alpha]_D^{20}$−35.3° (c=1.0, methanol)
IR(KBr,cm$^{-1}$)3366,2984,2737,1731,1688,1517

The following compound is obtained by a method similar to Reference Example 8.

(2S)-2-tert-Butoxycarbonylamino-4-phenylbutanal (Reference compound No. 8-2)
$[\alpha]_D^{20}$+15.5° (c=1.0, methanol)
IR(Film,cm$^{-1}$)3350,2977,2930,1698,1497

Reference Example 9

(1RS,2S)-1-(2-Benzothiazolyl)-2-(tert-butoxycarbonyl) amino-3-phenyl-1-propanol (Reference compound No. 9-1)

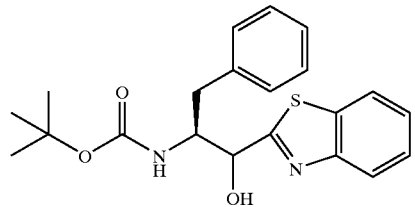

A solution of benzothiazole (0.74 g) in tetrahydrofuran (10 ml) is cooled with dry ice/methanol under a nitrogen atmosphere. A 1.6 M n-butyllithium/hexane solution (3.5 ml) is added dropwise thereto, and the mixture is stirred for 30 minutes. A solution of (2S)-2-(tert-butoxycarbonyl) amino-3-phenyl-1-propanal (1.25 g, Reference compound No. 2-1) in tetrahydrofuran (10 ml) is added to the mixture, and the whole is further stirred for four hours. A saturated aqueous ammonium chloride solution is added to the reaction mixture, the temperature is raised to room temperature, and the whole is stirred for 30 minutes. The reaction mixture is extracted with ethyl acetate, and the extract is washed with water and saturated brine successively and dried over anhydrous magnesium sulfate. The extract is concentrated under reduced pressure, and the resulting residue is purified by silica gel column chromatography to give the titled reference compound (0.93 g).

IR(KBr,cm$^{-1}$)3338,1691,1497,1392,1367,1168,759,700

The following compounds are obtained by a method similar to Reference Example 9.

(1RS,2S)-2-(tert-Butoxycarbonyl)amino-3-phenyl-1-(2-thiazolyl)-1-propanol (Reference compound No. 9-2)

(1RS,2S)-1-(2-Benzoxazolyl)-2-(tert-butoxycarbonyl) amino-3-phenyl-1-propanol (Reference compound No. 9-3)

(1RS,2S)-2-(tert-Butoxycarbonyl)amino-1-(2-oxazolyl)-3-phenyl-1-propanol (Reference compound No. 9-4)

Reference Example 10

(1RS,2S)-2-Amino-1-(2-benzothiazolyl)-3-phenyl-1-propanol hydrochloride (Reference compound No. 10-1)

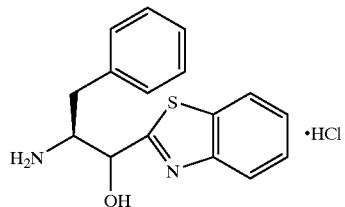

A 4 N hydrogen chloride/dioxane solution (6.3 ml) is added to (1RS,2S)-1-(2-benzothiazolyl)-2-(tert-butoxycarbonyl)amino-3-phenyl-1-propanol (0.64 g, Reference compound No. 9-1) under ice cooling, then the temperature is raised to room temperature, and the mixture is stirred for 30 minutes. The reaction mixture is concentrated under reduced pressure, diethyl ether is added to the residue, and precipitated crystals are filtered off to give the titled reference compound (0.56 g).

IR(KBr,cm$^{-1}$)2857,1600,1495,1454,1117,1067,759,700

The following compounds are obtained by a method similar to Reference Example 10.

(1RS,2S)-2-Amino-3-phenyl-1-(2-thiazolyl)-1-propanol hydrochloride (Reference compound No. 10-2)

(1RS,2S)-2-Amino-1-(2-benzoxazolyl)-3-phenyl-1-propanol hydrochloride (Reference compound No. 10-3)

(1RS,2S)-2-Amino-1-(2-oxazolyl)-3-phenyl-1-propanol hydrochloride (Reference compound No. 10-4)

Reference Example 11

(1RS,2S)-2-(Benzyloxycarbonyl)amino-1-(4,5-dihydro-1,3-thiazol-2-yl)-3-phenyl-1-propanol (Reference compound No. 11-1)

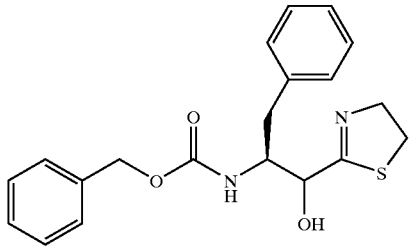

Acetyl chloride (7.8 ml) is added to a solution of ethanol (7.60 ml) in methylene chloride (20 ml) under ice cooling, and the mixture is stirred for 15 minutes. A solution of (2RS,3S)-3-(benzyloxycarbonyl)amino-2-hydroxy-4-phenylbutanenitrile (2.00 g, Reference compound No. 3-5) in methylene chloride (10 ml) is added to the mixture, and the whole is stirred overnight. The reaction mixture is concentrated under reduced pressure, and methylene chloride (30 ml) is added to the resulting residue. This solution is cooled with ice, triethylamine (3.60 ml) is added to the solution, and the mixture is stirred for 10 minutes. 2-Aminoethanethiol hydrochloride (1.46 g) is added to the mixture, then the temperature is raised to room temperature, and the whole is stirred overnight. Ethyl acetate is added to the reaction mixture, the whole is washed with a 10% aqueous citric acid solution, saturated brine, a saturated aqueous sodium hydrogencarbonate solution and saturated brine successively, and the organic layer is dried over anhydrous magnesium sulfate. The organic layer is concentrated under reduced pressure, and the resulting residue is purified by silica gel column chromatography to give the titled reference compound (1.70 g).

IR(Film,cm$^{-1}$)3328,3062,3029,2942,1703,1620,1585, 1497,1454

The following compounds are obtained by a method similar to Reference Example 11.

(1RS,2S)-2-(Benzyloxycarbonyl)amino-1-(4,5-dihydro-1,3-oxazol-2-yl)-3-phenyl-1-propanol (Reference compound No. 11-2)

IR(Film,cm$^{-1}$)3318,3062,3028,2972,1706,1670,1585, 1496,1454

(1RS,2S)-2-(Benzyloxycarbonyl)amino-1-(4,4-dimethyl-4,5-dihydro-1,3-oxazol-2-yl)-3-phenyl-1-propanol (Reference compound No. 11-3)

(1RS,2S)-2-(Benzyloxycarbonyl)amino-1-(3-oxa-1-azaspiro[4.4]non-1-en-2-yl)-3-phenyl-1-propanol (Reference compound No. 11-4)

IR(Film,cm$^{-1}$)3321,3029,2957,1715,1667,1604,1504, 1454

(1RS,2S)-2-(Benzyloxycarbonyl)amino-1-(5,5-dimethyl-4,5-dihydro-1,3-thiazol-2-yl)-3-phenyl-1-propanol (Reference compound No. 11-5)

IR(Film,cm$^{-1}$)3330,3063,3030,2958,2927,1714,1614, 1514,1454

Reference Example 12

(1RS,2S)-2-Amino-1-(4,5-dihydro-1,3-thiazol-2-yl)-3-phenyl-1-propanol (Reference compound No. 12-1)

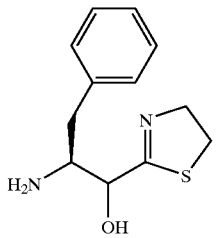

Iodotrimethylsilane (10 ml) is added to a solution of (1RS,2S)-2-(benzyloxycarbonyl)amino-1-(4,5-dihydro-1,3-thiazol-2-yl)-3-phenyl-1-propanol (650 mg, Reference compound No. 11-1) in acetonitrile (10 ml), and the mixture is stirred for 30 minutes. The reaction mixture is concentrated under reduced pressure, ethyl acetate is added to the resulting residue, and the whole is extracted with 1 N hydrochloric acid. Sodium hydrogencarbonate is added to the extract to basify the system, and the whole is extracted with ethyl acetate. The extract is washed with saturated brine and dried over anhydrous magnesium sulfate. The extract is concentrated under reduced pressure to give the titled reference compound (323 mg).

mp 82.3–90.0° C.
IR(Film,cm$^{-1}$)3320,3024,2916,1649,1578,1542,1495, 1453

The following compounds are obtained by a method similar to Reference Example 12.

(1RS,2S)-2-Amino-1-(4,5-dihydro-1,3-oxazol-2-yl)-3-phenyl-1-propanol (Reference compound No. 12-2)
IR(Film,cm$^{-1}$)3400-2900,1620,1528,1495,1451

(1RS,2S)-2-Amino-1-(4,4-dimethyl-4,5-dihydro-1,3-oxazol-2-yl)-3-phenyl-1-propanol (Reference compound No. 12-3)

(1RS,2S)-2-(Benzyloxycarbonyl)amino-1-(3-oxa-1-azaspiro[4.4]non-1-en-2-yl)-3-phenyl-1-propanol (Reference compound No. 12-4)
IR(Film,cm$^{-1}$)3286,2955,1659,1603,1524,1496,1454

(1RS,2S)-2-(Benzyloxycarbonyl)amino-1-(5,5-dimethyl-4,5-dihydro-1,3-thiazol-2-yl)-3-phenyl-1-propanol (Reference compound No. 12-5)
IR(KBr,cm$^{-1}$)3350,3280,3028,2922,1612,1559,1496, 1456

Reference Example 13

Isopropyl (2RS,3S)-3-(benzyloxycarbonyl)amino-2-hydroxy-4-phenylbutyrate (Reference compound No. 13-1)

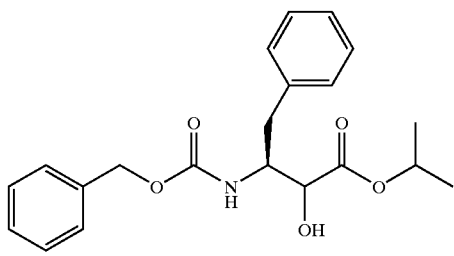

Water (10 ml) and sodium carbonate (763 mg) are added to a solution of isopropyl (2RS,3S)-3-amino-2-hydroxy-4-phenylbutyrate (800 mg, Reference compound No. 4-1) in diethyl ether (10 ml). Benzyl chloroformate (691 mg) is added to the mixture, and the whole is stirred for two hours. Ethyl acetate is added to the reaction mixture, and the whole is washed with a saturated aqueous sodium hydrogencarbonate solution, water and saturated brine successively and dried over anhydrous magnesium sulfate. The organic layer is concentrated under reduced pressure, and the resulting residue is purified by silica gel column chromatography to give the titled reference compound (1.02 g).

IR(Film,cm$^{-1}$)3360,2981,1726,1520

Reference Example 14

(2RS,3S)-3-(Benzyloxycarbonyl)amino-4-phenyl-1,2-butanediol (Reference compound No. 14-1)

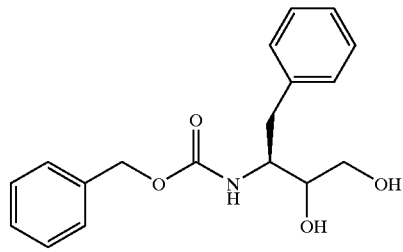

Ethanol (1 ml) and lithium bromide (36.7 mg) are added to a solution of isopropyl (2RS,3S)-3-(benzyloxycarbonyl)amino-2-hydroxy-4-phenylbutyrate (150 mg, Reference compound No. 13-1) in tetrahydrofuran (1 ml). The mixture is cooled with ice, sodium borohydride (42.1 mg) is added to the mixture, and the temperature is raised to room temperature. The whole is stirred overnight, water is added thereto, and the whole is further stirred for one hour. The reaction mixture is concentrated under reduced pressure, and the resulting residue is extracted with ethyl acetate. The extract is washed with saturated brine and dried over anhydrous magnesium sulfate. The extract is concentrated under reduced pressure to give the titled reference compound (105 mg).

IR(KBr,cm$^{-1}$)3362,3214,2933,2889,1694,1604,1525

Reference Example 15

(2RS,3S)-3-(Benzyloxycarbonyl)amino-1-(tert-butyldimethylsilyl)-oxy-4-phenyl-2-butanol (Reference compound No. 15-1)

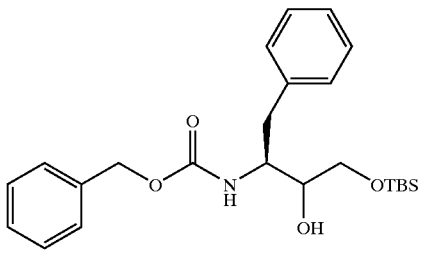

Triethylamine (69 μl) and 4-dimethylaminopyridine (catalytic amount) are added to a solution of (2RS,3S)-3-(benzyloxycarbonyl)amino-4-phenyl-1,2-butanediol (130 mg, Reference compound No. 14-1) in methylene chloride (2 ml). tert-Butyldimethylsilyl chloride (68.3 mg) is added to the mixture, and the whole is stirred overnight. Ethyl acetate is added to the reaction mixture, the whole is washed with water and saturated brine successively, and the organic layer is dried over anhydrous magnesium sulfate. The organic layer is concentrated under reduced pressure, and the resulting residue is purified by silica gel column chromatography to give the titled reference compound (149 mg).

IR(Film,cm$^{-1}$)3430,2929,2857,1701,1497

Reference Example 16

(2RS,3S)-3-Amino-1-(tert-butyldimethylsilyl)oxy-4-phenyl-2-butanol (Reference compound No. 16-1)

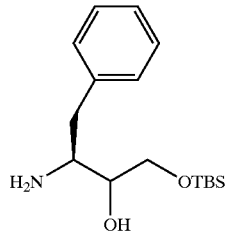

5% Palladium-carbon (130 mg) is added to a solution of (2RS,3S)-3-(benzyloxycarbonyl)amino-1-(tert-butyldimethylsilyl)oxy-4-phenyl-2-butanol (130 mg, Reference compound No. 15-1) in methanol (5 ml), and the mixture is stirred under a hydrogen atmosphere (1 atm) for three hours. The reaction mixture is filtered to remove the catalyst. The filtrate is concentrated under reduced pressure to give the titled reference compound (89.2 mg).

IR(Film,cm$^{-1}$)3433,2928,2884,2857,1698,1497

Reference Example 17

(2RS,3S)-3-Amino-2-hydroxy-4-phenylbutyramide (Reference compound No. 17-1)

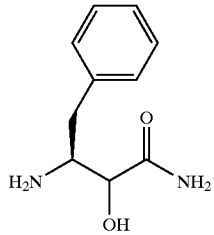

A solution of isopropyl (2RS,3S)-3-amino-2-hydroxy-4-phenylbutyrate (200 mg, Reference compound No. 4-1) in methanol (3 ml) is saturated with an ammonia gas, and the solution is sealed and stirred overnight. The reaction solution is concentrated under reduced pressure to give the titled reference compound (162 mg).

IR(KBr,cm$^{-1}$)3395,3269,2909,1668,1619,1600,1584

Reference Example 18

Isopropyl (2RS,3S)-3-(tert-butoxycarbonyl)amino-2-hydroxy-4-phenylbutyrate (Reference compound No. 18-1)

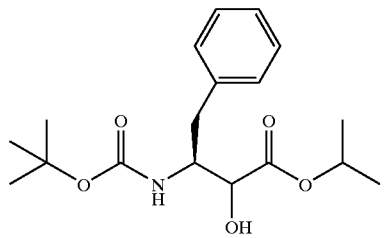

A solution of di-tert-butyl dicarbonate (101 mg) in tetrahydrofuran (1 ml) is added to a solution of isopropyl (2RS,3S)-3-amino-2-hydroxy-4-phenylbutyrate (100 mg, Reference compound No. 4-1) in tetrahydrofuran (1 ml), and the mixture is stirred for 3.5 hours. The reaction mixture is concentrated under reduced pressure, and the resulting residue is purified by silica gel column chromatography to give the titled reference compound (121 mg).

IR(Film,cm$^{-1}$)3381,2979,2933,1716,1604,1497

Reference Example 19

(2RS,3S)-3-(tert-Butoxycarbonyl)amino-2-hydroxy-4-phenylbutyric acid (Reference compound No. 19-1)

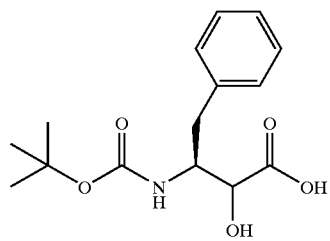

A 1 N aqueous lithium hydroxide solution (4 ml) is added to a solution of isopropyl (2RS,3S)-(tert-butoxycarbonyl)amino-2-hydroxy-4-phenylbutyrate (950 mg) in methanol (10 ml), and the mixture is stirred for three hours. The reaction mixture is washed with diethyl ether, 1 N hydrochloric acid is added to the mixture to acidify the system, and the whole is extracted with ethyl acetate. The extract is washed with saturated brine and dried over anhydrous magnesium sulfate. The extract is concentrated under reduced pressure to give the titled reference compound (801 mg).

Reference Example 20

$N^1$-Isopropyl-(2RS,3S)-3-(tert-butoxycarbonyl)amino-2-hydroxy-4-phenylbutyramide (Reference compound No. 20-1)

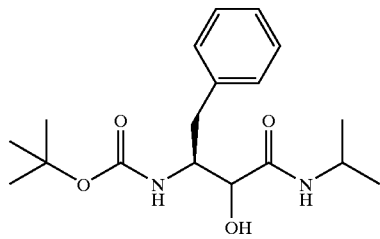

N-Methylmorpholine (200 μl) is added to a solution of (2RS,3S)-(tert-butoxycarbonyl)amino-2-hydroxy-4-phenylbutyric acid (440 mg, Reference compound No. 19-1) in tetrahydrofuran (5 ml), and the mixture is cooled to −10° C. Isobutyl chloroformate (230 μl) is added to the mixture, and the whole is stirred for 20 minutes. Further, a solution of isopropylamine and N-methylmorpholine (200 μl) in tetrahydrofuran (5 ml) is added thereto, and the whole is stirred for two hours. Ethyl acetate is added to the reaction mixture, the whole is washed with water and saturated brine successively, and the organic layer is dried over anhydrous magnesium sulfate. The organic layer is concentrated under reduced pressure, and the resulting residue is washed with diisopropyl ether to give the titled reference compound (329 mg).

mp 126.0–145.0° C.

IR(KBr,cm$^{-1}$)3444,3310,2979,1705,1678,1634,1526, 1496

The following compound is obtained by a method similar to Reference Example 20

$N^1,N^1$-Dimethyl-(2RS,3S)-3-(tert-butoxycarbonyl)amino-2-hydroxy-4-phenylbutyramide (Reference compound No. 20-2)

Reference Example 21

$N^1$-Isopropyl-(2RS,3S)-3-amino-2-hydroxy-4-phenylbutyramide (Reference compound No. 21-1)

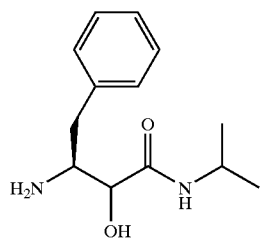

A 4 M hydrogen chloride/ethyl acetate solution (2 ml) is added to $N^1$-isopropyl-(2RS,3S)-3-(tert-butoxycarbonylamino)-2-hydroxy-4-phenyl-butyramide (300 mg, Reference compound No. 20-1), and the mixture is stirred for five hours. The reaction mixture is concentrated under reduced pressure, a saturated aqueous sodium hydrogencarbonate solution is added to the resulting residue, and the whole is extracted with ethyl acetate. The extract is washed with water and saturated brine successively and dried over anhydrous magnesium sulfate. The extract is concentrated under reduced pressure to give the titled reference compound (212 mg).

The following compound is obtained by a method similar to Reference Example 21.

$N^1,N^1$-Dimethyl-(2RS,3S)-3-amino-2-hydroxy-4-phenylbutyramide (Reference compound No. 21-2)

Reference Example 22

$N^1$-Methoxy-(2S)-2-(tert-butoxycarbonyl)amino-3-phenylpropionamide (Reference compound No. 22-1)

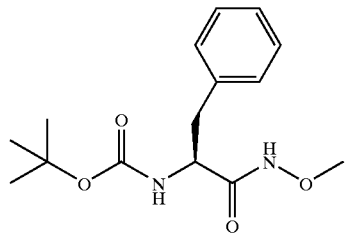

N-Methylmorpholine (0.54 ml), 1-hydroxybenzotriazole (611 mg) and O-methylhydroxylamine hydrochloride (350 mg) are added to a solution of (2S)-2-(tert-butoxycarbonyl)amino-3-phenyl-1-propionic acid (1.00 g) in methylene chloride (7.5 ml). The mixture is cooled with ice, and 1-(3-dimethylaminopropyl)-3-ethylcarbodiimide hydrochloride (867 mg) is added to the mixture. The temperature is raised to room temperature, and the whole is stirred overnight. Ethyl acetate is added to the reaction mixture, the whole is washed with a 0.1 N aqueous sodium hydroxide solution, 1 N hydrochloric acid and saturated brine successively, and the organic layer is dried over anhydrous magnesium sulfate. The organic layer is concentrated under reduced pressure to give the titled reference compound (1.11 g).

$[\alpha]_D^{20}$−6.2° (c=1.0, methanol)

IR(KBr,cm$^{-1}$)3334,3241,1667,1522

The following compounds are obtained by a method similar to Reference Example 22.

$N^1$-Methoxy-$N^1$-methyl-(2S)-2-(tert-butoxycarbonyl)amino-3-phenylpropionamide (Reference compound No. 22-2)

$[\alpha]_D^{20}$+4.3° (c=1.0, methanol)

IR(Film,cm$^{-1}$)3323,1712,1662,1496

(2S)-2-(tert-Butoxycarbonyl)amino-1-morpholino-3-phenyl-1-propanone (Reference compound No. 22-3)

$[\alpha]_D^{20}$+9.0° (c=1.0, methanol)

IR(Film,cm$^{-1}$)3306,2975,2929,2859,1708,1640,1495, 1454,1391

(2S)-2-(tert-Butoxycarbonyl)amino-3-phenyl-1-piperidino-1-propanone (Reference compound No. 22-4)

$[\alpha]_D^{20}$+1.8° (c=0.99, methanol)

IR(Film,cm$^{-1}$)3293,2975,2936,1708,1632,1494

(2S)-1-{(2S)-2-(Aminocarbonyl)pyrrolidin-1-yl}-2-(tert-butoxycarbonyl)amino-3-phenyl-1-propanone (Reference compound No. 22-5)

IR(Film,cm$^{-1}$)3318,1692,1641,1445,1168,752

Reference Example 23

N[1]-Methoxy-(2S)-2-amino-3-phenylpropionamide hydrogen trifluoroacetate (Reference compound No. 23-1)

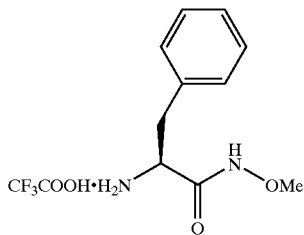

Trifluoroacetic acid (4.0 ml) is added to N[1]-methoxy-(2S)-2-(tert-butoxycarbonyl)amino-3-phenylpropionamide (600 mg, Reference compound No. 22-1), and the mixture is stirred for 10 minutes. The reaction mixture is concentrated under reduced pressure, ethyl acetate is added to the resulting residue, and the whole is extracted with 1 N hydrochloric acid. A saturated sodium hydrogencarbonate solution is added to the extract to basify the system, and the whole is extracted with ethyl acetate. The extract is washed with saturated brine and dried over anhydrous magnesium sulfate. The extract is concentrated under reduced pressure to give the titled reference compound (70.8 mg).

The following compound is obtained by a method similar to Reference Example 23.

N[1]-Methoxy-N[1]-methyl-(2S)-2-amino-3-phenyl-1-propionamide hydrogen trifluoroacetate (Reference compound No. 23-2)

Reference Example 24

(2S)-2-Amino-1-morpholino-3-phenyl-1-propanone hydrochloride (Reference compound No. 24-1)

A 4 N hydrogen chloride/ethyl acetate solution (7 ml) is added to a solution of (2S)-2-(tert-butoxycarbonyl)amino-1-morpholino-3-phenyl-1-propanone (3.10 g, Reference compound No. 22-3) in ethyl acetate (7 ml), and the mixture is stirred for four hours. The reaction mixture is concentrated under reduced pressure to give the titled reference compound (2.36 g).

mp 232.4–236.6° C.
$[\alpha]_D^{20}$+63.9° (c=1.00, methanol)
IR(Film,cm$^{-1}$)3050,2856,1659,1597,1573,1506,1468, 1453,1442

The following compounds are obtained by a method similar to Reference Example 24.

(2S)-2-Amino-3-phenyl-1-piperidino-1-propanone hydrogen trifluoroacetate (Reference compound No. 24-2)
mp 149–154° C.
$[\alpha]_D^{20}$+54.4° (c=1.00, methanol)
IR(Film,cm$^{-1}$)3050,2856,1659,1597,1573,1506,1468, 1453,1442

(2S)-2-Amino-1-{(2S)-2-(aminocarbonyl)pyrrolidin-1-yl}-3-phenylpropanone hydrochloride (Reference compound No. 24-3)
mp 120° C.
$[\alpha]_D^{20}$–13.9° (c=1.00, methanol)
IR(KBr,cm$^{-1}$)3700–2500,1653,1497

Reference Example 25

(2S)-2-(Benzyloxycarbonyl)amino-1-{4-(tert-butoxycarbonyl)-piperazin-1-yl}-3-phenyl-1-propanone (Reference compound No. 25-1)

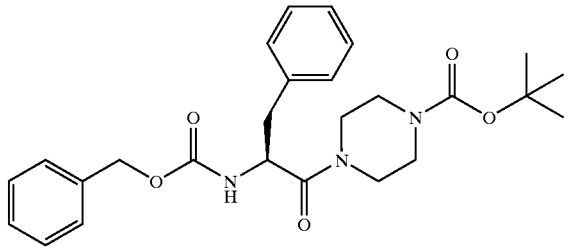

N-Methylmorpholine (1.3 ml), hydroxybenzotriazole (2.03 g) and tert-butyl piperazinecarboxylate (2.24 ml) are added to a solution of (2S)-2-(benzyloxycarbonyl)amino-3-phenyl-1-propionic acid (2.99 g) in methylene chloride (30 ml). The mixture is cooled with ice, 1-(3-dimethylaminopropyl)-3-ethylcarbodiimide hydrochloride (2.30 g) is added to the mixture, and the whole is stirred overnight. Ethyl acetate is added to the reaction mixture, the whole is washed with a 0.1 N aqueous sodium hydroxide solution, 0.1 N hydrochloric acid and saturated brine successively, and the organic layer is dried over anhydrous magnesium sulfate. The organic layer is concentrated under reduced pressure to give the titled reference compound (4.68 g).

$[\alpha]_D^{20}$+14.4° (c=1.00, methanol)
IR(Film,cm$^{-1}$)3292,3007,2976,2930,1699,1640,1529, 1497

Reference Example 26

(2S)-2-Amino-1-{4-(tert-butoxycarbonyl)piperazin-1-yl}-3-phenyl-1-propanone (Reference compound No. 26-1)

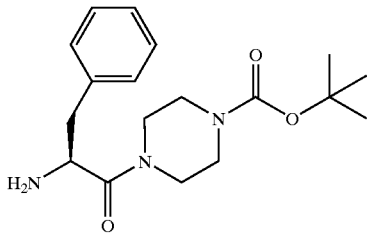

A solution of (2S)-2-(benzyloxycarbonyl)amino-1-{4-(tert-butoxycarbonyl)piperazin-1-yl}-3-phenyl-1-propanone (4.2 g, Reference compound No. 25-1) in ethanol (30 ml) is saturated with a nitrogen gas. Then, 5% palladium hydroxide/carbon (2.1 g) is added to the solution, and the whole is stirred overnight under a hydrogen atmosphere (4.2 kgf/cm$^{-1}$). The reaction mixture is filtered to remove the catalyst. The filtrate is concentrated under reduced pressure, ethyl acetate is added to the resulting residue, and the whole is extracted with a 10% aqueous citric acid solution. Sodium hydrogencarbonate is added to the extract to basify the system, and the whole is extracted with ethyl acetate. The extract is dried over anhydrous magnesium sulfate and concentrated under reduced pressure to give the titled reference compound (1.32 g).

IR(KBr,cm$^{-1}$)3367,1694,1641,1454,1419

Reference Example 27

(2S)-2-(tert-Butoxycarbonyl)amino-1,3-diphenyl-1-propanone (Reference compound No. 27-1)

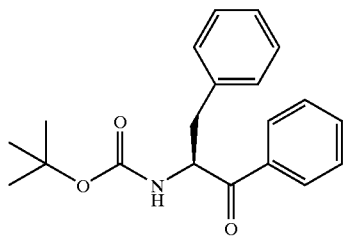

A solution of N$^1$-methoxy-N$^1$-methyl-(2S)-2-(tert-butoxycarbonyl)-amino-3-phenylpropionamide (700 mg, Reference compound No. 22-2) in anhydrous tetrahydrofuran (10 ml) is cooled to −78°C., a 1.8 N phenyllithium/cyclohexane/ether solution (6.31 ml) is added thereto, and the mixture is stirred for two hours. A saturated aqueous ammonium chloride solution (20 ml) is added to the reaction mixture, and the whole is extracted with ethyl acetate. The extract is washed with saturated brine and dried over anhydrous magnesium sulfate. The extract is concentrated under reduced pressure, and the resulting residue is purified by silica gel column chromatography to give the titled reference compound (425 mg).

mp 109.0–110.0° C.

$[\alpha]_D^{20}$+15.6° (c=1.0, methanol)

IR(KBr,cm$^{31\ 1}$)3353,3325,1685,1597,1530

Reference Example 28

(2S)-2-Amino-1,3-diphenyl-1-propanone hydrochloride (Reference compound No. 28-1)

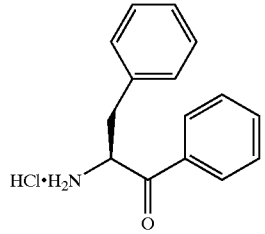

A 4 N hydrogen chloride/ethyl acetate solution (8 ml) is added to a solution of (2S)-2-(tert-butoxycarbonyl)amino-1,3-diphenylpropanone (300 mg, Reference compound No. 27-1) in ethyl acetate (10 ml), and the mixture is stirred for three hours. The reaction mixture is concentrated under reduced pressure, and the resulting residue is washed with hexane to give the titled reference compound (224 mg).

mp 215.0–226.0° C.

$[\alpha]_D^{20}$ +72.4° (c=1.0, methanol)

IR(KBr,cm$^{-1}$)3065,2820,1690,1594,1497

Reference Example 29

(4RS)-2-Phenyl-4-phenylmethyl-5(4H)-oxazolone (Reference compound No. 29-1)

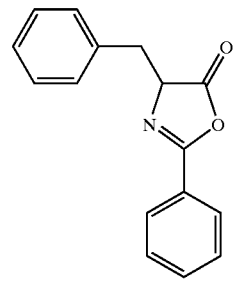

A suspension of N-benzoyl-DL-phenylalanine (5.39 g) and acetic anhydride (12.3 g) is stirred at 80° C. for 40 minutes under a nitrogen atmosphere. The reaction mixture is concentrated under reduced pressure to give the titled reference compound (4.30 g).

mp 70.0–72.0° C.

IR(KBr,cm$^{-1}$)1826,1813,1647,1297,1079,1048,902,695

Reference Example 30

(3RS)-3-Benzoylamino-2-oxo-4-phenyl-1,1,1-trifluorobutane (Reference compound No. 30-1)

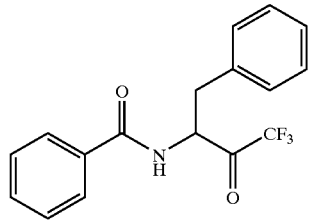

A solution of (4RS)-2-phenyl-4-phenylmethyl-5(4H)-oxazolone (3.65 g, Reference compound No. 29-1) in trifluoroacetic anhydride (6.13 g) is stirred for one day under a nitrogen atmosphere. The solution is concentrated under reduced pressure, and oxalic acid (1.97 g) is added to the resulting residue. The mixture is heated at 120° C. and stirred for 30 minutes. The reaction mixture is cooled with ice, water is added to the mixture, and the whole is extracted with ethyl acetate. The extract is washed with water, a saturated aqueous sodium hydrogencarbonate solution and saturated brine successively and dried over anhydrous magnesium sulfate. The extract is concentrated under reduced pressure to give the titled reference compound (3.23 g).

mp 148.5–157.0° C.

IR(KBr,cm$^{-1}$)3344,1763,1654,1624,1554,1166,1110,695

The following compound is obtained by a method similar to Reference Example 30.

(2RS)-2-Benzoylamino-4,4,5,5,6,6,6-heptafluoro-3-oxo-1-phenylhexane (Reference compound No. 30-2)

mp 120.0–125.0° C.

IR(KBr,cm$^{-1}$)3292,3031,2908,1753,1723,1653,1580,1525,1491,1445,1347

Reference Example 31

(2RS,3RS)-3-Benzoylamino-2-hydroxy-4-phenyl-1,1,1-trifluorobutane (Reference compound No. 31-1)

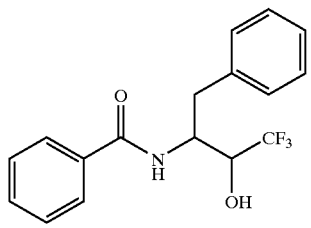

Sodium borohydride (0.37 g) is added to a solution of (3RS)-3-benzoylamino-2-oxo-4-phenyl-1,1,1-trifluorobutane (3.12 g, Reference compound No. 30-1) in ethanol (25 ml), and the mixture is stirred at 35° C. for four hours. The reaction mixture is cooled with ice, 6 N hydrochloric acid is added to the mixture, and the whole is extracted with ethyl acetate. The extract is washed with water, a saturated aqueous sodium hydrogencarbonate solution and saturated brine successively and dried over anhydrous magnesium sulfate. The extract is concentrated under reduced pressure to give the titled reference compound (3.00 g).

mp 176.0–183.0° C.

IR(KBr,cm$^{-1}$)3309,1646,1538,1237,1261,1190,1133,699

The following compound is obtained by a method similar to Reference Example 31.

(2RS,3RS)-2-Benzoylamino-4,4,5,5,6,6,6-heptafluoro-3-hydroxy-1-phenylhexane (Reference compound No. 31-2)

mp 152.0–160.0° C.

IR(KBr,cm$^{-1}$)3216,3065,3030,2931,1644,1576,1538, 1494,1454,1356

Reference Example 32

(2RS,3RS)-3-Amino-2-hydroxy-4-phenyl-1,1,1-trifluorobutane hydrochloride (Reference compound No. 32-1)

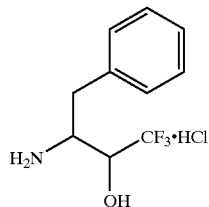

12 N Hydrochloric acid is added to a suspension of (2RS,3RS)-3-benzoylamino-2-hydroxy-4-phenyl-1,1,1-trifluorobutane (3.00 g, Reference compound No. 31-1), ethanol (60 ml) and water (60 ml), and the mixture is refluxed for one day. After standing, the reaction mixture is concentrated under reduced pressure, diethyl ether is added to the resulting residue, and the whole is extracted with water. The extract is concentrated under reduced pressure to give the titled reference compound (1.58 g).

mp 218.0–226.0° C.

IR(KBr,cm$^{-1}$)3318,3128,2924,1601,1513,1285,1181, 1156

Reference Example 33

(2RS,3RS)-2-Amino-4,4,5,5,6,6,6-heptafluoro-3-hydroxy-1-phenylhexane (Reference compound No. 33-1)

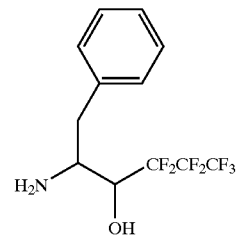

Lithium aluminum hydride (118 mg) is added to a solution of (2RS,3RS)-2-benzoylamino-4,4,5,5,6,6,6-heptafluoro-3-hydroxy-1-phenylhexane (1.10 g, Reference compound No. 31-2) in anhydrous tetrahydrofuran (20 ml), and the mixture is stirred for three days. The reaction mixture is filtered through Celite to remove impurities. The filtrate is concentrated under reduced pressure, diethyl ether is added to the resulting residue, and the whole is extracted with 0.1 N hydrochloric acid. Sodium hydrogencarbonate is added to the extract to basify the system, and the whole is extracted with ethyl acetate. The extract is washed with saturated brine and dried over anhydrous magnesium sulfate. The extract is concentrated under reduced pressure to give the titled reference compound (164 mg).

IR(Film,cm$^{-1}$)3357,3312,3065,2915,2873,1644,1614, 1558,1540,1496

The following Reference Examples 34 to 65 show examples of the synthesis of the carboxylic acid derivatives [III] described in detail in the section of "Disclosure of the Invention".

Reference Example 34

Ethyl 2-(2,2-diethoxyethylthio)acetate (Reference compound No. 34-1)

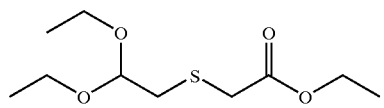

Sodium ethoxide (2.83 g) is added to a solution of ethyl thioglycolate (5.00 g) and bromoacetaldehyde diethylacetal (8.20 g) in ethanol (150 ml), and the mixture is refluxed for three hours. The reaction mixture is allowed to stand at room temperature, water is added to the mixture, and the whole is extracted with diethyl ether. The extract is washed with saturated brine and dried over anhydrous magnesium sulfate. The extract is concentrated under reduced pressure, and the resulting residue is purified by silica gel column chromatography to give the titled reference compound (5.75 g).

IR(Film,cm$^{-1}$)3439,1735,1478,1445,1273

Reference Example 35

Methyl 2-(2-hydroxybutylthio)acetate (Reference compound No. 35-1)

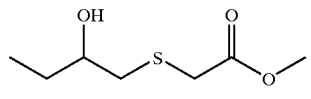

Sodium methoxide (1.94 g) is added to a solution of methyl thioglycolate (3.18 g) in methanol (60 ml), and the mixture is stirred for 10 minutes. Then, 2-butylene oxide (3.1 ml) is added to the mixture, and the whole is stirred overnight. The reaction mixture is concentrated under reduced pressure, and the resulting residue is purified by silica gel column chromatography to give the titled reference compound (4.35 g).

IR(Film,cm$^{-1}$)3437,1735,1437,1284

Reference Example 36

Methyl 2-(2-oxobutylthio)acetate (Reference compound No. 36-1)

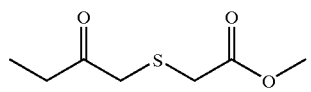

Triethylamine (28.3 ml) is added to a solution of methyl 2-(2-hydroxybutylthio)acetate (6.00 g, Reference compound No. 35-1) in dimethyl sulfoxide (180 ml). A sulfur trioxide-pyridine complex (20.0 g) is added to the mixture, and the whole is stirred for one hour. Water is added to the reaction mixture, and the whole is stirred for 20 minutes and extracted with ethyl acetate. The extract is washed with water, 1 N hydrochloric acid and saturated brine successively and dried over anhydrous magnesium sulfate. The extract is concentrated under reduced pressure, and the resulting residue is purified by silica gel column chromatography to give the titled reference compound (5.93 g).

IR(Film,cm$^{-1}$)1736,1710,1588,1436,1410,1351,1280

Reference Example 37

Methyl 2-(2,2-dimethoxybutylthio)acetate (Reference compound No. 37-1)

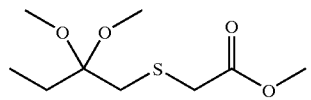

Methyl orthoformate (10.8 ml) and p-toluenesulfonic acid monohydrate (catalytic amount) are added to a solution of methyl 2-(2-oxobutylthio)acetate (5.80 g, Reference compound No. 36-1) in methanol (60 ml), and the mixture is refluxed for two hours. The reaction mixture is cooled to 0° C., sodium methoxide (1.98 g) is added to the mixture, and the whole is stirred for 20 minutes. The reaction mixture is concentrated under reduced pressure, ethyl acetate is added to the resulting residue, and the whole is washed with saturated brine. The organic layer is dried over anhydrous magnesium sulfate, and the solvent is distilled away under reduced pressure to give the titled reference compound (6.85 g).

IR(Film,cm$^{-1}$)1735,1458,1436,1344,1281,1197,1156

Reference Example 38

2-(2,2-Diethoxyethylthio)acetamide (Reference compound No. 38-1)

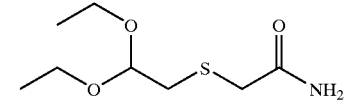

An ammonia gas is bubbled through a solution of ethyl 2-(2,2-diethoxyethylthio)acetate (4.90 g, Reference compound No. 34-1) in methanol (100 ml) under ice cooling for 20 minutes. The temperature is raised to room temperature, and the solution is stirred for 20 hours. The reaction solution is concentrated under reduced pressure, and the resulting residue is purified by silica gel column chromatography to give the titled reference compound (3.88 g).

IR(Film,cm$^{-1}$)3421,3197,1673,1124,1057

The following compound is obtained by a method similar to Reference Example 38.

2-(2,2-Dimethoxybutylthio)acetamide (Reference compound No. 38-2)

IR(Film,cm$^{-1}$)3368,3174,1643,1460,1431,1403,1385,1345,1304

Reference Example 39

3,4-Dihydro-2H-1,4-thiazin-3-one (Reference compound No. 39-1)

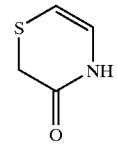

p-Toluenesulfonic acid monohydrate (catalytic amount) is added to a solution of 2-(2,2-diethoxyethylthio)acetamide (3.19 g, Reference compound No. 38-1) in toluene (30 ml), and the mixture is refluxed for 15 hours. The reaction mixture is allowed to stand at room temperature and washed with a saturated aqueous sodium hydrogencarbonate solution and saturated brine successively. The organic layer is dried over anhydrous magnesium sulfate and concentrated under reduced pressure, and the resulting residue is purified by silica gel column chromatography to give the titled reference compound (1.21 g).

mp 73.0–74.0° C.

IR(KBr,cm$^{-1}$)3252,3106,3003,1615,1468,1382,1320,1240

The following compound is obtained by a method similar to Reference Example 39.

5-Ethyl-3,4-dihydro-2H-1,4-thiazin-3-one (Reference compound No. 39-2)

IR(KBr,cm$^{-1}$)3191,3081,1691,1635,1484,1456,1439,1405,1371,1274,1230

Reference Example 40

2-Mercaptoacetamide (Reference compound No. 40-1)

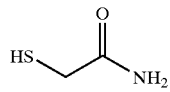

An ammonia gas is bubbled through methyl thioglycolate (3.00 g) for four hours. Nitrogen is bubbled through the reaction mixture to replace ammonia with nitrogen. The resulting methanol is distilled away under reduced pressure to give the titled reference compound (2.15 g).

IR(KBr,cm$^{-1}$)3370,2546,1655,1381,1248

Reference Example 41

5-Phenyl-3,4-dihydro-2H-1,4-thiazin-3-one (Reference compound No. 41-1)

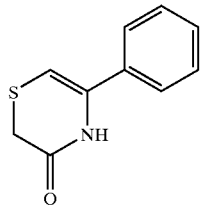

Triethylamine (4.55 g) is added to a solution of 2-mercaptoacetamide (8.00 g, Reference compound No. 40-1) in ethanol (70 ml), then phenacyl bromide (17.5 g) is added to the mixture, and the whole is stirred for four hours. The reaction mixture is concentrated under reduced pressure, water and 0.1 N hydrochloric acid are added to the resulting residue, and the whole is extracted with ethyl acetate. The extract is washed with saturated brine and dried over anhydrous magnesium sulfate. The extract is concentrated under reduced pressure. The resulting residue is suspended in ethanol (200 ml), p-toluenesulfonic acid monohydrate (catalytic amount) is added to the suspension, and the mixture is refluxed for five days. The reaction mixture is cooled to room temperature to precipitate crystals. The crystals are filtered off and washed with ethanol to give the titled reference compound (11.6 g).

mp 158.0–160.0° C.

IR(KBr,cm$^{-1}$)3174,3072,1666,1471

The following compounds are obtained by a method similar to Reference Example 41.

5-(4-Fluorophenyl)-3,4-dihydro-2H-1,4-thiazin-3-one (Reference compound No. 41-2)

mp 142.0–160.0° C.

IR(KBr,cm$^{-1}$)3072,1659,1459,1157

5-(4-Methoxyphenyl)-3,4-dihydro-2H-1,4-thiazin-3-one (Reference compound No. 41-3)

mp 150.0–152.5° C.

IR(KBr,cm$^{-1}$)3213,1670,1608,1515

Reference Example 42

(2RS)-2-Isopropyl-3,4-dihydro-2H-1,4-thiazin-3-one (Reference compound No. 42-1)

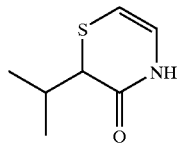

A solution of lithium diisopropylamide (10.4 mmol) in tetrahydrofuran (5 ml) is cooled to −78° C. under a nitrogen atmosphere, and a solution of 3,4-dihydro-2H-1,4-thiazin-3-one (500 mg, Reference compound No. 39-1) in tetrahydrofuran (5 ml) is added dropwise thereto. Then, 2-bromopropane (640 mg) is added dropwise thereto, and the mixture is stirred for three hours. The temperature is raised to room temperature, and the mixture is stirred for two days. Water is added to the reaction mixture under ice cooling, and the whole is extracted with ethyl acetate. The extract is washed with water and saturated brine successively and dried over anhydrous magnesium sulfate. The extract is concentrated under reduced pressure, and the resulting residue is purified by silica gel column chromatography to give the titled reference compound (100 mg).

mp 101.0–105.5° C.

IR(KBr,cm$^{-1}$)3188,1664,1613

The following compounds are obtained by a method similar to Reference Example 42.

(2RS)-5-Ethyl-2-isopropyl-3,4-dihydro-2H-1,4-thiazin-3-one (Reference compound No. 42-2)

(2RS)-2-Isopropyl-5-phenyl-3,4-dihydro-2H-1,4-thiazin-3-one (Reference compound No. 42-3)

mp 134.5–140.5° C.

IR(KBr,cm$^{-1}$)3186,3072,1657,1469,1340

(2RS)-5-(4-Fluorophenyl)-2-isopropyl-3,4-dihydro-2H-1,4-thiazin-3-one (Reference compound No. 42-4)

IR(KBr,cm$^{-1}$)3190,3069,1660,1608,1509,1237

(2RS)-2-Isopropyl-5-(4-methoxyphenyl)-3,4-dihydro-2H-1,4-thiazin-3-one (Reference compound No. 42-5)

mp 99.0–110.0° C.

IR(KBr,cm$^{-1}$)3187,3066,1660,1607,1513,1256

(2RS)-2-Methyl-3,4-dihydro-2H-1,4-thiazin-3-one (Reference compound No. 42-6)

IR(KBr,cm$^{-1}$)3238,1664,1445,1381

(2RS)-2-Ethyl-3,4-dihydro-2H-1,4-thiazin-3-one (Reference compound No. 42-7)

IR(KBr,cm$^{-1}$)3775,3231,3082,2967,2875,1673,1456,1378

(2RS)-2-Propyl-3,4-dihydro-2H-1,4-thiazin-3-one (Reference compound No. 42-8)

IR(KBr,cm$^{-1}$)3189,3073,1670,1614,1387

(2RS)-2-(2-Methoxyethyl)-3,4-dihydro-2H-1,4-thiazin-3-one (Reference compound No. 42-9)

IR(Film,cm$^{-1}$)3238,1674,1618,1117

Reference Example 43

Methyl 2-{(2RS)-2-isopropyl-3-oxo-3,4-dihydro-2H-1,4-thiazin-4-yl}acetate (Reference compound No. 43-1)

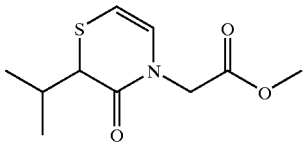

A solution of (2RS)-2-isopropyl-3,4-dihydro-2H-1,4-thiazin-3-one (70 mg, Reference compound No. 42-1) in anhydrous tetrahydrofuran (1 ml) is added to a solution of sodium hydride (39 mg) in anhydrous tetrahydrofuran (1 ml) under ice cooling, and the mixture is stirred for 10 minutes. Methyl bromoacetate (74.3 mg) is added to the mixture, the temperature is raised to room temperature, and the whole is stirred for 20 minutes. The reaction mixture is cooled with ice, water is added to the mixture, and the whole is extracted with ethyl acetate. The extract is washed with 1 N hydrochloric acid, water and saturated brine successively and dried over anhydrous magnesium sulfate. The extract is concentrated under reduced pressure, and the resulting residue is purified by silica gel column chromatography to give the titled reference compound (90.2 mg).

IR(Film,cm$^{-1}$)1756,1667,1386,1286

The following compounds are obtained by a method similar to Reference Example 43.

Ethyl 2-{(2RS)-5-ethyl-2-isopropyl-3-oxo-3,4-dihydro-2H-1,4-thiazin-4-yl}acetate (Reference compound No. 43-2)

IR(Film,cm$^{-1}$)1752,1669,1465,1368,1200

Methyl 2-{(2RS)-2-isopropyl-3-oxo-5-phenyl-3,4-dihydro-2H-1,4-thiazin-4-yl}acetate (Reference compound No. 43-3)

IR(Film,cm$^{-1}$)1754,1674,1209

Methyl 2-{(2RS)-5-(4-fluorophenyl)-2-isopropyl-3-oxo-3,4-dihydro-2H-1,4-thiazin-4-yl}acetate (Reference compound No. 43-4)

IR(Film,cm$^{-1}$)1754,1673,1508,1365,1213

Methyl 2-{(2RS)-2-isopropyl-5-(4-methoxyphenyl)-3-oxo-3,4-dihydro-2H-1,4-thiazin-4-yl}acetate (Reference compound No. 43-5)

mp. 99.0–110.0° C.

IR(Film,cm$^{-1}$)1753,1671,1609,1511,1364,1248,1210,1177

Methyl 2-{(2RS)-2-methyl-3-oxo-3,4-dihydro-2H-1,4-thiazin-4-yl}acetate (Reference compound No. 43-6)

IR(Film,cm$^{-1}$)1753,1667,1389,1207

Ethyl 2-{(2RS)-2-ethyl-3-oxo-3,4-dihydro-2H-1,4-thiazin-4-yl}acetate (Reference compound No. 43-7)

IR(Film,cm$^{-1}$)1749,1667,1455,1385

Methyl 2-{(2RS)-3-oxo-2-propyl-3,4-dihydro-2H-1,4-thiazin-4-yl}acetate (Reference compound No. 43-8)

IR(Film,cm$^{-1}$)1754,1668,1619,1208

Methyl 2-{(2RS)-2-(2-methoxyethyl)-3-oxo-3,4-dihydro-2H-1,4-thiazin-4-yl}acetate (Reference compound No. 43-9)

IR(Film,cm$^{-1}$)1753,1668,1387,1208

Methyl (2RS)-2-{(2RS)-2-isopropyl-3-oxo-3,4-dihydro-2H-1,4-thiazin-4-yl}propanoate (Reference compound No. 43-10)

Ethyl (2RS)-2-{(2RS)-2-isopropyl-3-oxo-3,4-dihydro-2H-1,4-thiazin-4-yl}butyrate (Reference compound No. 43-11)

Benzyl (2RS)-2-{(2RS)-2-isopropyl-3-oxo-3,4-dihydro-2H-1,4-thiazin-4-yl}-3-phenylpropanoate (Reference compound No. 43-12)

Reference Example 44

2-{(2RS)-2-Isopropyl-3-oxo-3,4-dihydro-2H-1,4-thiazin-4-yl}acetic acid (Reference compound No. 44-1)

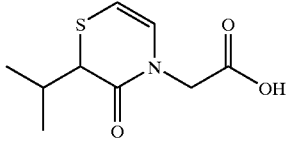

Methanol (0.15 ml) and a 1 N aqueous sodium hydroxide solution (0.34 ml) are added to a solution of methyl 2-{(2RS)-2-isopropyl-3-oxo-3,4-dihydro-2H-1,4-thiazin-4-yl}acetate (70 mg, Reference compound No. 43-1) in tetrahydrofuran (0.15 ml) under ice cooling, then the temperature is raised to room temperature, and the mixture is stirred for 15 minutes. Diethyl ether is added to the reaction mixture, and the whole is extracted with water. 2 N Hydrochloric acid is added to the extract to acidify the system, and the whole is extracted with ethyl acetate. The extract is washed with saturated brine and dried over anhydrous magnesium sulfate. The extract is concentrated under reduced pressure to give the titled reference compound (65.7 mg).

IR(KBr,cm$^{-1}$)1733,1627,1390,1201

The following compounds are obtained by a method similar to Reference Example 44.

2-{(2RS)-5-Ethyl-2-isopropyl-3-oxo-3,4-dihydro-2H-1,4-thiazin-4-yl}acetic acid (Reference compound No. 44-2)

2-{(2RS)-2-Isopropyl-3-oxo-5-phenyl-3,4-dihydro-2H-1,4-thiazin-4-yl}acetic acid (Reference compound No. 44-3)

mp 107.5–111.0° C.

IR(Film,cm$^{-1}$)1749,1627,1185,757

2-{(2RS)-5-(4-Fluorophenyl)-2-isopropyl-3-oxo-3,4-dihydro-2H-1,4-thiazin-4-yl}acetic acid (Reference compound No. 44-4)

mp 139.5–146.0° C.

IR(KBr,cm$^{-1}$)3279,1752,1724,1673,1605,1507

2-{(2RS)-2-Isopropyl-5-(4-methoxyphenyl)-3-oxo-3,4-dihydro-2H-1,4-thiazin-4-yl}acetic acid (Reference compound No. 44-5)

IR(Film,cm$^{-1}$)3440,1732,1609,1510

2-{(2RS)-2-Methyl-3-oxo-3,4-dihydro-2H-1,4-thiazin-3-one}acetic acid (Reference compound No. 44-6)

mp 72.0–80.5° C.

IR(Film,cm$^{-1}$)1735,1629,1434,1402,1199

2-{(2RS)-2-Ethyl-3-oxo-3,4-dihydro-2H-1,4-thiazin-4-yl}acetic acid (Reference compound No. 44-7)

IR(Film,cm$^{-1}$)1731,1662,1393,1355

2-{(2RS)-3-Oxo-2-propyl-3,4-dihydro-2H-1,4-thiazin-4-yl}acetic acid (Reference compound No. 44-8)

2-{(2RS)-2-(2-Methoxyethyl)-3-oxo-3,4-dihydro-2H-1,4-thiazin-4-yl}acetic acid (Reference compound No. 44-9)

IR(Film,cm$^{-1}$)3422,1729,1642,1397,1217

(2RS)-2-{(2RS)-2-Isopropyl-3-oxo-3,4-dihydro-2H-1,4-thiazin-4-yl}propanoic acid (Reference compound No. 44-10)

(2RS)-2-{(2RS)-3,4-Dihydro-2-isopropyl-3-oxo-2H-1,4-thiazin-4-yl}butyric acid (Reference compound No. 44-11)

(2RS)-2-{(2RS)-2-Isopropyl-3-oxo-3,4-dihydro-2H-1,4-thiazin-4-yl}-3-phenylpropanoic acid (Reference compound No. 44-12)

Reference Example 45

DL-Valine methyl ester hydrochloride (Reference compound No. 45-1)

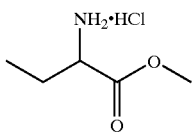

Methanol (50 ml) is cooled to −15° C., then thionyl chloride (21.2 g) is added dropwise to the methanol, and the solution is stirred for 20 minutes. DL-Valine is added to the solution, and the mixture is stirred overnight. The reaction mixture is concentrated under reduced pressure, and diethyl ether is added to the resulting residue to precipitate crystals. The precipitated crystals are filtered off to give the titled reference compound (8.68 g).

D-Valine methyl ester hydrochloride (Reference compound No. 45-2)

mp 162.5–166.0° C.

$[\alpha]_D^{21}$ −24.0° (c=2.0, methanol)

IR(KBr,cm$^{-1}$)3463,2975,1981,1740,1595,1508

The following compounds are obtained by a method similar to Reference Example 45.

L-Valine methyl ester hydrochloride (Reference compound No. 45-3)

Glycine methyl ester hydrochloride (Reference compound No. 45-4)

Methyl 2-aminoisobutyrate hydrochloride (Reference compound No. 45-5)

mp 186.0–186.5° C.

IR(KBr,cm$^{-1}$)2960,1748,1596,1522,1468,1438

Methyl (2RS)-2-aminobutyrate hydrochloride (Reference compound No. 45-6)

mp 148.0–149.1° C.

IR(KBr,cm$^{-1}$)2958,1748,1591,1522,1455

DL-Isoleucine methyl ester hydrochloride (Reference compound No. 45-7)

IR(KBr,cm$^{-1}$)3416,1745,1595,1510,1442

DL-Leucine methyl ester hydrochloride (Reference compound No. 45-8)

mp 136.5–138.9° C.

IR(KBr,cm$^{-1}$)2960,1756,1517,1232

DL-Cyclohexylglycine methyl ester hydrochloride (Reference compound No. 45-9)

mp 150.0–157.0° C.

IR(KBr,cm$^{-1}$)1740,1590,1522,1442

DL-Threonine methyl ester hydrochloride (Reference compound No. 45-10)

IR(KBr,cm$^{-1}$)3441,2633,1752,1594,1509

Methyl (2RS)-2-amino-3-methoxypropionate hydrochloride (Reference compound No. 45-11)

mp 138.2–139.4° C.

IR(KBr,cm$^{-1}$)2935,1747,1587,1519,1477,1441

DL-Phenylglycine methyl ester hydrochloride (Reference compound No. 45-12)

IR(KBr,cm$^{-1}$)1744,1581,1514,1494,1460,1430

Reference Example 46

Methyl (2RS)-2-(2-oxo-2-phenylethyl)aminoisovalerate (Reference compound No. 46-1)

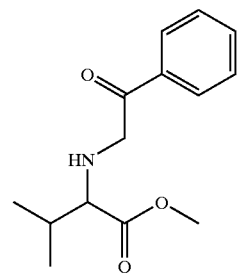

Diisopropylethylamine (7.66 ml) and 2-bromoacetophenone (4.2 g) are added to a suspension of DL-valine methyl ester hydrochloride (3.36 g, Reference compound No. 45-1) in methylene chloride (100 ml), and the mixture is refluxed for four days. The reaction mixture is allowed to stand at room temperature, diethyl ether is added to the mixture, and the whole is extracted with 0.1 N hydrochloric acid. Sodium hydrogencarbonate is added to the extract to basify the system, and the whole is extracted with ethyl acetate. The organic layer is washed with saturated brine and dried over magnesium sulfate. The organic layer is concentrated under reduced pressure to give the titled reference compound (4.92 g).

mp 32.5–50.8° C.

IR(KBr,cm$^{-1}$)3334,2964,2614,1730,1687,1598,1448

The following compounds are obtained by a method similar to Reference Example 46.

Methyl (2R)-2-(2-oxo-2-phenylethyl)aminoisovalerate (Reference compound No. 46-2)

mp 41.5–46.0° C.

$[\alpha]_D^{20}$ +33.6° (c=1.0, methanol)

IR(KBr,cm$^{-1}$)3333,3085,3029,3000,2971,2954,1727,1685,1596

Methyl (2S)-2-(2-oxo-2-phenylethyl)aminoisovalerate (Reference compound No. 46-3)

mp 44.0–48.5° C.

IR(KBr,cm$^{-1}$)3436,3333,2954,1727,1685,1596,1580,1468,1449

Ethyl 2-(2-oxo-2-phenylethyl)aminoacetate (Reference compound No. 46-4)

Methyl 2-(2-oxo-2-phenylethyl)aminoisobutyrate (Reference compound No. 46-5)

mp 51.0–61.0° C.

IR(KBr,cm$^{-1}$)3327,1725,1683,1593,1450

Methyl (2RS)-2-(2-oxo-2-phenylethyl)aminobutyrate (Reference compound No. 46-6)

IR(KBr,cm$^{-1}$)3333,1736,1690,1598,1550,1447

Methyl (2RS,3RS)-3-methyl-2-(2-oxo-2-phenylethyl)aminopentanoate (Reference compound No. 46-7)

IR(Film,cm$^{-1}$)3330,1736,1691,1597,1580,1546,1529,1502

Methyl (2RS)-4-methyl-2-(2-oxo-2-phenylethyl)aminopentanoate (Reference compound No. 46-8)

IR(KBr,cm$^{-1}$)3323,1730,1684,1453

Methyl (2RS)-2-cyclohexyl-2-(2-oxo-2-phenylethyl)aminoacetate (Reference compound No. 46-9)

IR(Film,cm$^{-1}$)3323,1727,1687,1597,1581,1495,1450

Methyl (2RS,3RS)-3-hydroxy-2-(2-oxo-2-phenylethyl)aminobutyrate (Reference compound No. 46-10)

mp 76.0–78.5° C.

IR(KBr,cm$^{-1}$)3067,1737,1604,1449

Methyl (2RS)-3-methoxy-2-(2-oxo-2-phenylethyl)aminopropionate (Reference compound No. 46-11)

IR(KBr,cm$^{-1}$)3345,3061,1740,1691,1598,1581,1449

Ethyl (2RS)-4-methoxy-2-(2-oxo-2-phenylethyl)aminobutyrate (Reference compound No. 46-12)

IR(Film,cm$^{-1}$)3322,1735,1688,1598,1580,1528,1448

Methyl (2RS)-2-(2-oxo-2-phenylethyl)amino-2-phenylacetate (Reference compound No. 46-13)

mp 45.0–54.0° C.

IR(KBr,cm$^{-1}$)3332,3083,3023,1741,1686,1597,1580,1447

Methyl (2RS)-2-{2-oxo-2-(3,4,5-trimethoxyphenyl)ethyl}aminoisovalerate (Reference compound No. 46-14)

mp 103.0–104.3° C.

IR(KBr,cm$^{-1}$)3332,2961,2842,1726,1677,1585,1511,1467

Methyl (2RS)-2-{2-(3,4-dimethoxyphenyl)-2-oxoethyl}aminoisovalerate (Reference compound No. 46-15)

IR(Film,cm$^{-1}$)3338,2960,2840,1732,1679,1595,1516,1514

Methyl (2RS)-2-{2-(3-methoxyphenyl)-2-oxoethyl}aminoisovalerate (Reference compound No. 46-16)

Methyl (2R)-2-{2-(3-methoxyphenyl)-2-oxoethyl}aminoisovalerate (Reference compound No. 46-17)

Reference Example 47

Methyl (2RS)-2-{N-acetyl-N-(2-oxo-2-phenylethyl)}aminoisovalerate (Reference compound No. 47-1)

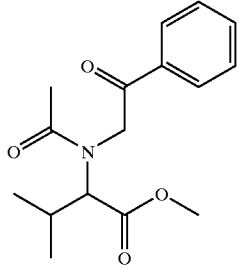

Pyridine (10.7 ml) is added to a solution of methyl (2RS)-2-(2-oxo-2-phenylethyl)aminoisovalerate (16.5 g, Reference compound No. 46-1) in methylene chloride (70 ml). The mixture is cooled with ice, and acetyl chloride (7.06 ml) is added to the mixture. Then, the temperature is raised to room temperature, and the whole is stirred overnight. The reaction mixture is concentrated under reduced pressure, and the resulting residue is diluted with ethyl acetate. The diluted solution is washed with hydrochloric acid, a saturated aqueous sodium hydrogencarbonate solution and saturated brine successively and dried over anhydrous magnesium sulfate. The diluted solution is concentrated under reduced pressure, and the resulting residue is purified by silica gel column chromatography to give the titled reference compound (18.6 g).

mp 85.5–86.0° C.

IR(KBr,cm$^{-1}$)1729,1697,1640

The following compounds are obtained by a method similar to Reference Example 47.

Methyl (2R)-2-{N-acetyl-N-(2-oxo-2-phenylethyl)}aminoisovalerate (Reference compound No. 47-2)

$[\alpha]_D^{20}$ +70.7° (c=1.1, methanol)

IR(Film,cm$^{-1}$)3454,2965,2875,1738,1702,1653,1598,1449

Methyl (2S)-2-{N-acetyl-N-(2-oxo-2-phenylethyl)}aminoisovalerate (Reference compound No. 47-3)

$[\alpha]_D^{20}$ −74.5° (c=0.99, methanol)

IR(Film,cm$^{-1}$)3460,2964,2875,1739,1701,1653,1598,1581,1449

Ethyl 2-{N-acetyl-N-(2-oxo-2-phenyl ethyl)}aminoacetate (Reference compound No. 47-4)

Methyl 2-{N-acetyl-N-(2-oxo-2-phenylethyl)}aminoisobutyrate (Reference compound No. 47-5)

IR(Film,cm$^{-1}$)1736,1698,1649,1596,1580

Methyl (2RS)-2-{N-acetyl-N-(2-oxo-2-phenylethyl)}aminobutyrate (Reference compound No. 47-6)

IR(Film,cm$^{-1}$)1737,1702,1654,1597,1580,1449

Methyl (2RS,3RS)-2-{N-acetyl-N-(2-oxo-2-phenylethyl)} amino-3-methylpentanoate (Reference compound No. 47-7)

IR(Film,cm$^{-1}$)1739,1702,1657,1598,1581

Methyl (2RS)-2-{N-acetyl-N-(2-oxo-2-phenylethyl)} amino-4-methylpentanoate (Reference compound No. 47-8)

mp 66.6–68.3° C.

IR(Film,cm$^{-1}$)1729,1702,1635,1582,1471,1452

Methyl (2RS)-2-{N -acetyl-N-(2-oxo-2-phenylethyl)} amino-2-cyclohexylacetate (Reference compound No. 47-9)

IR(Film,cm$^{-1}$)3006,1734,1702,1654,1598,1581

Methyl (2RS,3RS)-2-{N-acetyl-N-(2-oxo-2-phenylethyl)} amino-3-tertbutyldimethylsilyloxybutyrate (Reference compound No. 47-10)

IR(Film,cm$^{-1}$)3062,1745,1705,1660,1598,1581

Methyl (2RS)-2-{N-acetyl-N-(2-oxo-2-phenylethyl)} amino-3-methoxypropionate (Reference compound No. 47-11)

IR(Film,cm$^{-1}$)1745,1699,1655,1598,1449

Methyl (2RS)-2-{N-acetyl-N-(2-oxo-2-phenylethyl)} amino-4-methoxybutyrate (Reference compound No. 47-12)

IR(Film,cm$^{-1}$)1736,1702,1658,1597,1580

Methyl (2RS)-2-{N-acetyl-N-(2-oxo-2-phenylethyl)} amino-2-phenylacetate (Reference compound No. 47-13)

mp 133.5–136.0° C.

IR(KBr,cm$^{-1}$)3037,3008,1742,1685,1645,1598,1580

Methyl (2RS)-2-{N-isobutyryl-N-(2-oxo-2-phenylethyl)} aminoisovalerate (Reference compound No. 47-14)

IR(Film,cm$^{-1}$)1737,1702,1654,1470

Methyl (2R)-2-{N-isobutyryl-N-(2-oxo-2-phenylethyl)} aminoisovalerate (Reference compound No. 47-15)

$[\alpha]_D^{20}$ +59.1° (c=1.0, methanol)

IR(KBr,cm$^{-1}$)1732,1697,1648,1450

Methyl (2RS)-2-{N-(2-oxo-2-phenylethyl)-N-pivaloyl}aminoisovalerate (Reference compound No. 47-16)

Methyl (2RS)-2-{N-cyclohexylcarbonyl-N-(2-oxo-2-phenylethyl)}-aminoisovalerate (Reference compound No. 47-17)

IR(Film,cm$^{-1}$)2931,2854,1737,1701,1648,1598,1449

Methyl (2R)-2-{N-methoxyacetyl-N-(2-oxo-2-phenylethyl)}aminoisovalerate (Reference compound No. 47-18)

$[\alpha]_D^{20}$ +53.1° (c=1.0, methanol)
IR(Film,cm$^{-1}$)2963,2876,2825,1738,1700,1666,1448

Methyl (2R)-2-{N-benzoyl-N-(2-oxo-2-phenylethyl)}aminoisovalerate (Reference compound No. 47-19)

$[\alpha]_D^{20}$ +88.6° (c=1.0, methanol)
IR(Film,cm$^{-1}$)2963,1739,1702,1645,1599,1580,1493,1448

Methyl (2RS)-2-{N-(4-chlorobenzoyl)-N-(2-oxo-2-phenylethyl)}aminoisovalerate (Reference compound No. 47-20)

IR(KBr,cm$^{-1}$)1740,1701,1646,1597

Methyl (2RS)-2-{N-(4-methoxybenzoyl)-N-(2-oxo-2-phenylethyl)}-aminoisovalerate (Reference compound No. 47-21)

IR(Film,cm$^{-1}$)1740,1707

Methyl (2RS)-2-{N-(4-nitrobenzoyl)-N-(2-oxo-2-phenylethyl)}aminoisovalerate (Reference compound No. 47-22)

mp 117° C.
IR(KBr,cm$^{-1}$)1743,1711,1657,1600,1531

Methyl (2RS)-2-{N-(2-oxo-2-phenylethyl)-N-(3-phenylpropanoyl)}-aminoisovalerate (Reference compound No. 47-23)

IR(Film,cm$^{-1}$)3379,3061,3027,2963,2874,1738,1701,1656,1449

Methyl (2RS)-2-{N-(2-oxo-2-phenylethyl)-N-phenoxyacetyl}aminoisovalerate (Reference compound No. 47-24)

mp 100.0–109.5° C.
IR(KBr,cm$^{-1}$)3375,3056,2958,2875,1729,1696,1660,1591,1496

Methyl (2RS)-2-{N-(2-oxo-2-phenylethyl)-N-(2-pyridylcarbonyl)}-aminoisovalerate (Reference compound No. 47-25)

IR(Film,cm$^{-1}$)1737,1701,1646,1449

Methyl (2RS)-2-{N-(2-oxo-2-phenylethyl)-N-(3-pyridylcarbonyl)}-aminoisovalerate (Reference compound No. 47-26)

IR(Film,cm$^{-1}$)2964,2875,1740,1701,1645,1590

Methyl (2RS)-2-{N-(2-oxo-2-phenylethyl)-N-(4-pyridylcarbonyl)}-aminoisovarelate (Reference compound No. 47-27)

IR(Film,cm$^{-1}$)2965,2875,1741,1703,1650,1597,1582

Methyl (2RS)-2-{N-(2-oxo-2-phenylethyl)-N-phenylsulfonyl}aminoisovalerate (Reference compound No. 47-28)

IR(Film,cm$^{-1}$)1740,1707

Methyl (2RS)-2-[N-acetyl-N-{2-oxo-2-(3,4,5-trimethoxyphenyl)-ethyl}]aminoisovalerate (Reference compound No. 47-29)

IR(Film,cm$^{-1}$)2964,2840,1739,1696,1652,1586,1540,1506,1456

Methyl (2RS)-2-[N-benzoyl-N-{2-oxo-2-(3,4,5-trimethoxyphenyl)-ethyl}]aminoisovalerate (Reference compound No. 47-30)

IR(KBr,cm$^{-1}$)2964,2840,2645,1742,1696,1642,1586,1540,1506

Methyl (2RS)-2-[N-methoxyacetyl-N-{2-oxo-2-(3,4,5-trimethoxy-phenyl)ethyl}]aminoisovalerate (Reference compound No. 47-31)

IR(Film,cm$^{-1}$)2962,2829,1740,1692,1664,1586,1506,1453

Methyl (2RS)-2-[N-acetyl-N-{2-(3,4-dimethoxyphenyl)-2-oxoethyl}]-aminoisovalerate (Reference compound No. 47-32)

IR(Film,cm$^{-1}$)2964,2875,2841,1738,1691,1650,1596,1547,1517

Methyl (2RS)-2-[N-benzoyl-N-{2-(3,4-dimethoxyphenyl)-2-oxoethyl}]-aminoisovalerate (Reference compound No. 47-33)

IR(Film,cm$^{-1}$)3011,2964,2874,2840,1739,1689,1644,1596,1515

Methyl (2RS)-2-[N-{2-(3,4-dimethoxyphenyl)-2-oxoethyl}-N-methoxyacetyl]aminoisovalerate (Reference compound No. 47-34)

IR(Film,cm$^{-1}$)2962,2839,1738,1688,1596,1553,1516,1454

Methyl (2RS)-2-[N-benzoyl-N-{2-(3-methoxyphenyl)-2-oxoethyl}]-aminoisovalerate (Reference compound No. 47-35)

Methyl (2RS)-2-{N-methoxyacetyl-N-(2-oxo-2-phenylethyl)}aminoisovalerate (Reference compound No. 47-36)

Methyl (2RS)-2-{(N-benzoyl-N-(2-oxo-2-phenylethyl)}aminoisovalerate (Reference compound No. 47-37)

Methyl (2R)-2-{N-(2-oxo-2-phenylethyl)-N-(2-pyridylcarbonyl)}aminoisovalerate (Reference compound No. 47-38)

Methyl (2R)-2-{N-(2-oxo-2-phenylethyl)-N-(3-pyridylcarbonyl)}aminoisovalerate (Reference compound No. 47-39)

Methyl (2R)-2-{(N-(2-oxo-2-phenylethyl)-N-(4-pyridylcarbonyl)}aminoisovalerate (Reference compound No. 47-40)

Methyl (2R)-2-[N-acetyl-N-{(2-(3-methoxyphenyl)-2-oxoethyl}]aminoisovalerate (Reference compound No. 47-41)

Reference Example 48

(2RS)-2-{N-Acetyl-N-(2-oxo-2-phenylethyl)}aminoisovaleramide (Reference compound No. 48-1)

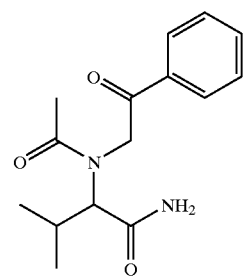

A solution of methyl (2RS)-2-{N-acetyl-N-(2-oxo-2-phenylethyl)}-aminoisovalerate (1.0 g, Reference compound No. 47-1) in methanol (5 ml) is saturated with an ammonia gas, and then the solution is sealed and stirred for six days. The reaction solution is concentrated under reduced pressure, and the resulting residue is purified by silica gel column chromatography to give the titled reference compound (926 mg).

IR(Film,cm$^{-1}$)3121,1659,1448,1297

The following compounds are obtained by a method similar to Reference Example 48.

(2R)-2-{N-Acetyl-N-(2-oxo-2-phenylethyl)}aminoisovaleramide (Reference compound No. 48-2)

$[\alpha]_D^{20}$ +3.1° (c=1.1, methanol)

IR(KBr,cm$^1$)3215,2965,2874,1668,1449

(2S)-2-{(N-Acetyl-N-(2-oxo-2-phenylethyl)}aminoisovaleramide (Reference compound No. 48-3)

$[\alpha]_D^{20}$ −3.0° (c=1.0, methanol)

IR(KBr,cm$^{-1}$)3233,2964,2874,1670,1449

2-{N-Acetyl-N-(2-oxo-2-phenylethyl)}aminoacetamide (Reference compound No. 48-4)

2-{N-Acetyl-N-(2-oxo-2-phenylethyl)} aminoisobutyramide (Reference compound No. 48-5)

IR(Film,cm$^{-1}$)3208,1682,1597,1449

(2RS)-2-{N-Acetyl-N-(2-oxo-2-phenylethyl)}aminobutyramide (Reference compound No. 48-6)

IR(Film,cm$^{-1}$)3242,1663,1449

(2RS,3RS)-2-{N-Acetyl-N-(2-oxo-2-phenylethyl)}amino-3-methyl-pentanamide (Reference compound No. 48-7)

IR(Film,cm$^{-1}$)3208,1659,1449

(2RS)-2-{N-Acetyl-N-(2-oxo-2-phenylethyl)}amino-4-methyl-pentanamide (Reference compound No. 48-8)

mp 166.7–170.7° C.

IR(KBr,cm$^{-1}$)3320,3284,1661,1630,1467,1423

(2RS)-2-{N-Acetyl-N-(2-oxo-2-phenylethyl)}amino-2-cyclohexylacetamide (Reference compound No. 48-9)

mp 175.0–192.3° C.

IR(KBr,cm$^{-1}$)3271,3060,3020,1656,1640,1467

(2RS,3RS)-2-{N-Acetyl-N-(2-oxo-2-phenylethyl)}amino-3-tert-butyldimethylsilyloxybutyramide (Reference compound No. 48-10)

IR(Film,cm$^{-1}$)3197,3089,1674,1435

(2RS)-2-{N-Acetyl-N-(2-oxo-2-phenylethyl)}amino-3-methoxypropionamide (Reference compound No. 48-11)

(2RS)-2-{N-Acetyl-N-(2-oxo-2-phenylethyl)}amino-4-methoxybutyramide (Reference compound No. 48-12)

IR(Film,cm$^{-1}$)3246,1666,1448

(2RS)-2-{N-Acetyl-N-(2-oxo-2-phenylethyl)}amino-2-phenylacetamide (Reference compound No. 48-13)

mp 174.5–176.5° C.

IR(KBr,cm$^{-1}$)3276,3016,1660,1642,1602,1497

(2RS)-2-{N-Formyl-N-(2-oxo-2-phenylethyl)}aminoisovaleramide (Reference compound No. 48-14)

IR(Film,cm$^{-1}$)3212,2964,1666,1449

(2RS)-2-{N-Isobutyryl-N-(2-oxo-2-phenylethyl)}aminoisovaleramide (Reference compound No. 48-15)

(2R)-2-{N-Isobutyryl-N-(2-oxo-2-phenylethyl)}aminoisovaleramide (Reference compound No. 48-16)

(2RS)-2-{N-(2-Oxo-2-phenylethyl)-N-pivaloyl}aminoisovaleramide (Reference compound No. 48-17)

IR(Film,cm$^{-1}$)3338,2965,2875,1668,1650,1643,1633,1469

(2RS)-2-{N-Cyclohexylcarbonyl-N-(2-oxo-2-phenylethyl)}aminoisovaleramide (Reference compound No. 48-18)

IR(Film,cm$^{-1}$)3260,2931,2854,1664,1449

(2RS)-2-{N-Methoxycarbonyl-N-(2-oxo-2-phenylethyl)}aminoisovaleramide (Reference compound No. 48-19)

mp 133.5–136.0° C.

IR(KBr,cm$^{-1}$)3233,2961,1690,1653,1471

(2RS)-2-{N-Ethoxycarbonyl-N-(2-oxo-2-phenylethyl)}aminoisovaleramide (Reference compound No. 48-20)

IR(Film,cm$^{-1}$)3345,2965,1681,1448

(2R)-2-{N-Methoxyacetyl-N-(2-oxo-2-phenylethyl)}aminoisovaleramide (Reference compound No. 48-21)

$[\alpha]_D^{20}$ −0.8° (c=0.52, methanol)

IR(Film,cm$^{-1}$)3270,2963,2825,1666,1449

(2R)-2-{N-Benzoyl-N-(2-oxo-2-phenylethyl)}aminoisovaleramide (Reference compound No. 48-22)

$[\alpha]_D^{20}$ +12.1° (c=1.0, methanol)

IR(Film,cm$^{-1}$)3349,2964,1667,1494,1448

(2RS)-2-{N-(4-Chlorobenzoyl)-N-(2-oxo-2-phenylethyl)} aminoisovarelamide (Reference compound No. 48-23)

(2RS)-2-{N-(4-Methoxybenzoyl)-N-(2-oxo-2-phenylethyl)}aminoisovaleramide (Reference compound No. 48-24)

(2RS)-2-{N-(4-Nitrobenzoyl)-N-(2-oxo-2-phenylethyl)}aminoisovaleramide (Reference compound No. 48-25)

(2RS)-2-{N-(2-Oxo-2-phenylethyl)-N-(3-phenylpropanoyl)}aminoisovaleramide (Reference compound No. 48-26)

IR(Film,cm$^{-1}$)3338,3062,3027,2963,2874,1662,1496,1450

(2RS)-2-{N-Benzyloxycarbonyl-N-(2-oxo-2-phenylethyl)}aminoisovaleramide (Reference compound No. 48-27)

IR(Film,cm$^{-1}$)3341,2964,1679,1450

(2RS)-2-{N-(2-Oxo-2-phenylethyl)-N-phenoxyacetyl}aminoisovaleramide (Reference compound No. 48-28)

IR(Film,cm$^{-1}$)3339,3064,3012,2965,2874,1666,1599,1496,1449

(2RS)-2-{N-(2-Oxo-2-phenylethyl)-N-(2-thienylcarbonyl)}aminoisovaleramide (Reference compound No. 48-29)

mp 137.0–138.5° C.

IR(KBr,cm$^{-1}$)3266,2964,1662,1616,1522,1448

(2RS)-2-{N-(2-Oxo-2-phenylethyl)-N-(2-pyridylcarbonyl)}aminoisovaleramide (Reference compound No. 48-30)

(2RS)-2-{N-(2-Oxo-2-phenylethyl)-N-(3-pyridylcarbonyl)}aminoisovaleramide (Reference compound No. 48-31)

IR(Film,cm$^{-1}$)3209,2964,1646

(2RS)-2-{N-(2-Oxo-2-phenylethyl)-N-(4-pyridylcarbonyl)}aminoisovaleramide (Reference compound No. 48-32)

IR(Film,cm$^{-1}$)3204,1650,1552,1494,1448

(2RS)-2-{N-Methanesulfonyl-N-(2-oxo-2-phenylethyl)}aminoisovaleramide (Reference compound No. 48-33)

IR(Film,cm$^{-1}$)3212,1659,1448,1292

(2RS)-2-{N-Benzenesulfonyl-N-(2-oxo-2-phenylethyl)}aminoisovaleramide (Reference compound No. 48-34)

(2RS)-2-[N-Acetyl-N-{2-oxo-2-(3,4,5-trimethoxyphenyl)ethyl}]aminoisovaleramide (Reference compound No. 48-35)

IR(Film,cm⁻¹)3305,2965,2837,1667,1591,1506,1463

(2RS)-2-[N-Benzoyl-N-{2-oxo-2-(3,4,5-trimethoxyphenyl)ethyl}]-aminoisovaleramide (Reference compound No. 48-36)

IR(Film,cm⁻¹)3304,3010,2964,2837,1672,1650,1594, 1552,1504,1454

(2RS)-2-[N-Methoxyacetyl-N-{2-oxo-2-(3,4,5-trimethoxyphenyl)-ethyl}]aminoisovaleramide (Reference compound No. 48-37)

IR(Film,cm⁻¹)3304,2964,2830,1666,1591,1552,1504, 1462

(2RS)-2-[N-Acetyl-N-{2-(3,4-dimethoxyphenyl)-2-oxoethyl}]aminoisovaleramide (Reference compound No. 48-38)

IR(Film,cm⁻¹)3325,2964,2839,1684,1636,1596,1516, 1464

(2RS)-2-[N-Benzoyl-N-{2-(3,4-dimethoxyphenyl)-2-oxoethyl}]aminoisovaleramide (Reference compound No. 48-39)

IR(Film,cm⁻¹)3325,3010,2963,2838,1676,1636,1600, 1516,1448

(2RS)-2-[N-{2-(3,4-Dimethoxyphenyl)-2-oxoethyl}-N-methoxyacetyl]-aminoisovaleramide (Reference compound No. 48-40)

IR(Film,cm⁻¹)3326,2964,2936,2836,1670,1596,1516, 1464

(2RS)-2-[N-Benzoyl-N-{2-(3-methoxyphenyl)-2-oxoethyl}]aminoisovaleramide (Reference compound No. 48-41)

(2RS)-2-{N-Methoxyacetyl-N-(2-oxo-2-phenylethyl)}aminoisovaleramide (Reference compound No. 48-42)

(2RS)-2-{N-Benzoyl-N-(2-oxo-2-phenylethyl)}aminoisovaleramide (Reference compound No. 48-43)

(2R)-2-{N-(2-Oxo-2-phenylethyl)-N-(2-pyridylcarbonyl)}aminoisovaleramide (Reference compound No. 48-44)

(2R)-2-{N-(2-Oxo-2-phenylethyl)-N-(3-pyridylcarbonyl)}aminoisovaleramide (Reference compound No. 48-45)

(2R)-2-{N-(2-Oxo-2-phenylethyl)-N-(4-pyridylcarbonyl)}aminoisovaleramide (Reference compound No. 48-46)

IR(Film,cm⁻¹)3204,1650,1552,1494,1448

(2R)-2-[N-Acetyl-N-{2-(3-methoxyphenyl)-2-oxoethyl}]aminoisovaleramide (Reference compound No. 48-47)

Reference Example 49

(3RS)-4-Acetyl-3-isopropyl-2-oxo-6-phenyl-1,2,3,4-tetrahydropyrazine (Reference compound No. 49-1)

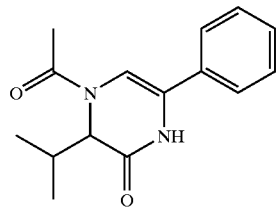

p-Toluenesulfonic acid monohydrate (catalytic amount) is added to a solution of (2RS)-2-{N-acetyl-N-(2-oxo-2-phenylethyl)}aminoisovaleramide (900 mg, Reference compound No. 48-1) in toluene (15 ml), and the mixture is refluxed overnight. The reaction mixture is allowed to stand at room temperature, washed with a saturated aqueous sodium hydrogencarbonate solution and saturated brine successively and dried over anhydrous magnesium sulfate. The reaction mixture is concentrated under reduced pressure, and the resulting residue is purified by silica gel column chromatography to give the titled reference compound (757 mg).

mp 181.5–185.0° C.

IR(KBr,cm⁻¹)3231,1698,1626,1503

The following compounds are obtained by a method similar to Reference Example 49.

(3R)-4-Acetyl-3-isopropyl-2-oxo-6-phenyl-1,2,3,4-tetrahydropyrazine (Reference compound No. 49-2)

mp 152.0–157.5° C.

$[\alpha]_D^{20}$ −483.6° (c=1.0, methanol)

IR(KBr,cm⁻¹)3184,3085,2971,2931,1957,1887,1694, 1644,1468

(3S)-4-Acetyl-3-isopropyl-2-oxo-6-phenyl-1,2,3,4-tetrahydropyrazine (Reference compound No. 49-3)

mp 151.5–155.5° C.

$[\alpha]_D^{20}$ +470.2° (c=0.99, methanol)

IR(KBr,cm⁻¹)3186,3082,2971,2932,1959,1887,1696, 1644,1468,1444

4-Acetyl-2-oxo-6-phenyl-1,2,3,4-tetrahydropyrazine (Reference compound No. 49-4)

4-Acetyl-3,3-dimethyl-2-oxo-6-phenyl-1,2,3,4-tetrahydropyrazine (Reference compound No. 49-5)

mp 160.0–195.0° C.

IR(KBr,cm⁻¹)3190,3088,1694,1674,1509,1478,1460, 1445

(3RS)-4-Acetyl-3-ethyl-2-oxo-6-phenyl-1,2,3,4-tetrahydropyrazine (Reference compound No. 49-6)

mp 181.0–185.0° C.

IR(KBr,cm⁻¹)3184,3088,1874,1652,1446

(3RS)-4-Acetyl-3-{(1RS)-1-methylpropyl}-6-phenyl-1, 2,3,4-tetrahydropyrazine (Reference compound No. 49-7)

mp 176.0–177.0° C.

IR(KBr,cm⁻¹)3200,3088,1686,1648,1452

(3RS)-4-Acetyl-3-isobutyl-2-oxo-6-phenyl-1,2,3,4-tetrahydropyrazine (Reference compound No. 49-8)

mp 165.0–173.5° C.

IR(KBr,cm⁻¹)3196,3088,1689,1674,1649,1470

(3RS)-4-Acetyl-3-cyclohexyl-2-oxo-6-phenyl-1,2,3,4-tetrahydropyrazine (Reference compound No. 49-9)

mp 226.5–228.5° C.

IR(KBr,cm⁻¹)3195,3088,1679,1647,1504,1470,1449

(3RS)-4-Acetyl-3-{(1RS)-1-tert-butyldimethylsilyloxyethyl}-2-oxo-6-phenyl-1,2,3,4-tetrahydropyrazine (Reference compound No. 49-10)

IR(Film,cm⁻¹)3222,3109,1683,1463,1446

(3RS)-4-Acetyl-3-methoxymethyl-2-oxo-6-phenyl-1,2,3, 4-tetrahydropyrazine (Reference compound No. 49-11)

IR(Film,cm⁻¹)3230,3110,1684,1654,1558,1540,1447

(3RS)-4-Acetyl-3-(2-methoxyethyl)-2-oxo-6-phenyl-1,2, 3,4-tetrahydropyrazine (Reference compound No. 49-12)

IR(Film,cm⁻¹)3223,3109,1682,1651,1446

(3RS)-4-Acetyl-3,6-diphenyl-2-oxo-1,2,3,4-tetrahydropyrazine (Reference compound No. 49-13)

mp 180° C.

IR(KBr,cm⁻¹)3196,3095,1683,1668,1656,1467,1448

(3RS)-4-Formyl-3-isopropyl-2-oxo-6-phenyl-1,2,3,4-tetrahydropyrazine (Reference compound No. 49-14)

IR(Film,cm⁻¹)3229,3102,2967,1680,1643

(3RS)-4-Isobutyryl-3-isopropyl-2-oxo-6-phenyl-1,2,3,4-tetrahydropyrazine (Reference compound No. 49-15)

IR(KBr,cm$^{-1}$)3219,3112,1680,1642,1468

(3R)-4-Isobutyryl-3-isopropyl-2-oxo-6-phenyl-1,2,3,4-tetrahydropyrazine (Reference compound No. 49-16)

$[\alpha]_D^{20}$ −401.6° (c=0.51, methanol)

IR(Film,cm$^{-1}$)3218,3104,1682,1467,1446

(3RS)-3-Isopropyl-2-oxo-6-phenyl-4-pivaloyl-1,2,3,4-tetrahydropyrazine (Reference compound No. 49-17)

mp 158.3–167.3° C.

IR(KBr,cm$^{-1}$)3191,3087,2970,2932,1679,1639,1473

(3RS)-4-Cyclohexylcarbonyl-3-isopropyl-2-oxo-6-phenyl-1,2,3,4-tetrahydropyrazine (Reference compound No. 49-18)

mp 209.1–211.4° C.

IR(KBr,cm$^{-1}$)3212,3110,2924,2859,1676,1643,1601,1473,1446

(3RS)-3-Isopropyl-4-methoxycarbonyl-2-oxo-6-phenyl-1,2,3,4-tetrahydropyrazine (Reference compound No. 49-19)

mp 117.5–127.5° C.

IR(KBr,cm$^{-1}$)3188,2962,1725,1670,1443

(3RS)-4-Ethoxycarbonyl-3-isopropyl-2-oxo-6-phenyl-1,2,3,4-tetrahydropyrazine (Reference compound No. 49-20)

mp 106.5–108.5° C.

IR(KBr,cm$^{-1}$)3192,3088,2961,2933,1719,1673,1479

(3R)-3-Isopropyl-4-methoxyacetyl-2-oxo-6-phenyl-1,2,3,4-tetrahydropyrazine (Reference compound No. 49-21)

$[\alpha]_D^{20}$ −379.3° (c=1.3, methanol)

IR(Film,cm$^{-1}$)3230,3109,2965,2932,2823,1686,1655,1601,1465,1447

(3R)-4-Benzoyl-3-isopropyl-2-oxo-6-phenyl-1,2,3,4-tetrahydropyrazine (Reference compound No. 49-22)

$[\alpha]_D^{20}$ −430.2° (c=1.0, methanol)

IR(Film,cm$^{-1}$)3216,3102,2966,1683,1642,1600,1578,1464,1447

(3RS)-4-(4-Chlorobenzoyl)-3-isopropyl-2-oxo-6-phenyl-1,2,3,4-tetrahydropyrazine (Reference compound No. 49-23)

mp 175.0–186.0° C.

IR(KBr,cm$^{-1}$)3852,1680,1646,1590

(3RS)-3-Isopropyl-4-(4-methoxybenzoyl)-2-oxo-6-phenyl-1,2,3,4-tetrahydropyrazine (Reference compound No. 49-24)

mp 202.1–206.6° C.

IR(KBr,cm$^{-1}$)3855,1676,1643,1601

(3RS)-3-Isopropyl-4-(4-nitrobenzoyl)-2-oxo-6-phenyl-1,2,3,4-tetrahydropyrazine (Reference compound No. 49-25)

mp 216.4–221.0° C.

IR(KBr,cm$^{-1}$)1683,1627,1603,1522

(3RS)-3-Isopropyl-2-oxo-6-phenyl-4-(3-phenylpropanoyl)-1,2,3,4-tetrahydropyrazine (Reference compound No. 49-26)

IR(Film,cm$^{-1}$)3219,3103,3026,2964,1932,1684,1651,1602

(3RS)-4-Benzyloxycarbonyl-3-isopropyl-2-oxo-6-phenyl-1,2,3,4-tetrahydropyrazine (Reference compound No. 49-27)

mp 122.0–124.0° C.

IR(KBr,cm$^{-1}$)3218,3104,2961,1679,1498

(3RS)-3-Isopropyl-2-oxo-4-phenoxyacetyl-6-phenyl-1,2,3,4-tetrahydropyrazine (Reference compound No. 49-28)

mp 166.2–171.1° C.

IR(KBr,cm$^{-1}$)3204,3101,2963,1684,1652,1596,1494

(3RS)-3-Isopropyl-2-oxo-6-phenyl-4-(2-thienylcarbonyl)-1,2,3,4-tetrahydropyrazine (Reference compound No. 49-29)

mp 139.5–155.0° C.

IR(KBr,cm$^{-1}$)3211,1674,1636

(3RS)-3-Isopropyl-2-oxo-6-phenyl-4-(2-pyridylcarbonyl)-1,2,3,4-tetrahydropyrazine (Reference compound No. 49-30)

mp 195.0–196.0° C.

IR(KBr,cm$^{-1}$)3300–2000,1697,1643

(3RS)-3-Isopropyl-2-oxo-6-phenyl-4-(3-pyridylcarbonyl)-1,2,3,4-tetrahydropyrazine (Reference compound No. 49-31)

mp 170° C.

IR(KBr,cm$^{-1}$)32 10,3104,2985,2936,1738,1679,1644,1586,1503,1464

(3RS)-3-Isopropyl-2-oxo-6-phenyl-4-(4-pyridylcarbonyl)-1,2,3,4-tetrahydropyrazine (Reference compound No. 49-32)

mp 199.0–202.5° C.

IR(KBr,cm$^{-1}$)3230,3109,3050,2971,1684,1645,1597,1552,1496,1460

(3RS)-3-Isopropyl-4-methanesulfonyl-2-oxo-6-phenyl-1,2,3,4-tetrahydropyrazine (Reference compound No. 49-33)

(3RS)-4-Benzenesulfonyl-3-isopropyl-2-oxo-6-phenyl-1,2,3,4-tetrahydropyrazine (Reference compound No. 49-34)

(3RS)-4-Acetyl-3-isopropyl-2-oxo-6-(3,4,5-trimethoxyphenyl)-1,2,3,4-tetrahydropyrazine (Reference compound No. 49-35)

mp 197.4–200.4° C.

IR(KBr,cm$^{-1}$)3227,3110,2965,2829,1678,1652,1585,1516,1466

(3RS)-4-Benzoyl-3-isopropyl-2-oxo-6-(3,4,5-trimethoxyphenyl)-1,2,3,4-tetrahydropyrazine (Reference compound No. 49-36)

IR(Film,cm$^{-1}$)3219,3102,3011,2965,2936,2840,1683,1644,1583,1514,1466

(3RS)-3-Isopropyl-4-methoxyacetyl-2-oxo-6-(3,4,5-trimethoxyphenyl)-1,2,3,4-tetrahydropyrazine (Reference compound No. 49-37)

mp 146.6–149.7° C.

IR(KBr,cm$^{-1}$)3208,3094,2971,2874,2824,1700,1678,1662,1583,1512,1467

(3RS)-4-Acetyl-6-(3,4-dimethoxyphenyl)-3-isopropyl-2-oxo-1,2,3,4-tetrahydropyrazine (Reference compound No. 49-38)

IR(Film,cm$^{-1}$)3221,3105,3011,2965,2935,2838,1683,1650,1522,1466

(3RS)-4-Benzoyl-6-(3,4-dimethoxyphenyl)-3-isopropyl-2-oxo-1,2,3,4-tetrahydropyrazine (Reference compound No. 49-39)

mp 135.0° C.

IR(KBr,cm$^{-1}$)3228,3109,2963,2872,1679,1643,1599,1534,1490,1466,1442

(3RS)-6-(3,4-Dimethoxyphenyl)-3-isopropyl-4-methoxyacetyl-2-oxo-1,2,3,4-tetrahydropyrazine (Reference compound No. 49-40)

mp 137.0–140.2° C.

IR(KBr,cm$^{-1}$)3209,3096,2963,2831,1674,1648,1586, 1526,1470

(3RS)-4-Benzoyl-3-isopropyl-6-(3-methoxyphenyl)-2-oxo-1,2,3,4-tetrahydropyrazine (Reference compound No. 49-41)

(3RS)-3-Isopropyl-4-methoxyacetyl-2-oxo-6-phenyl-1,2,3,4-tetrahydropyrazine (Reference compound No. 49-42)

(3RS)-4-Benzoyl-3-isopropyl-2-oxo-6-phenyl-1,2,3,4-tetrahydropyrazine (Reference compound No. 49-43)

(3R)-3-Isopropyl-2-oxo-6-phenyl-4-(2-pyridylcarbonyl)-1,2,3,4-tetrahydropyrazine (Reference compound No. 49-44)

(3R)-3-Isopropyl-2-oxo-6-phenyl-4-(3-pyridylcarbonyl)-1,2,3,4-tetrahydropyrazine (Reference compound No. 49-45)

(3R)-3-Isopropyl-2-oxo-6-phenyl-4-(4-pyridylcarbonyl)-1,2,3,4-tetrahydropyrazine (Reference compound No. 49-46)

(3R)-4-Acetyl-3-isopropyl-6-(3-methoxyphenyl)-2-oxo-1,2,3,4-tetrahydropyrazine (Reference compound No. 49-47)

Reference Example 50

Ethyl {(3RS)-4-acetyl-3-isopropyl-2-oxo-6-phenyl-1,2,3,4-tetrahydropyrazin-1-yl}acetate (Reference compound No. 50-1)

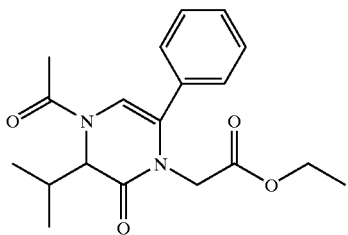

Under ice cooling, 60% sodium hydride (27.9 mg) is added to a solution of (3RS)-4-acetyl-3-isopropyl-2-oxo-6-phenyl-1,2,3,4-tetrahydropyrazine (150 mg, Reference compound No. 49-1) in tetrahydrofuran (1 ml), and the mixture is stirred for 30 minutes. Ethyl bromoacetate (77 µl) is added to the mixture, then the temperature is raised to room temperature, and the whole is stirred for one hour. The reaction mixture is diluted with ethyl acetate, and a saturated aqueous ammonium chloride solution is added thereto. The diluted solution is washed with 0.1 N hydrochloric acid, a saturated aqueous sodium hydrogencarbonate solution and saturated brine successively and dried over anhydrous magnesium sulfate. The diluted solution is concentrated under reduced pressure, and the resulting residue is purified by silica gel column chromatography to give the titled reference compound (195 mg).

mp 96.0–98.0° C.

IR(KBr,cm$^{-1}$)1751,1686,1666,1645,1576

The following compounds are obtained by a method similar to Reference Example 50.

Ethyl {(3R)-4-acetyl-3-isopropyl-2-oxo-6-phenyl-1,2,3,4-tetrahydropyrazin-1-yl}acetate (Reference compound No. 50-2)

mp 115.7–118.0° C.

[α]$_D^{20}$ −186.0° (c=1.0, methanol)

IR(KBr,cm$^{-1}$)3083,2966,2905,2877,1753,1688,1666, 1643

Ethyl {(3S)-4-acetyl-3-isopropyl-2-oxo-6-phenyl-1,2,3, 4-tetrahydropyrazin-1-yl}acetate (Reference compound No. 50-3)

mp 114.5–117.5° C.

[α]$_D^{20}$ +181.7° (c=1.0, methanol)

IR(KBr,cm$^{-1}$)3083,2966,2905,2877,1753,1689,1668, 1644

Methyl (4-acetyl-2-oxo-6-phenyl-1,2,3,4-tetrahydropyrazin-1-yl)-acetate (Reference compound No. 50-4)

IR(KBr,cm$^{-1}$)1751,1680

Ethyl (4-acetyl-3,3-dimethyl-2-oxo-6-phenyl-1,2,3,4-tetrahydropyrazin-1-yl)acetate (Reference compound No. 50-5)

IR(Film,cm$^{-1}$)1749,1681,1549,1446

Ethyl {(3RS)-4-acetyl-3-ethyl-2-oxo-6-phenyl-1,2,3,4-tetrahydropyrazin-1-yl}acetate (Reference compound No. 50-6)

mp 126.0–128.0° C.

IR(KBr,cm$^{-1}$)1745,1733,1669,1687,1648,1574,1480

Ethyl [(3RS)-4-acetyl-3-{(1RS)-1-methylpropyl}-2-oxo-6-phenyl-1,2,3,4-tetrahydropyrazin-1-yl]acetate (Reference compound No. 50-7)

IR(Film,cm$^{-1}$)1749,1682,1446

Methyl {(3RS)-4-acetyl-3-isobutyl-2-oxo-6-phenyl-1,2,3,4-tetrahydropyrazin-1-yl}acetate (Reference compound No. 50-8)

mp 127.5–134.0° C.

IR(KBr,cm$^{-1}$)3105,1745,1684,1668,1647,1401

Ethyl {(3RS)-4-acetyl-3-cyclohexyl-2-oxo-6-phenyl-1,2,3,4-tetrahydropyrazin-1-yl}acetate (Reference compound No. 50-9)

mp 121.0–123.0° C.

IR(Film,cm$^{-1}$)3082,1751,1685,1666,1644,1448

Ethyl [(3RS)-4-acetyl-3-{(1RS)-1-tert-butyldimethylsilyloxyethyl}-2-oxo-6-phenyl-1,2,3,4-tetrahydropyrazin-1-yl]acetate (Reference compound No. 50-10)

IR(KBr,cm$^{-1}$)1750,1691,1472

Ethyl {(3RS)-4-acetyl-3-methoxymethyl-2-oxo-6-phenyl-1,2,3,4-tetrahydropyrazin-1-yl}acetate (Reference compound No. 50-11)

IR(Film,cm$^{-1}$)1749,1684,1446

Ethyl {(3RS)-4-acetyl-3-(2-methoxyethyl)-2-oxo-6-phenyl-1,2,3,4-tetrahydropyrazin-1-yl}acetate (Reference compound No. 50-12)

IR(Film,cm$^{-1}$)1748,1682,1446

Ethyl {(3RS)-4-acetyl-3,6-diphenyl-2-oxo-1,2,3,4-tetrahydropyrazin-1-yl}acetate (Reference compound No. 50-13)

mp 144.7–147.9° C.

IR(Film,cm$^{-1}$)3086,3054,1740,1694,1678,1650,1446

Ethyl {(3RS)-4-formyl-3-isopropyl-2-oxo-6-phenyl-1,2,3,4-tetrahydropyrazin-1-yl}acetate (Reference compound No. 50-14)

IR(Film,cm$^{-1}$)2966,1748,1690,1467,1446

Methyl {(3RS)-4-isobutyryl-3-isopropyl-2-oxo-6-phenyl-1,2,3,4-tetrahydropyrazin-1-yl}acetate (Reference compound No. 50-15)

IR(Film,cm$^{-1}$)1755,1685,1652

Ethyl {(3R)-4-isobutyryl-3-isopropyl-2-oxo-6-phenyl-1,2,3,4-tetrahydropyrazin-1-yl}acetate (Reference compound No. 50-16)

mp 69.5–74.0° C.

[α]$_D^{20}$ −165.5° (c=0.52, methanol)

IR(KBr,cm$^{-1}$)1755,1684,1455

Ethyl {(3RS)-3-isopropyl-2-oxo-6-phenyl-4-pivaloyl-1,2,3,4-tetrahydropyrazin-1-yl}acetate (Reference compound No. 50-17)

IR(Film,cm$^{-1}$)2968,2935,2874,1751,1691,1667,1642

Ethyl {(3RS)-4-cyclohexylcarbonyl-3-isopropyl-2-oxo-6-phenyl-1,2,3,4-tetrahydropyrazin-1-yl}acetate (Reference compound No. 50-18)

mp 125.6–128.6° C.

IR(KBr,cm$^{-1}$)2934,2861,1749,1686,1667,1645,1470,1450

Methyl {(3RS)-3-isopropyl-4-methoxycarbonyl-2-oxo-6-phenyl-1,2,3,4-tetrahydropyrazin-1-yl}acetate (Reference compound No. 50-19)

IR(Film,cm$^{-1}$)2960,1755,1720,1692,1445

Methyl {(3RS)-4-ethoxycarbonyl-3-isopropyl-2-oxo-6-phenyl-1,2,3,4-tetrahydropyrazin-1-yl}acetate (Reference compound No. 50-20)

IR(File,cm$^{-1}$)2964,1755,1714,1693

Ethyl {(3R)-3-isopropyl-4-methoxyacetyl-2-oxo-6-phenyl-1,2,3,4-tetrahydropyrazin-1-yl}acetate (Reference compound No. 50-21)

[α]$_D^{20}$ −150.1° (c=1.0, methanol)

IR(KBr,cm$^{-1}$)2965,2824,1749,1690,1657

Ethyl {(3R)-4-benzoyl-3-isopropyl-2-oxo-6-phenyl-1,2,3,4-tetrahydropyrazin-1-yl}acetate (Reference compound No. 50-22)

mp 110.0–116.8° C.

[α]$_D^{20}$ −211.5° (c=1.0, methanol)

IR(KBr,cm$^{-1}$)3108,3059,3030,2968,1747,1672,1647,1600,1579,1492

Methyl {(3RS)-4-(4-chlorobenzoyl)-3-isopropyl-2-oxo-6-phenyl-1,2,3,4-tetrahydropyrazin-1-yl}acetate (Reference compound No. 50-23)

mp 125.5–128.0° C.

IR(KBr,cm$^{-1}$)1753,1685,1636,1590

Methyl {(3RS)-3-isopropyl-4-(4-methoxybenzoyl)-2-oxo-6-phenyl-1,2,3,4-tetrahydropyrazin-1-yl}acetate (Reference compound No. 50-24)

mp 179.6–185.8° C.

IR(KBr,cm$^{-1}$)1744,1683,1651,1630,1607

Methyl {(3RS)-3-isopropyl-4-(4-nitrobenzoyl)-2-oxo-6-phenyl-1,2,3,4-tetrahydropyrazin-1-yl}acetate (Reference compound No. 50-25)

mp 162.0–165.5° C.

IR(KBr,cm$^{-1}$)1760,1688,1638,1600,1524

Ethyl {(3RS)-3-isopropyl-2-oxo-6-phenyl-4-(3-phenylpropanoyl)-1,2,3,4-tetrahydropyrazin-1-yl}acetate (Reference compound No. 50-26)

mp 131.7–134.0° C.

IR(KBr,cm$^{-1}$)3086,3032,2967,2941,1745,1669,1645,1600,1577

Methyl {(3RS)-4-benzyloxycarbonyl-3-isopropyl-2-oxo-6-phenyl-1,2,3,4-tetrahydropyrazin-1-yl}acetate (Reference compound No. 50-27)

IR(Film,cm$^{-1}$)3032,2963,1755,1714,1692,1446

Ethyl {(3RS)-3-isopropyl-2-oxo-4-phenoxyacetyl-6-phenyl-1,2,3,4-tetrahydropyrazin-1-yl}acetate (Reference compound No. 50-28)

mp 133.8–137.3° C.

IR(KBr,cm$^{-1}$)3058,2978,1759,1680,1598,1497

Methyl {(3RS)-3-isopropyl-2-oxo-6-phenyl-4-(2-thienylcarbonyl)-1,2,3,4-tetrahydropyrazin-1-yl}acetate (Reference compound No. 50-29)

IR(Film,cm$^{-1}$)2962,1752,1690,1630,1516

Methyl {(3RS)-3-isopropyl-2-oxo-6-phenyl-4-(2-pyridylcarbonyl)-1,2,3,4-tetrahydropyrazin-1-yl}acetate (Reference compound No. 50-30)

IR(Film,cm$^{-1}$)1753,1688,1600 tert-Butyl {(3RS)-3-isopropyl-2-oxo-6-phenyl-4-(3-pyridylcarbonyl)-1,2,3,4-tetrahydropyrazin-1-yl}acetate (Reference compound No. 50-31)

IR(Film,cm$^{-1}$)2972,2934,2875,1741,1690,1671,1648,1588,1467,1446 tert-Butyl {(3RS)-3-isopropyl-2-oxo-6-phenyl-4-(4-pyridylcarbonyl)-1,2,3,4-tetrahydropyrazin-1-yl}acetate (Reference compound No. 50-32)

IR(Film,cm$^{-1}$)2971,1741,1688,1651,1596,1550,1447

Ethyl {(3RS)-3-isopropyl-4-methanesulfonyl-2-oxo-6-phenyl-1,2,3,4-tetrahydropyrazin-1-yl}acetate (Reference compound No. 50-33)

IR(Film,cm$^{-1}$)2967,2934,2875,1747,1690,1492,1467

Methyl {(3RS)-4-benzenesulfonyl-3-isopropyl-2-oxo-6-phenyl-1,2,3,4-tetrahydropyrazin-1-yl}acetate (Reference compound No. 50-34)

IR(Film,cm$^{-1}$)3062,2968,2875,1749,1691,1468,1449

Ethyl {(3RS)-4-acetyl-3-isopropyl-2-oxo-6-(3,4,5-trimethoxyphenyl)-1,2,3,4-tetrahydropyrazin-1-yl}acetate (Reference compound No. 50-35)

mp 129.8–134.2° C.

IR(KBr,cm$^{-1}$)3083,2962,2887,2838,1738,1692,1668,1587,1509,1458

Ethyl {(3RS)-4-benzoyl-3-isopropyl-2-oxo-6-(3,4,5-trimethoxyphenyl)-1,2,3,4-tetrahydropyrazin-1-yl}acetate (Reference compound No. 50-36)

mp 161.0–165.4° C.

IR(KBr,cm$^{-1}$)3097,2981,2957,2826,1749,1670,1648,1586,1559,1540,1508,1490,1458

Ethyl {(3RS)-3-isopropyl-4-methoxyacetyl-2-oxo-6-(3,4,5-trimethoxyphenyl)-1,2,3,4-tetrahydropyrazin-1-yl}acetate (Reference compound No. 50-37)

IR(Film,cm$^{-1}$)2964,2828,1748,1691,1582,1540,1507,1464

Ethyl {(3RS)-4-acetyl-6-(3,4-dimethoxyphenyl)-3-isopropyl-2-oxo-1,2,3,4-tetrahydropyrazin-1-yl}acetate (Reference compound No. 50-38)

IR(Film,cm$^{-1}$)2965,2937,2838,1748,1682,1653,1603,1582,1517,1465

Ethyl {(3RS)-4-benzoyl-6-(3,4-dimethoxyphenyl)-3-isopropyl-2-oxo-1,2,3,4-tetrahydropyrazin-1-yl}acetate (Reference compound No. 50-39)

mp 147.7–149.8° C.

IR(KBr,cm$^{-1}$)3086,2965,2938,2874,2842,1746,1669,1648,1602,1583,1519,1493,1465,1449

Ethyl {(3RS)-6-(3,4-dimethoxyphenyl)-3-isopropyl-4-methoxyacetyl-2-oxo-1,2,3,4-tetrahydropyrazin-1-yl}acetate (Reference compound No. 50-40)

IR(Film,cm$^{-1}$)2964,2936,2837,1747,1689,1657,1603,1582,1547,1517,1466

Ethyl {(3RS)-4-benzoyl-3-isopropyl-6-(3-methoxyphenyl)-2-oxo-1,2,3,4-tetrahydropyrazin-1-yl}acetate (Reference compound No. 50-41)

IR(KBr,cm$^{-1}$)3083,3057,2962,1755,1667,1643,1600,1496,1226

Ethyl {(3RS)-3-isopropyl-4-methoxyacetyl-2-oxo-6-phenyl-1,2,3,4-tetrahydropyrazin-1-yl}acetate (Reference compound No. 50-42)

Ethyl {(3RS)-4-benzoyl-3-isopropyl-2-oxo-6-phenyl-1,2,3,4-tetrahydropyrazin-1-yl}acetate (Reference compound No. 50-43)

mp 123.0–124.0° C.

IR(KBr,cm$^{-1}$)3103,3059,2957,2890,2870,1752,1672,1645,1492 tert-Butyl {(3R)-3-isopropyl-2-oxo-6-phenyl-4-(2-pyridylcarbonyl)-1,2,3,4-tetrahydropyrazin-1-yl}acetate (Reference compound No. 50-44)

mp 113.9–117.0° C.

IR(KBr,cm$^{-1}$)2971,2930,1753,1691,1669,1640,1439 tert-Butyl {(3R)-3-isopropyl-2-oxo-6-phenyl-4-(3-pyridylcarbonyl)-1,2,3,4-tetrahydropyrazin-1-yl}acetate (Reference compound No. 50-45)

IR(Film,cm$^{-1}$)2972,2930,1742,1690,1674,1649,1387,1230,1155,756,702 tert-Butyl {(3R)-3-isopropyl-2-oxo-6-phenyl-4-(4-pyridylcarbonyl)-1,2,3,4-tetrahydropyrazin-1-yl}acetate (Reference compound No. 50-46)

IR(Film,cm$^{-1}$)1741,1690,1388,1230,1155,756

Ethyl {(3R)-4-acetyl-3-isopropyl-6-(3-methoxyphenyl)-2-oxo-1,2,3,4-tetrahydropyrazin-1-yl}acetate (Reference compound No. 50-47)

$[\alpha]_D^{20}$ −173.2° (c=1.0, methanol)

IR(Film,cm$^{-1}$)1752,1684,1599,1579

Reference Example 51

{(3RS)-4-Acetyl-3-isopropyl-2-oxo-6-phenyl-1,2,3,4-tetrahydropyrazin-1-yl}acetic acid (Reference compound No. 51-1)

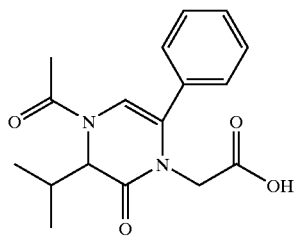

A 4 N aqueous lithium hydroxide solution (0.4 ml) is added to a solution of ethyl {(3RS)-4-acetyl-3-isopropyl-2-oxo-6-phenyl-1,2,3,4-tetrahydropyrazin-1-yl}acetate (185 mg, Reference compound No. 50-1) in ethanol (5 ml), and the mixture is stirred for 35 minutes. To the reaction mixture is added 1 N hydrochloric acid to acidify the system, and the whole is extracted with ethyl acetate. The extract is washed with saturated brine and dried over anhydrous magnesium sulfate. The extract is concentrated under reduced pressure to give the titled reference compound (167 mg).

IR(Film,cm$^{-1}$)3400–2000,1743,1691,1640,1495,1446

The following compounds are obtained by a method similar to Reference Example 51.

{(3R)-4-Acetyl-3-isopropyl-2-oxo-6-phenyl-1,2,3,4-tetrahydropyrazin-1-yl}acetic acid (Reference compound No. 51-2)

$[\alpha]_D^{20}$+186.6° (c=1.0, methanol)

IR(Film,cm$^{-1}$)3450,2968,1725,1681,1617

{(3S)-4-Acetyl-3-isopropyl-2-oxo-6-phenyl-1,2,3,4-tetrahydropyrazin-1-yl}acetic acid (Reference compound No. 51-3) $[\alpha]_D^{20}$−178.9° (c=1.0, methanol)

IR(Film,cm$^{31\ 1}$)2966,2606,1742,1683,1467,1447

(4-Acetyl-2-oxo-6-phenyl-1,2,3,4-tetrahydropyrazin-1-yl)acetic acid (Reference compound No. 51-4)

mp 210° C.

IR(KBr,cm$^{-1}$)3250–2500,1739,1684,1665,1614

(4-Acetyl-3,3-dimethyl-2-oxo-6-phenyl-1,2,3,4-tetrahydropyrazin-1-yl)acetic acid (Reference compound No. 51-5)

IR(Film,cm$^{-1}$)3016,1676,1558,1385

{(3RS)-4-Acetyl-3-ethyl-2-oxo-6-phenyl-1,2,3,4-tetrahydropyrazin-1-yl}acetic acid (Reference compound No. 51-6)

mp 203.5–206.0° C.

IR(KBr,cm$^{-1}$)1748,1674,1624,1450

[(3RS)-4-Acetyl-3-{(1RS)-1-methylpropyl}-2-oxo-6-phenyl-1,2,3,4-tetrahydropyrazin-1-yl]acetic acid (Reference compound No. 51-7)

IR(KBr,cm$^{-1}$)1742,1683,1395

{(3RS)-4-Acetyl-3-isobutyl-2-oxo-6-phenyl-1,2,3,4-tetrahydropyrazin-1-yl}acetic acid (Reference compound No. 51-8)

IR(Film,cm$^{-1}$)1742,1687,1393

{(3RS)-4-Acetyl-3-cyclohexyl-2-oxo-6-phenyl-1,2,3,4-tetrahydropyrazin-1-yl}acetic acid (Reference compound No. 51-9)

IR(KBr,cm$^{-1}$)1743,1688,1448

[(3RS)-4-Acetyl-3-{(1RS)-1-tert-butyldimethylsilyloxyethyl}-2-oxo-6-phenyl-1,2,3,4-tetrahydropyrazin-1-yl]acetic acid (Reference compound No. 51-10)

mp 92.0–101.0° C.

IR(KBr,cm$^{-1}$)1745,1677,1628,1404

{(3RS)-4-Acetyl-3-methoxymethyl-2-oxo-6-phenyl-1,2,3,4-tetrahydropyrazin-1-yl}acetic acid (Reference compound No. 51-11)

IR(Film,cm$^{-1}$)3015,1741,1686,1657,1492,1447

{(3RS)-4-Acetyl-3-(2-methoxyethyl)-2-oxo-6-phenyl-1,2,3,4-tetrahydropyrazin-1-yl}acetic acid (Reference compound No. 51-12)

mp 107.5–118.0° C.

IR(KBr,cm$^{-1}$)1740,1684,1646,1497,1487

{(3RS)-4-Acetyl-3,6-diphenyl-2-oxo-1,2,3,4-tetrahydropyrazin-1-yl}acetic acid (Reference compound No. 51-13)

IR(Film,cm$^{-1}$)3022,1738,1682,1495,1447

{(3RS)-4-Isobutyryl-3-isopropyl-2-oxo-6-phenyl-1,2,3,4-tetrahydropyrazin-1-yl}acetic acid (Reference compound No. 51-14)

IR(KBr,cm$^{-1}$)3500–2500,1748,1690,1470,1448

{(3R)-4-Isobutyryl-3-isopropyl-2-oxo-6-phenyl-1,2,3,4-tetrahydropyrazin-1-yl}acetic acid (Reference compound No. 51-15)

$[\alpha]_D^{20}$−158.8° (c=0.53, methanol)

IR(KBr,cm$^{-1}$)3500–2800,1744,1687

{(3RS)-3-Isopropyl-2-oxo-6-phenyl-4-pivaloyl-1,2,3,4-tetrahydropyrazin-1-yl}acetic acid (Reference compound No. 51-16)

IR(Film,cm$^{-1}$) )2968,1745,1690,1664,1446

{(3RS)-4-Cyclohexylcarbonyl-3-isopropyl-2-oxo-6-phenyl-1,2,3,4-tetrahydropyrazin-1-yl}acetic acid (Reference compound No. 51-17)

IR(Film,cm$^{-1}$)3410,2933,2856,1685,1674,1646,1558, 1540,1506,1496,1447

{(3RS)-3-Isopropyl-4-methoxycarbonyl-2-oxo-6-phenyl-1,2,3,4-tetrahydropyrazin-1-yl}acetic acid (Reference compound No. 51-18)

mp 159.0–162.0° C.

IR(KBr,cm$^{-1}$)2969,1745,1710,1616,1448

{(3RS)-4-Ethoxycarbonyl-3-isopropyl-2-oxo-6-phenyl-1,2,3,4-tetrahydropyrazin-1-yl}acetic acid (Reference compound No. 51-19)

mp 172.3–174.5° C.

IR(KBr,cm$^{-1}$)2983,2938,1751,1711,1661,1629

{(3R)-3-Isopropyl-4-methoxyacetyl-2-oxo-6-phenyl-1,2,3,4-tetrahydropyrazin-1-yl}acetic acid (Reference compound No. 51-20)

$[\alpha]_D^{20}$ –95.8° (c=0.99, methanol)

IR(Film,cm$^{-1}$)3500,2966,1742,1686,1653,1447

{(3R)-4-Benzoyl-3-isopropyl-2-oxo-6-phenyl-1,2,3,4-tetrahydropyrazin-1-yl}acetic acid (Reference compound No. 51-21)

$[\alpha]_D^{20}$ –221.9° (c=1.0, methanol)

IR(KBr,cm$^{-1}$)3087,2960,1746,1670,1605,1572,1492, 1448

{(3RS)-4-(4-Chlorobenzoyl)-3-isopropyl-2-oxo-6-phenyl-1,2,3,4-tetrahydropyrazin-1-yl}acetic acid (Reference compound No. 51-22)

mp 181.5–183.5° C.

IR(KBr,cm$^{-1}$)3150,1751,1692,1668,1626

{(3RS)-3-Isopropyl-4-(4-methoxybenzoyl)-2-oxo-6-phenyl-1,2,3,4-tetrahydropyrazin-1-yl}acetic acid (Reference compound No. 51-23)

mp 186.5–188.0° C.

IR(KBr,cm$^{-1}$)3500–2200,1737,1688,1611

{(3RS)-3-Isopropyl-4-(4-nitrobenzoyl)-2-oxo-6-phenyl-1,2,3,4-tetrahydropyrazin-1-yl}acetic acid (Reference compound No. 51-24)

mp 186.5–188.0° C.

IR(Film,cm$^{-1}$)3500–2200,1737,1688,1611

{(3RS)-3-Isopropyl-2-oxo-6-phenyl-4-(3-phenylpropanoyl)-1,2,3,4-tetrahydropyrazin-1-yl}acetic acid (Reference compound No. 51-25)

IR(Film,cm$^{-1}$)2963,1742,1685,1549,1448

{(3RS)-4-Benzyloxycarbonyl-3-isopropyl-2-oxo-6-phenyl-1,2,3,4-tetrahydropyrazin-1-yl}acetic acid (Reference compound No. 51-26)

mp 182.0–192.0° C.

IR(KBr,cm$^{-1}$)2966,2725,1754,1713,1625,1448

{(3RS)-3-Isopropyl-2-oxo-4-phenoxyacetyl-6-phenyl-1,2,3,4-tetrahydropyrazin-1-yl}acetic acid (Reference compound No. 51-27)

{(3RS)-3-Isopropyl-2-oxo-6-phenyl-4-(2-thienylcarbonyl)-1,2,3,4-tetrahydropyrazin-1-yl}acetic acid (Reference compound No. 51-28)

IR(Film,cm$^{-1}$)2966,1745,1692,1632,1516,1446

{(3RS)-3-Isopropyl-2-oxo-6-phenyl-4-(2-pyridylcarbonyl)-1,2,3,4-tetrahydropyrazin-1-yl}acetic acid (Reference compound No. 51-29)

IR(Film,cm$^{-1}$)3500–2200,1734,1684

{(3RS)-3-Isopropyl-4-methanesulfonyl-2-oxo-6-phenyl-1,2,3,4-tetrahydropyrazin-1-yl}acetic acid (Reference compound No. 51-30)

IR(Film,cm$^{-1}$)3400–2750,1748,1660,1636,1447

{(3RS)-4-Benzenesulfonyl-3-isopropyl-2-oxo-6-phenyl-1,2,3,4-tetrahydropyrazin-1-yl}acetic acid (Reference compound No. 51-31)

IR(Film,cm$^{-1}$)3400–2750,1748,1660,1636,1447

{(3RS)-4-Acetyl-3-isopropyl-2-oxo-6-(3,4,5-trimethoxyphenyl)-1,2,3,4-tetrahydropyrazin-1-yl}acetic acid (Reference compound No. 51-32)

IR(Film,cm$^{-1}$)2966,1688,1583,1507,1463

{(3RS)-4-Benzoyl-3-isopropyl-2-oxo-6-(3,4,5-trimethoxyphenyl)-1,2,3,4-tetrahydropyrazin-1-yl}acetic acid (Reference compound No. 51-33)

mp 240.0° C.

IR(KBr,cm$^{-1}$)3515,2969,1664,1585,1508,1465

{(3RS)-3-Isopropyl-4-methoxyacetyl-2-oxo-6-(3,4,5-trimethoxyphenyl)-1,2,3,4-tetrahydropyrazin-1-yl}acetic acid (Reference compound No. 51-34)

IR(Film,cm$^{-1}$)2968,2831,1688,1649,1584,1503,1464

{(3RS)-4-Acetyl-6-(3,4-dimethoxyphenyl)-3-isopropyl-2-oxo-1,2,3,4-tetrahydropyrazin-1-yl}acetic acid (Reference compound No. 51-35)

IR(Film,cm$^{-1}$)3019,2967,1736,1686,1649,1632,1517, 1465

{(3RS)-4-Benzoyl-6-(3,4-dimethoxyphenyl)-3-isopropyl-2-oxo-1,2,3,4-tetrahydropyrazin-1-yl}acetic acid (Reference compound No. 51-36)

IR(Film,cm$^{-1}$)3018,2965,2840,1742,1689,1666,1644, 1601,1578,1517,1464,1447

{(3RS)-6-(3,4-Dimethoxyphenyl)-3-isopropyl-4-methoxyacetyl-2-oxo-1,2,3,4-tetrahydropyrazin-1-yl}acetic acid (Reference compound No. 51-37)

IR(Film,cm$^{-1}$)2966,2838,1739,1687,1652,1605,1584, 1517,1465

{(3RS)-4-Benzoyl-3-isopropyl-6-(3-methoxyphenyl)-2-oxo-1,2,3,4-tetrahydropyrazin-1-yl}acetic acid (Reference compound No. 51-38)

{(3RS)-3-Isopropyl-4-methoxyacetyl-2-oxo-6-phenyl-1,2,3,4-tetrahydropyrazin-1-yl}acetic acid (Reference compound No. 51-39)

{(3RS)-4-Benzoyl-3-isopropyl-2-oxo-6-phenyl-1,2,3,4-tetrahydropyrazin-1-yl}acetic acid (Reference compound No. 51-40)

{(3R)-3-Isopropyl-2-oxo-6-phenyl-4-(2-pyridylcarbonyl)-1,2,3,4-tetrahydropyrazin-1-yl}acetic acid (Reference compound No. 51-41)

{(3RS)-4-Acetyl-3-isopropyl-6-(3-methoxyphenyl)-2-oxo-1,2,3,4-tetrahydropyrazin-1-yl}acetic acid (Reference compound No. 51-42)

Reference Example 52

DL-N-tert-Butoxycarbonylphenylglycine (Reference compound No. 52-1)

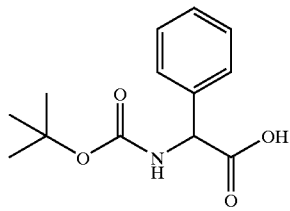

Triethylamine (14.4 ml) and water (50 ml) are added to a suspension of DL-phenylglycine (15.1 g) in tetrahydrofuran (100 ml). Di-tert-butyl dicarbonate (22.9 g) is added to the mixture, and the whole is stirred overnight. Diethyl ether is added to the reaction mixture, and the whole is extracted with a saturated aqueous sodium hydrogencarbonate solution. A 10% aqueous citric acid solution is added to the extract to acidify the system, and the whole is extracted with ethyl acetate. The extract is washed with saturated brine and dried over anhydrous magnesium sulfate. The extract is concentrated under reduced pressure to give the titled reference compound (25 g).

IR(Film,cm$^{-1}$)3300,1720,1657,1497,1455

Reference Example 53

DL-N-tert-Butoxycarbonylcyclohexylglycine (Reference compound No. 53-1)

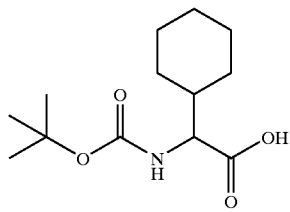

Under a nitrogen atmosphere, 5% rhodium/alumina (3.00 g) is added to a solution of DL-N-tert-butoxycarbonylphenylglycine in ethanol (80 ml). The atmosphere is replaced with pressurized hydrogen (4.0 kgf/cm$^2$) and stirred for ten days. The 5% rhodium/alumina is filtered out. The filtrate is concentrated under reduced pressure, and the residue is purified by silica gel column chromatography to give the titled reference compound (25.0 g).

Reference Example 54

Ethyl (2RS)-2-amino-4-methoxybutyrate hydrochloride (Reference compound No. 54-1)

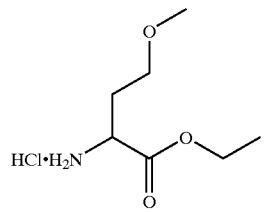

Sodium hydride (1.8 g) is added to a solution of N-(diphenylmethylene)glycine ethyl ester in tetrahydrofuran under ice cooling, then the temperature is raised to room temperature, and the mixture is stirred for one hour. 2-Bromoethyl methyl ether (4.22 ml) is added to the mixture, and the whole is refluxed overnight. The reaction mixture is cooled to room temperature, 0.1 N hydrochloric acid is added thereto, and the whole is stirred for four hours. Ethyl acetate is added to the reaction mixture, and the whole is extracted with 0.1 N hydrochloric acid. The extract is basified with a saturated aqueous sodium hydrogencarbonate solution, and the whole is extracted with ethyl acetate. The extract is washed with saturated brine and dried over anhydrous magnesium sulfate. The extract is concentrated under reduced pressure, a 4 N hydrogen chloride/ethyl acetate solution is added to the resulting residue, and the whole is concentrated under reduced pressure again to give the titled reference compound (2.67 g).

IR(Film,cm$^{-1}$)3418,1746,1595,1504

Reference Example 55

Methyl (2RS,3RS)-3-tert-butyldimethylsilyloxy-2-(2-oxo-2-phenylethyl)aminobutyrate (Reference compound No. 55-1)

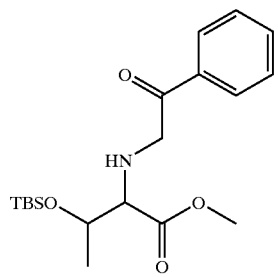

Diisopropylethylamine (3.1 ml) is added to a solution of methyl (2RS,3RS)-3-hydroxy-2-(2-oxo-2-phenylethyl)aminobutyrate (3.70 g, Reference compound No. 46-10) in methylene chloride (35 ml). The mixture is cooled with ice, and tert-butyldimethylsilyl trifluoromethanesulfonate (4.06 ml) is added to the mixture. Then, the temperature is raised to room temperature, and the whole is stirred overnight. Diethyl ether is added to the reaction mixture, and the whole is washed with a saturated aqueous sodium hydrogencarbonate solution and saturated brine successively, and the organic layer is dried over anhydrous magnesium sulfate. The organic layer is concentrated under reduced pressure, and the resulting residue is purified by silica gel column chromatography to give the titled reference compound (4.21 g).

IR(Film,cm$^{-1}$)3342,3062,1742,1693,1598,1580

Reference Example 56

Methyl (2RS)-2-{N-formyl-N-(2-oxo-2-phenylethyl)}aminoisovalerate (Reference compound No. 56-1)

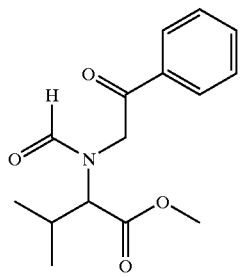

Formic acid (0.46 ml) is added to a suspension of 1,1'-oxalyldiimidazole in acetonitrile under ice cooling, and the mixture is stirred for five minutes. The temperature is raised to room temperature, and the mixture is stirred for 15 minutes. Then, to the mixture is added methyl (2RS)-2-(2-oxo-2-phenylethyl)aminoisovalerate (3.00 g, Reference compound No. 46-1), and the whole is stirred for two hours. The reaction mixture is concentrated under reduced pressure, and the resulting residue is diluted with ethyl acetate. The dilute solution is washed with water, 0.1 N hydrochloric acid and saturated brine successively and dried over anhydrous magnesium sulfate. The solution is concentrated under reduced pressure, and the resulting residue is purified by silica gel column chromatography to give the titled reference compound (2.60 g).

IR(Film,cm$^{-1}$)2965,2875,1740,1703,1677,1598,1582,1449

Reference Example 57

Methyl (2RS)-2-{N-methoxycarbonyl-N-(2-oxo-2-phenylethyl)}amino-isovalerate (Reference compound No. 57-1)

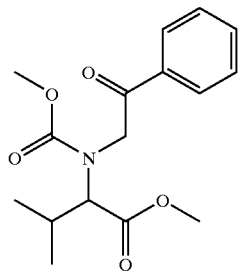

Water (4 ml) and sodium carbonate (1.87 ml) are added to a solution of methyl (2RS)-2-(2-oxo-2-phenylethyl)aminoisovalerate (2.0 g, Reference compound No. 46-1) in ethyl acetate (20 ml). Methyl chloroformate (1.12 ml) is added to the mixture, and the whole is stirred for one day. Ethyl acetate is added to the reaction mixture, the whole is washed with water and saturated brine successively, and the organic layer is dried over anhydrous magnesium sulfate. The organic layer is concentrated under reduced pressure, and the resulting residue is purified by silica gel column chromatography to give the titled reference compound (2.45 g).

IR(Film,cm$^{-1}$)2960,1739,1710,1452

The following compounds are obtained by a method similar to Reference Example 57.

Methyl (2RS)-2-{N-ethoxycarbonyl-N-(2-oxo-2-phenylethyl)}amino-isovalerate (Reference compound No. 57-2)

IR(Film,cm$^{-1}$)2965,1739,1708,1598,1448

Methyl (2RS)-2-{N-benzyloxycarbonyl-N-(2-oxo-2-phenylethyl)}-aminoisovalerate (Reference compound No. 57-3)

IR(Film,cm$^{-1}$)2963,1736,1702,1598,1449

Methyl (2RS)-2-{N-(2-oxo-2-phenylethyl)-N-(2-thienylcarbonyl)}-aminoisovalerate (Reference compound No. 57-4)

IR(Film,cm$^{-1}$)2963,1738,1702,1628,1521

Reference Example 58

Methyl (2RS)-2-(N-methanesulfonyl)aminoisovalerate (Reference compound No. 58-1)

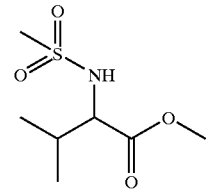

Triethylamine (6.7 ml) is added to a solution of DL-valine methyl ester hydrochloride (3.35 g, Reference compound No. 45-1) in methylene chloride (70 ml). The mixture is cooled with ice, methanesulfonyl chloride (1.9 ml) is added to the mixture, and the whole is stirred overnight. Ethyl acetate is added to the reaction mixture, the whole is washed with 0.1 N hydrochloric acid and saturated brine successively, and the organic layer is dried over anhydrous magnesium sulfate. The organic layer is concentrated under reduced pressure, and the resulting residue is purified by silica gel column chromatography to give the titled reference compound (4.00 g).

IR(Film,cm$^{-1}$)3287,3024,2967,2877,1793

Reference Example 59

Methyl (2RS)-2-{N-methanesulfonyl-N-(2-oxo-2-phenylethyl)}aminoisovalerate (Reference compound No. 59-1)

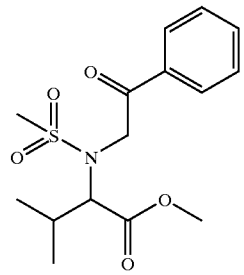

Sodium hydride (574 mg) is added to a solution of methyl (2RS)-2-(N-methanesulfonyl)aminoisovalerate (2.5 g, Reference compound No. 58-1) in dimethylformamide (30 ml) under ice cooling, and the mixture is stirred for 20 minutes. Phenacyl bromide is added to the mixture, and the whole is stirred at 70° C. for two days. The reaction mixture is cooled to room temperature, and ethyl acetate is added to the reaction mixture. The whole is washed with water and saturated brine successively, and the organic layer is dried over anhydrous magnesium sulfate. The organic layer is concentrated under reduced pressure, and the resulting residue is purified by silica gel column chromatography to give the titled reference compound (3.00 g).

IR(Film,cm$^{-1}$)2968,2877,1740,1703,1598,1581,1450

Reference Example 60

{(3RS)-4-Formyl-3-isopropyl-2-oxo-6-phenyl-1,2,3,4-tetrahydropyrazin-1-yl}acetic acid (Reference compound No. 60-1)

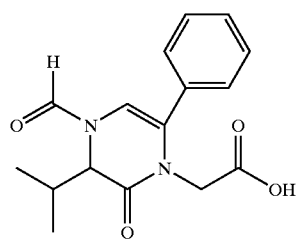

Potassium carbonate (983 mg) and water (6 ml) are added to a solution of ethyl {($^3$RS)-$^4$-formyl-3-isopropyl-2-oxo-6-phenyl-1,2,3,4-tetrahydropyrazin-1-yl}acetate (1.96 g, Reference compound No. 50-1) in ethanol (14 ml), and the mixture is stirred overnight. Ethyl acetate is added to reaction mixture, and the whole is extracted with water. A 10% aqueous citric acid solution is added to the extract to acidify the system, and the whole is extracted with ethyl acetate again. The extract is washed with water and dried over anhydrous magnesium sulfate. The extract is concentrated under reduced pressure to give the titled reference compound (0.90 g).

IR(Film,cm$^{-1}$)2967,2608,1684,1447

Reference Example 61

{(3RS)-3-Isopropyl-2-oxo-6-phenyl-4-(3-pyridylcarbonyl)-1,2,3,4-tetrahydropyrazin-1-yl}acetic acid (Reference compound No. 61-1)

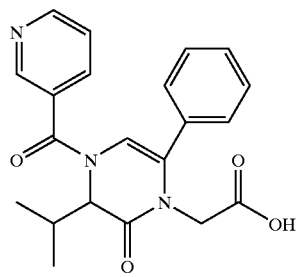

A 4 N hydrogen chloride/ethyl acetate solution (4.00 ml) is added to tert-butyl (3RS)-3-isopropyl-2-oxo-6-phenyl-4-(3-pyridylcarbonyl)-1,2,3,4-tetrahydropyrazin-1-yl}acetate (300 mg, Reference compound No. 50-31), and the mixture is stirred for four hours. The reaction mixture is concentrated under reduced pressure, and the resulting residue is washed with diethyl ether/n-hexane to give the titled reference compound (1.29 g).

mp 230–240° C.

IR(KBr,cm$^{-1}$)3056,2965,2879,1682,1603,1543,1465, 1448

The following compounds are obtained by a method similar to Reference Example 61.

{(3RS)-3-Isopropyl-2-oxo-6-phenyl-4-(4-pyridylcarbonyl)-1,2,3,4-tetrahydropyrazin-1-yl}acetic acid (Reference compound No. 61-2)

IR(KBr,cm$^{-1}$)3087,2965,2879,2726,1733,1678,1655, 1599,1501,1447

{(3R)-3-Isopropyl-2-oxo-6-phenyl-4-(3-pyridylcarbonyl)-1,2,3,4-tetrahydropyrazin-1-yl}acetic acid (Reference compound No. 61-3)

{(3R)-3-Isopropyl-2-oxo-6-phenyl-4-(4-pyridylcarbonyl)-1,2,3,4-tetrahydropyrazin-1-yl}acetic acid (Reference compound No. 61-4)

Reference Example 62

{(3R)-4-Acetyl-6-(3-hydroxyphenyl)-3-isopropyl-2-oxo-1,2,3,4-tetrahydropyrazin-1-yl}acetic acid (Reference compound No. 62-1)

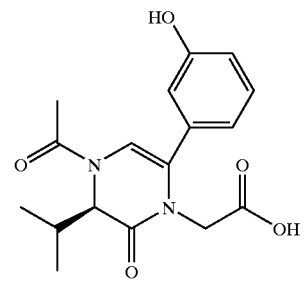

A solution of {(3R)-$^4$-acetyl-3-isopropyl-6-(3-methoxyphenyl)-2-oxo-1,2,3,4-tetrahydropyrazin-1-yl}acetic acid (1.55 g, Reference compound No. 51-42) in methylene chloride (20 ml) is cooled to −78° C. and boron tribromide (10.6 g) is added to the solution. The temperature is raised to room temperature, then the mixture is stirred for three hours, and methylene chloride and ice-cold water are added to the reaction mixture. The whole is extracted with ethyl acetate, and the extract is washed with saturated brine. The extract is dried over anhydrous magnesium sulfate and concentrated under reduced pressure to give the titled reference compound (1.49 g).

$[\alpha]_D^{20}$−167.9° (c=0.22, methanol)

IR(Film,cm$^{-1}$)3500–3000,1734,1651

The following compounds are obtained by a method similar to Reference Example 62.

{(3RS)-4-Acetyl-3-isopropyl-2-oxo-6-(3,4,5-trihydroxyphenyl)-1,2,3,4-tetrahydropyrazin-1-yl}acetic acid (Reference compound No. 62-2)

IR(Film,cm$^{-1}$)3424,1643,1537

{(3RS)-4-Benzoyl-3-isopropyl-2-oxo-6-(3,4,5-trihydroxyphenyl)-1,2,3,4-tetrahydropyrazin-1-yl}acetic acid (Reference compound No. 62-3)

IR(KBr,cm$^{-1}$)3454,1660,1605,1538,1495,1464

{(3RS)-4-Acetyl-6-(3,4-dihydroxyphenyl)-3-isopropyl-2-oxo-1,2,3,4-tetrahydropyrazin-1-yl}acetic acid (Reference compound No. 62-4)

IR(Film,cm$^{-1}$)3425,1636,1522

Reference Example 63

Benzyl {(3R)-4-acetyl-6-(3-benzyloxyphenyl)-3-isopropyl-2-oxo-1,2,3,4-tetrahydropyrazin-1-yl}acetate (Reference compound No. 63-1)

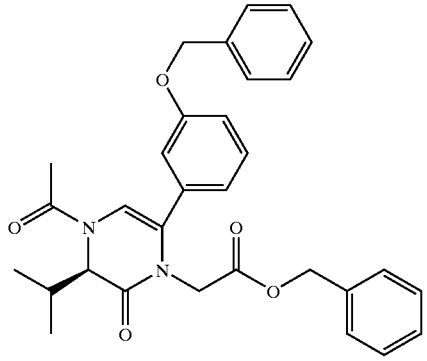

Potassium carbonate (920 mg) and benzyl bromide (0.48 ml) are added to a solution of {(3R)-4-acetyl-6-(3-hydroxyphenyl)-3-isopropyl-2-oxo-1,2,3,4-tetrahydropyrazin-1-yl}acetic acid (221 mg, Reference compound No. 62-1) in acetone (10 ml). Then, the temperature is raised to 50° C., and the mixture is stirred overnight. To the reaction mixture is added 1 N hydrochloric acid to acidify the system, and the whole is extracted with ethyl acetate. The extract is washed with saturated brine and dried over anhydrous magnesium sulfate. The extract is concentrated under reduced pressure, and the resulting residue is purified by silica gel column chromatography to give the titled reference compound (276 mg).

$[\alpha]_D^{20}$ −123.2° (c=1.0, methanol)

IR(Film,cm$^{-1}$)1748,1682

The following compounds are obtained by a method similar to Reference Example 63.

3-Chlorobenzyl [(3R)-4-acetyl-6-{3-(3-chlorobenzyloxy)phenyl}-3-isopropyl-2-oxo-1,2,3,4-tetrahydropyrazin-1-yl]acetate (Reference compound No. 63-2)

$[\alpha]_D^{20}$ −113.9° (c=1.0, methanol)

IR(Film,cm$^{-1}$)1752,1682

3,5-Dichlorobenzyl [(3R)-4-acetyl-6-{3-(3,5-dichlorobenzyloxy)-phenyl}-3-isopropyl-2-oxo-1,2,3,4-tetrahydropyrazin-1-yl]acetate (Reference compound No. 63-3)

$[\alpha]_D^{20}$ −101.9° (c=0.51, methanol)

IR(Film,cm$^{-1}$)1755,1682,1652,1593,1570,1436,1386

Reference Example 64

{(3R)-4-Acetyl-6-(3-benzyloxyphenyl)-3-isopropyl-2-oxo-1,2,3,4-tetrahydropyrazin-1-yl}acetic acid (Reference compound No. 64-1)

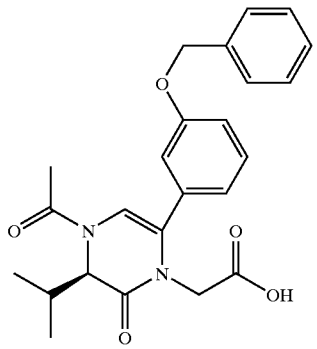

A 4 N aqueous lithium hydroxide solution (1.5 ml) is added to a solution of benzyl {(3R)-4-acetyl-6-(3-benzyloxyphenyl)-3-isopropyl-2-oxo-1,2,3,4-tetrahydropyrazin-1-yl}acetate (276 mg, Reference compound No. 63-1) in ethanol (8 ml)/diethyl ether (2 ml), and the mixture is stirred overnight. To the reaction mixture is added 6 N hydrochloric acid to acidify the system, and the whole is extracted with ethyl acetate. The extract is washed with saturated brine, dried over anhydrous magnesium sulfate and concentrated under reduced pressure to give the titled reference compound (215 mg).

IR(Film,cm$^{-1}$)1740,1689

The following compounds are obtained by a method similar to Reference Example 64.

[(3R)-4-Acetyl-6-{3-(3-chlorobenzyloxy)phenyl}-3-isopropyl-2-oxo-1,2,3,4-tetrahydropyrazin-1-yl]acetic acid (Reference compound No. 64-2)

$[\alpha]_D^{20}$ −127.6° (c=0.95, methanol)

IR(Film,cm$^{-1}$)3500–3000,1740,1687

[(3R)-4-Acetyl-6-{3-(3,5-dichlorobenzyloxy)phenyl}-3-isopropyl-2-oxo-1,2,3,4-tetrahydropyrazin-1-yl]acetic acid (Reference compound No. 64-3)

$[\alpha]_D^{20}$ −123.1° (c=0.48,methanol)

IR(Film,cm$^{-1}$)3500–2400,1739,1688,1389

Reference Example 65

{(3RS)-4-Acetyl-3-isopropyl-2-oxo-6-(3,4,5-triacetoxyphenyl)-1,2,3,4-tetrahydropyrazin-1-yl}acetic acid (Reference compound No. 65-1)

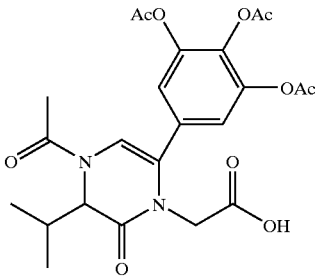

Acetic anhydride is added to a suspension of {(3RS)-4-acetyl-3-isopropyl-2-oxo-6-(3,4,5-trihydroxyphenyl)-1,2,3,4-tetrahydropyrazin-1-yl}acetic acid (630 mg, Reference compound No. 62-2) in acetone (10 ml), and the mixture is stirred for one week. The reaction mixture is concentrated under reduced pressure to give the titled reference compound (790 mg).

IR(Film,cm$^{-1}$)3023,2968,1779,1690,1501

The following compounds are obtained by a method similar to Reference Example 65.

{(3RS)-4-Benzoyl-3-isopropyl-2-oxo-6-(3,4,5-triacetoxyphenyl)-1,2,3,4-tetrahydropyrazin-1-yl}acetic acid (Reference compound No. 65-2)

IR(KBr,cm$^{-1}$)3024,2968,1775,1666,1578,1515,1494, 1447

{(3RS)-4-Acetyl-6-(3,4-diacetoxyphenyl)-3-isopropyl-2-oxo-1,2,3,4-tetrahydropyrazin-1-yl}acetic acid (Reference compound No. 65-3)

EXAMPLES

The following Examples 1 to 21 show examples of the synthesis of the present synthetic intermediates [II] or the present compounds [I] described in detail in the section of "Disclosure of the Invention".

Example 1

Isopropyl (2RS,3S)-3-{(3RS)-4-acetyl-3-isopropyl-2-oxo-6-phenyl-1,2,3,4-tetrahydropyrazin-1-yl}methylcarbonylamino-2-hydroxy-4-phenylbutyrate (Compound No. 1-1)

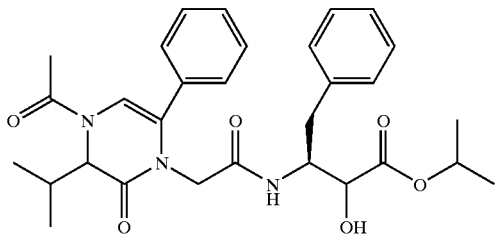

N-Methylmorpholine (67 μl), 1-hydroxybenzotriazole (103 mg) and isopropyl (2RS,3S)-3-amino-2-hydroxy-4-phenylbutyrate (144 mg, Reference compound No. 4-1) are added to a solution of {(3RS)-4-acetyl-3-isopropyl-2-oxo-6-phenyl-1,2,3,4-tetrahydropyrazin-1-yl}acetic acid (160 mg, Reference compound No. 51-1) in methylene chloride (5 ml). The mixture is cooled with ice, 1-(3-dimethylaminopropyl)-3-ethylcarbodiimide hydrochloride (116 mg) is added to the mixture, and the whole is stirred overnight. Ethyl acetate is added to the reaction mixture, the whole is washed with a 0.1 N aqueous sodium hydroxide solution, saturated brine, 0.1 N hydrochloric acid and saturated brine successively, and the organic layer is dried over anhydrous magnesium sulfate. The organic layer is concentrated under reduced pressure, and the resulting residue is purified by silica gel column chromatography to give the titled compound (259 mg).

IR(Film,cm$^{-1}$)3328,1731,1680,1531,1447

The following compounds are obtained by a method similar to Example 1.

Isopropyl (2RS,3S)-3-{(3R)-4-acetyl-3-isopropyl-2-oxo-6-phenyl-1,2,3,4-tetrahydropyrazin-1-yl}methylcarbonylamino-2-hydroxy-4-phenylbutyrate (Compound No. 1-2)

$[\alpha]_D^{20}$ −96.2° (c=1.0, methanol)

IR(Film,cm$^{-1}$)3419,3062,3012,2978,1733,1673,1538, 1496

Isopropyl (2RS,3S)-3-{(3S)-4-acetyl-3-isopropyl-2-oxo-6-phenyl-1,2,3,4-tetrahydropyrazin-1-yl}methylcarbonylamino-2-hydroxy-4-phenylbutyrate (Compound No. 1-3)

$[\alpha]_D^{20}$ +92.7° (c=1.0, methanol)

IR(Film,cm$^{-1}$)3338,3011,2978,1735,1676,1539,1496, 1467,1447

Isopropyl (2RS,3S)-3-{4-acetyl-2-oxo-6-phenyl-1,2,3,4-tetrahydropyrazin-1-yl}methylcarbonylamino-2-hydroxy-4-phenylbutyrate (Compound No. 1-4)

IR(Film,cm$^{-1}$)3325,1732,1678

Isopropyl (2RS,3S)-3-(4-acetyl-3,3-dimethyl-2-oxo-6-phenyl-1,2,3,4-tetrahydropyrazin-1-yl)methylcarbonyl-amino-2-hydroxy-4-phenylbutyrate (Compound No. 1-5)

IR(Film,cm$^{-1}$)3338,3062,1732,1679,1655,1531

Isopropyl (2RS,3S)-3-{(3RS)-4-acetyl-3-ethyl-2-oxo-6-phenyl-1,2,3,4-tetrahydropyrazin-1-yl}methylcarbonyl-amino-2-hydroxy-4-phenylbutyrate (Compound No. 1-6)

IR(Film,cm$^{-1}$)3328,3061,1734,1676,1534,1469,1446

Isopropyl (2RS,3S)-3-[(3RS)-4-acetyl-3-{(1RS)-1-methylpropyl}-2-oxo-6-phenyl-1,2,3,4-tetrahydropyrazin-1-yl]methylcarbonylamino-2-hydroxy-4-phenylbutyrate (Compound No. 1-7)

IR(Film,cm$^{-1}$)3339,1733,1678,1532,1447

Isopropyl (2RS,3S)-3-{(3RS)-4-acetyl-3-isobutyl-2-oxo-6-phenyl-1,2,3,4-tetrahydropyrazin-1-yl}methylcarbonyl-amino-2-hydroxy-4-phenylbutyrate (Compound No. 1-8)

IR(Film,cm$^{-1}$)3337,3062,1732,1680,1646,1535

Isopropyl (2RS,3S)-3-{(3RS)-4-acetyl-3-cyclohexyl-2-oxo-6-phenyl-1,2,3,4-tetrahydropyrazin-1-yl}methylcarbonylamino-2-hydroxy-4-phenylbutyrate (Compound No. 1-9)

IR(Film,cm$^{-1}$)3337,3061,3010,1733,1682,1539,1496, 1447

Isopropyl (2RS,3S)-3-[(3RS)-4-acetyl-3-{(1RS)-1-tert-butyldimethylsilyloxyethyl}-2-oxo-6-phenyl-1,2,3,4-tetrahydropyrazin-1-yl]methylcarbonylamino-2-hydroxy-4-phenylbutyrate (Compound No. 1-10)

IR(Film,cm$^{-1}$)3336,3061,1732,1681,1533,1446,1404

Isopropyl (2RS,3S)-3-{(3RS)-4-acetyl-3-methoxymethyl-2-oxo-6-phenyl-1,2,3,4-tetrahydropyrazin-1-yl}methylcarbonylamino-2-hydroxy-4-phenylbutyrate (Compound No. 1-11)

IR(Film,cm$^{-1}$)3324,1734,1677,1654,1530,1496,1447

Isopropyl (2RS,3S)-3-{(3RS)-4-acetyl-3-(2-methoxyethyl)-2-oxo-6-phenyl-1,2,3,4-tetrahydropyrazin-1-yl}methylcarbonylamino-2-hydroxy-4-phenylbutyrate (Compound No. 1-12)

IR(Film,cm$^{-1}$)3328,3060,1733,1680,1532

Isopropyl (2RS,3S)-3-{(3RS)-4-acetyl-3,6-diphenyl-2-oxo-1,2,3,4-tetrahydropyrazin-1-yl}methylcarbonylamino-2-hydroxy-4-phenylbutyrate (Compound No. 1-13)

IR(Film,cm$^{-1}$)3328,3062,1729,1678,1530,1495,1447

Isopropyl (2RS,3S)-3-{(3RS)-4-formyl-3-isopropyl-2-oxo-6-phenyl-1,2,3,4-tetrahydropyrazin-1-yl}methylcarbonylamino-2-hydroxy-4-phenylbutyrate (Compound No. 1-14)

IR(Film,cm$^{-1}$)3338,3061,2975,1733,1683,1537,1448

Isopropyl (2RS,3S)-2-hydroxy-3-{(3RS)-4-isobutyryl-3-isopropyl-2-oxo-6-phenyl-1,2,3,4-tetrahydropyrazin-1-yl}methylcarbonylamino-4-phenylbutyrate (Compound No. 1-15)

IR(Film,cm$^{-1}$)3338,1730,1682

Isopropyl (2RS,3S)-2-hydroxy-3-{(3R)-4-isobutyryl-3-isopropyl-2-oxo-6-phenyl-1,2,3,4-tetrahydropyrazin-1-yl}methylcarbonylamino-4-phenylbutyrate (Compound No. 1-16)

IR(Film,cm$^{-1}$)3338,1732,1682,1537,1391,1227,1106

Isopropyl (2RS,3S)-2-hydroxy-3-{(3RS)-3-isopropyl-2-oxo-6-phenyl-4-pivaloyl-1,2,3,4-tetrahydropyrazin-1-yl}methylcarbonylamino-4-phenylbutyrate (Compound No. 1-17)

IR(Film,cm$^{-1}$)3341,3061,2974,2935,2875,1730,1682,1637,1532

Isopropyl (2RS,3S)-3-{(3RS)-4-cyclohexylcarbonyl-3-isopropyl-2-oxo-6-phenyl-1,2,3,4-tetrahydropyrazin-1-yl}methylcarbonylamino-2-hydroxy-4-phenylbutyrate (Compound No. 1-18)

IR(Film,cm$^{-1}$)3337,2933,2856,1730,1680,1644,1530,1496,1467,1447

Isopropyl (2RS,3S)-2-hydroxy-3-{(3RS)-3-isopropyl-4-methoxycarbonyl-2-oxo-6-phenyl-1,2,3,4-tetrahydropyrazin-1-yl}-methylcarbonylamino-4-phenylbutyrate (Compound No. 1-19)

Isopropyl (2RS,3S)-3-{(3RS)-4-ethoxycarbonyl-3-isopropyl-2-oxo-6-phenyl-1,2,3,4-tetrahydropyrazin-1-yl}methylcarbonylamino-2-hydroxy-4-phenylbutyrate (Compound No. 1-20)

IR(Film,cm$^{-1}$)3348,2978,1714,1687,1529

Isopropyl (2RS,3S)-2-hydroxy-3-{(3R)-3-isopropyl-4-methoxyacetyl-2-oxo-6-phenyl-1,2,3,4-tetrahydropyrazin-1-yl}methylcarbonylamino-4-phenylbutyrate (Compound No. 1-21)

[α]$_D^{20}$-88.4° (c=1.0, methanol)

IR(Film,cm$^{-1}$)3324,3061,2978,2935,2825,1733,1680,1533,1448

Isopropyl (2RS,3S)-3-{(3R)-4-benzoyl-3-isopropyl-2-oxo-6-phenyl-1,2,3,4-tetrahydropyrazin-1-yl}methylcarbonylamino-2-hydroxy-4-phenylbutyrate (Compound No. 1-22)

[α]$_D^{20}$-128.1° (c=0.97, methanol)

IR(Film,cm$^{-1}$)3339,3061,2969,1732,1668,1640,1577,1537,1494,1447

Isopropyl (2RS,3S)-3-{(3RS)-4-(4-chlorobenzoyl)-3-isopropyl-2-oxo-6-phenyl-1,2,3,4-tetrahydropyrazin-1-yl}methylcarbonylamino-2-hydroxy-4-phenylbutyrate (Compound No. 1-23)

IR(Film,cm$^{-1}$)3338,1732,1682,1596

Isopropyl (2RS,3S)-2-hydroxy-3-{(3RS)-3-isopropyl-4-(4-methoxybenzoyl)-2-oxo-6-phenyl-1,2,3,4-tetrahydropyrazin-1-yl}-methylcarbonylamino-4-phenylbutyrate (Compound No. 1-24)

Isopropyl (2RS,3S)-2-hydroxy-3-{(3RS)-3-isopropyl-4-(4-nitrobenzoyl)-2-oxo-6-phenyl-1,2,3,4-tetrahydropyrazin-1-yl}-methylcarbonylamino-4-phenylbutyrate (Compound No. 1-25)

IR(Film,cm$^{-1}$)3852,1733,1684,1675,1602,1526

Isopropyl (2RS,3S)-2-hydroxy-3-{(3RS)-3-isopropyl-2-oxo-6-phenyl-4-(3-phenylpropanoyl)-1,2,3,4-tetrahydropyrazin-1-yl}methylcarbonyl-)amino-4-phenylbutyrate (Compound No. 1-26)

IR(Film,cm$^{-1}$)3319,3027,2967,1732,1687,1530,1496,1447

Isopropyl (2RS,3S)-3-{(3RS)-4-benzyloxycarbonyl-3-isopropyl-2-oxo-6-phenyl-1,2,3,4-tetrahydropyrazin-1-yl}methylcarbonylamino-2-hydroxy-4-phenylbutyrate (Compound No. 1-27)

IR(Film,cm$^{-1}$)3350,3015,2967,1690,1528

Isopropyl (2RS,3S)-2-hydroxy-3-{(3RS)-3-isopropyl-2-oxo-4-phenoxyacetyl-6-phenyl-1,2,3,4-tetrahydropyrazin-1-yl}methylcarbonyl-amino-4-phenylbutyrate (Compound No. 1-28)

IR(Film,cm$^{-1}$)3317,3061,3027,2974,2932,1730,1681,1650,1600,1496

Isopropyl (2RS,3S)-2-hydroxy-3-{(3RS)-3-isopropyl-2-oxo-6-phenyl-4-(2-thienylcarbonyl)-1,2,3,4-tetrahydropyrazin-1-yl}methylcarbonyl-amino-4-phenylbutyrate (Compound No. 1-29)

IR(Film,cm$^{-1}$)3338,2971,1732,1685,1654,1634,1519

Isopropyl (2RS,3S)-2-hydroxy-3-{(3RS)-3-isopropyl-2-oxo-6-phenyl-4-(2-pyridylcarbonyl)-1,2,3,4-tetrahydropyrazin-1-yl}methylcarbonyl-amino-4-phenylbutyrate (Compound No. 1-30)

IR(Film,cm$^{-1}$)3336,1732,1680,1600,1530

Isopropyl (2RS,3S)-2-hydroxy-3-{(3RS)-3-isopropyl-2-oxo-6-phenyl-4-(3-pyridylcarbonyl)-1,2,3,4-tetrahydropyrazin-1-yl}methylcarbonyl-amino-4-phenylbutyrate (Compound No. 1-31)

IR(Film,cm$^{-1}$)3345,2977,1731,1681,1589,1531,1496,1448

Isopropyl (2RS,3S)-2-hydroxy-3-{(3RS)-3-isopropyl-2-oxo-6-phenyl-4-(4-pyridylcarbonyl)-1,2,3,4-tetrahydropyrazin-1-yl}methylcarbonyl-amino-4-phenylbutyrate (Compound No. 1-32)

IR(Film,cm$^{-1}$)3341,2977,1730,1680,1645,1599,1549,1495,1447

Isopropyl (2RS,3S)-2-hydroxy-3-{(3RS)-3-isopropyl-4-methanesulfonyl-2-oxo-6-phenyl-1,2,3,4-tetrahydropyrazin-1-yl}-methylcarbonylamino-4-phenylbutyrate (Compound No. 1-33)

IR(Film,cm$^{-1}$)3365,3061,3026,2977,2934,2875,1730,1686,1602,1529

Isopropyl (2RS,3S)-3-{(3RS)-4-benzenesulfonyl-3-isopropyl-2-oxo-6-phenyl-1,2,3,4-tetrahydropyrazin-1-yl}methylcarbonylamino-2-hydroxy-4-phenylbutyrate (Compound No. 1-34)

IR(Film,cm$^{-1}$)3358,3027,2978,2934,1727,1682,1525,1496,1467

Isopropyl (2RS,3S)-3-{(3RS)-4-acetyl-3-isopropyl-2-oxo-6-(3,4,5-trimethoxyphenyl)-1,2,3,4-tetrahydropyrazin-1-yl}methylcarbonyl-amino-2-hydroxy-4-phenylbutyrate (Compound No. 1-35)

IR(Film,cm$^{-1}$)3338,2969,2939,2838,1734,1681,1583,1507,1456

Isopropyl (2RS,3S)-3-{(3RS)-4-benzoyl-3-isopropyl-2-oxo-6-(3,4,5-trimethoxyphenyl)-1,2,3,4-tetrahydropyrazin-1-yl}methylcarbonyl-amino-2-hydroxy-4-phenylbutyrate (Compound No. 1-36)

IR(Film,cm$^{-1}$)3338,2969,2835,1732,1684,1582,1507,1454

Isopropyl (2RS,3S)-2-hydroxy-3-{(3RS)-3-isopropyl-4-methoxyacetyl-2-oxo-6-(3,4,5-trimethoxyphenyl)-1,2,3,4-tetrahydropyrazin-1-yl}-methylcarbonylamino-4-phenylbutyrate (Compound No. 1-37)

IR(Film,cm$^{-1}$)3339,2968,2938,2828,1734,1682,1583,1507,1456

Isopropyl (2RS,3S)-3-{(3RS)-4-acetyl-6-(3,4-dimethoxyphenyl)-3-isopropyl-2-oxo-1,2,3,4-tetrahydropyrazin-1-yl}methylcarbonylamino-2-hydroxy-4-phenylbutyrate (Compound No. 1-38)

IR(Film,cm⁻¹)3343,2968,2839,1732,1678,1516,1464

Isopropyl (2RS,3S)-3-{(3RS)-4-benzoyl-6-(3,4-dimethoxyphenyl)-3-isopropyl-2-oxo-1,2,3,4-tetrahydropyrazin-1-yl}methylcarbonylamino-2-hydroxy-4-phenylbutyrate (Compound No. 1-39)

IR(Film,cm⁻¹)3345,3013,2967,2936,2838,1731,1684,1580,1517,1450

Isopropyl (2RS,3S)-3-{(3RS)-6-(3,4-dimethoxyphenyl)-3-isopropyl-4-methoxyacetyl-2-oxo-1,2,3,4-tetrahydropyrazin-1-yl}methylcarbonyl-amino-2-hydroxy-4-phenylbutyrate (Compound No. 1-40)

IR(Film,cm⁻¹)3416,2967,2936,2838,1732,1678,1583,1517,1466

Isopropyl (2RS,3S)-3-{(3RS)-4-benzoyl-3-isopropyl-6-(3-methoxyphenyl)-2-oxo-1,2,3,4-tetrahydropyrazin-1-yl}methylcarbonyl-amino-2-hydroxy-4-phenylbutyrate (Compound No. 1-41)

Isopropyl (2RS,3S)-3-{(3RS)-4-acetyl-3-isopropyl-2-oxo-6-(3,4,5-triacetoxyphenyl)-1,2,3,4-tetrahydropyrazin-1-yl}methylcarbonyl-amino-2-hydroxy-4-phenylbutyrate (Compound No. 1-42)

IR(Film,cm⁻¹)3339,2981,2936,1781,1738,1680,1564,1530,1500

Isopropyl (2RS,3S)-3-{(3RS)-4-benzoyl-3-isopropyl-2-oxo-6-(3,4,5-triacetoxyphenyl)-1,2,3,4-tetrahydropyrazin-1-yl}methylcarbonyl-amino-2-hydroxy-4-phenylbutyrate (Compound No. 1-43)

IR(Film,cm⁻¹)3350,2981,2937,1778,1732,1666,1538,1446

Isopropyl (2RS,3S)-3-{(3RS)-4-acetyl-6-(3,4-diacetoxyphenyl)-3-isopropyl-2-oxo-1,2,3,4-tetrahydropyrazin-1-yl}methylcarbonylamino-2-hydroxy-4-phenylbutyrate (Compound No. 1-44)

IR(Film,cm⁻¹)3323,2979,1727,1668,1643,1578,1528

Isopropyl (2RS,3S)-3-{(3R)-4-acetyl-6-(3-benzyloxyphenyl)-3-isopropyl-2-oxo-1,2,3,4-tetrahydropyrazin-1-yl}methylcarbonylamino-2-hydroxy-4-phenylbutyrate (Compound No. 1-45)

Isopropyl (2RS,3S)-3-[(3R)-4-acetyl-6-{3-(3-chlorobenzyloxy)-phenyl}-3-isopropyl-2-oxo-1,2,3,4-tetrahydropyrazin-1-yl]methylcarbonyl-amino-2-hydroxy-4-phenylbutyrate (Compound No. 1-46)

IR(Film,cm⁻¹)3838,1732,1677,1388

Isopropyl (2RS,3S)-3-[(3R)-4-acetyl-6-{3-(3,5-dichlorobenzyloxy)-phenyl}-3-isopropyl-2-oxo-1,2,3,4-tetrahydropyrazin-1-yl]methylcarbonyl-amino-2-hydroxy-4-phenylbutyrate (Compound No. 1-47)

IR(Film,cm⁻¹)3338,1733,1680,1432,1388,1280,1213

Methyl (2S)-2-{(3RS)-4-acetyl-3-isopropyl-2-oxo-6-phenyl-1,2,3,4-tetrahydropyrazin-1-yl}methylcarbonyl-amino-3-phenylpropionate (Compound No. 1-48)

IR(Film,cm⁻¹)3316,3062,3012,2964,1745,1682,1650,1532,1446,1388

(2S)-2-{(3R)-4-Isobutyryl-3-isopropyl-2-oxo-6-phenyl-1,2,3,4-tetrahydropyrazin-1-yl}methylcarbonylamino-1,3-diphenylpropanone (Compound No. 1-49)

N¹-Methoxy-(2S)-2-{(3RS)-4-acetyl-3-isopropyl-2-oxo-6-phenyl-1,2,3,4-tetrahydropyrazin-1-yl}methylcarbonyl-amino-3-phenylpropionamide (Compound No. 1-50)

IR(Film,cm⁻¹)3280,1671

N¹-Methoxy-N¹-methyl-(2S)-2-{(3RS)-4-acetyl-3-isopropyl-2-oxo-phenyl-1,2,3,4-tetrahydropyrazin-1-yl}methylcarbonylamino-3-phenylpropionamide (Compound No. 1-51)

IR(Film,cm⁻¹)3212,1674,1388

(2S)-2-{(3RS)-3-Isopropyl-2-oxo-4-methoxyacetyl-6-phenyl-1,2,3,4-tetrahydropyrazin-1-yl}methylcarbonyl-amino-1-morpholino-1-oxo-3-phenylpropane (Compound No. 1-52)

IR(Film,cm⁻¹)3306,3060,3006,2965,2929,2861,1682,1644,1538

(2S)-2-{(3RS)-3-Isopropyl-2-oxo-4-methoxyacetyl-6-phenyl-1,2,3,4-tetrahydropyrazin-1-yl}methylcarbonyl-amino-1-oxo-3-phenyl-1-piperidinopropane (Compound No. 1-53)

IR(Film,cm⁻¹)3294,3004,2936,2857,1684,1628,1540,1496,1447,1388

(2S)-1-{(2S)-2-Carbamoylpyrrolidin-1-yl}-2-{(3RS)-3-isopropyl-4-methoxyacetyl-2-oxo-6-phenyl-1,2,3,4-tetrahydropyrazin-1-yl}-methylcarbonylamino-1-oxo-3-phenylpropane (Compound No. 1-54)

IR(Film,cm⁻¹)3306,1682,1630,1447,754

(2S)-1-(4-tert-Butoxycarbonylpiperazin-1-yl)-2-{(3RS)-3-isopropyl-4-methoxyacetyl-2-oxo-6-phenyl-1,2,3,4-tetrahydropyrazin-1-yl}-methylcarbonylamino-1-oxo-3-phenylpropane (Compound No. 1-55)

IR(Film,cm⁻¹)3306,3007,2973,2931,1682,1644,1447,1416,1367

Example 2

Isopropyl (3S)-3-{(3RS)-4-acetyl-3-isopropyl-2-oxo-6-phenyl-1,2,3,4-tetrahydropyrazin-1-yl}methylcarbonylamino-2-oxo-4-phenylbutyrate (Compound No. 2-1)

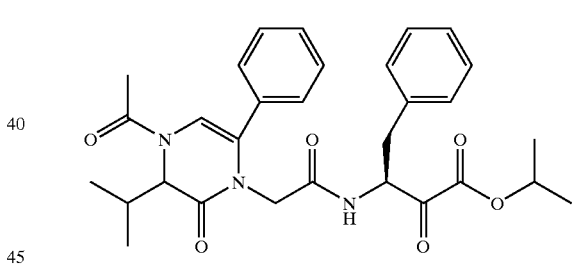

Acetic anhydride (2.0 ml) is added to a solution of isopropyl (2RS,3S)-3-{(3RS)-4-acetyl-3-isopropyl-2-oxo-6-phenyl-1,2,3,4-tetrahydropyrazin-1-yl}methylcarbonyl-amino-2-hydroxy-4-phenylbutyrate (220 mg, Compound No. 1-1) in dimethyl sulfoxide (2.0 ml), and the mixture is stirred overnight. Water is added to the reaction mixture, and the whole is stirred for 1.5 hours. Water and sodium hydrogencarbonate is added to the reaction mixture to basify the system, and the whole is extracted with ethyl acetate. The extract is washed with saturated brine and dried over anhydrous magnesium sulfate. The extract is concentrated under reduced pressure, and the resulting residue is purified by silica gel column chromatography to give the titled compound (188 mg).

IR(Film,cm⁻¹)3306,1725,1677,1525,1446

The following compounds are obtained by a method similar to Example 2.

Isopropyl (3S)-3-{(3R)-4-acetyl-3-isopropyl-2-oxo-6-phenyl-1,2,3,4-tetrahydropyrazin-1-yl}methylcarbonyl-amino-2-oxo-4-phenylbutyrate (Compound No. 2-2)

$[\alpha]_D^{20}$ −86.7° (c=1.0, methanol)

IR(Film,cm$^{-1}$)3306,2978,2935,1725,1679,1529,1446

Isopropyl (3S)-3-{(3S)-4-acetyl-3-isopropyl-2-oxo-6-phenyl-1,2,3,4-tetrahydropyrazin-1-yl}methylcarbonylamino-2-oxo-4-phenylbutyrate (Compound No. 2-3)

$[\alpha]_D^{20}$ +86.5° (c=0.99, methanol)

IR(Film,cm$^{-1}$)3306,2978,2935,1725,1679,1529,1446

Isopropyl (3S)-3-{4-acetyl-2-oxo-6-phenyl-1,2,3,4-tetrahydropyrazin-1-yl}methylcarbonylamino-2-oxo-4-phenylbutyrate (Compound No. 2-4)

IR(Film,cm$^{-1}$)3854,1725,1679,1536

Isopropyl (3S)-3-(4-acetyl-3,3-dimethyl-2-oxo-6-phenyl-1,2,3,4-tetrahydropyrazin-1-yl)methylcarbonylamino-2-oxo-4-phenylbutyrate (Compound No. 2-5)

IR(Film,cm$^{-1}$)3302,1731,1670,1539

Isopropyl (3S)-3-{(3RS)-4-acetyl-3-ethyl-2-oxo-6-phenyl-1,2,3,4-tetrahydropyrazin-1-yl}methylcarbonylamino-2-oxo-4-phenylbutyrate (Compound No. 2-6)

IR(Film,cm$^{-1}$)3306,1726,1680,1649,1530,1446

Isopropyl (3S)-3-[(3RS)-4-acetyl-3-{(1RS)-1-methylpropyl}-2-oxo-6-phenyl-1,2,3,4-tetrahydropyrazin-1-yl]methylcarbonylamino-2-oxo-4-phenylbutyrate (Compound No. 2-7)

IR(Film,cm$^{-1}$)3305,1726,1682,1540,1497,1447

Isopropyl (3S)-3-{(3RS)-4-acetyl-3-isobutyl-2-oxo-6-phenyl-1,2,3,4-tetrahydropyrazin-1-yl}methylcarbonylamino-2-oxo-4-phenylbutyrate (Compound No. 2-8)

IR(Film,cm$^{-1}$)3306,1743,1727,1681,1646,1528

Isopropyl (3S)-3-{(3RS)-4-acetyl-3-cyclohexyl-2-oxo-6-phenyl-1,2,3,4-tetrahydropyrazin-1-yl}methylcarbonylamino-2-oxo-4-phenylbutyrate (Compound No. 2-9)

IR(Film,cm$^{-1}$)3315,3061,1727,1679,1530,1448

Isopropyl (3S)-3-[(3RS)-4-acetyl-3-{(1RS)-1-tert-butyldimethylsilyl-oxyethly}-2-oxo-6-phenyl-1,2,3,4-tetrahydropyrazin-1-yl]-methylcarbonylamino-2-oxo-4-phenylbutyrate (Compound No. 2-10)

IR(Film,cm$^{-1}$)3305,1725,1686,1524,1472,1446,1404

Isopropyl (3S)-3-{(3RS)-4-acetyl-3-methoxymethyl-2-oxo-6-phenyl-1,2,3,4-tetrahydropyrazin-1-yl}methylcarbonylamino-2-oxo-4-phenylbutyrate (Compound No. 2-11)

IR(Film,cm$^{-1}$)3296,2830,1723,1682,1651,1520,1496,1446

Isopropyl (3S)-3-{(3RS)-4-acetyl-3-(2-methoxyethyl)-2-oxo-6-phenyl-1,2,3,4-tetrahydropyrazin-1-yl}methylcarbonylamino-2-oxo-4-phenylbutyrate (Compound No. 2-12)

IR(Film,cm$^{-1}$)3308,1727,1680,1538,1448

Isopropyl (3S)-3-{(3RS)-4-acetyl-3,6-diphenyl-2-oxo-1,2,3,4-tetrahydropyrazin-1-yl}methylcarbonylamino-2-oxo-4-phenylbutyrate (Compound No. 2-13)

IR(Film,cm$^{-1}$)3308,3061,3028,1725,1678,1526,1496,1448

Isopropyl (3S)-3-{(3RS)-4-formyl-3-isopropyl-2-oxo-6-phenyl-1,2,3,4-tetrahydropyrazin-1-yl}methylcarbonylamino-2-oxo-4-phenylbutyrate (Compound No. 2-14)

IR(Film,cm$^{-1}$)3308,2975,1727,1682,1654,1538,1452

Isopropyl (3S)-3-{(3RS)-4-isobutyryl-3-isopropyl-2-oxo-6-phenyl-1,2,3,4-tetrahydropyrazin-1-yl}methylcarbonylamino-2-oxo-4-phenylbutyrate (Compound No. 2-15)

IR(Film,cm$^{-1}$)3316,1725,1679,1529

Isopropyl (3S)-3-{(3R)-4-isobutyryl-3-isopropyl-2-oxo-6-phenyl-1,2,3,4-tetrahydropyrazin-1-yl}methylcarbonylamino-2-oxo-4-phenylbutyrate (Compound No. 2-16)

IR(Film,cm$^{-1}$)3324,1727,1682,1524,1390,1227

Isopropyl (3S)-3-{(3RS)-3-isopropyl-2-oxo-6-phenyl-4-pivaloyl-1,2,3,4-tetrahydropyrazin-1-yl}methylcarbonylamino-2-oxo-4-phenylbutyrate (Compound No. 2-17)

IR(Film,cm$^{-1}$)3306,2974,2874,1725,1690,1666,1641

Isopropyl (3S)-3-{(3RS)-4-cyclohexylcarbonyl-3-isopropyl-2-oxo-6-phenyl-1,2,3,4-tetrahydropyrazin-1-yl}methylcarbonylamino-2-oxo-4-phenylbutyrate (Compound No. 2-18)

IR(Film,cm$^{-1}$)3316,2933,2857,1726,1678,1643,1527,1449

Isopropyl (3S)-3-{(3RS)-3-isopropyl-4-methoxycarbonyl-2-oxo-6-phenyl-1,2,3,4-tetrahydropyrazin-1-yl}methylcarbonylamino-2-oxo-4-phenylbutyrate (Compound No. 2-19)

IR(Film,cm$^{-1}$)3334,2965,1720,1689,1528,1446

Isopropyl (3S)-3-{(3RS)-4-ethoxycarbonyl-3-isopropyl-2-oxo-6-phenyl-1,2,3,4-tetrahydropyrazin-1-yl}methylcarbonylamino-2-oxo-4-phenylbutyrate (Compound No. 2-20)

IR(Film,cm$^{-1}$)3329,2979,1716,1687,1522

Isopropyl (3S)-3-{(3R)-3-isopropyl-4-methoxyacetyl-2-oxo-6-phenyl-1,2,3,4-tetrahydropyrazin-1-yl}methylcarbonylamino-2-oxo-4-phenylbutyrate (Compound No. 2-21)

$[\alpha]_D^{20}$ −80.2° (c=0.53, methanol)

IR(Film,cm$^{-1}$)3306,2966,2934,1725,1683,1522

Isopropyl (3S)-3-{(3R)-4-benzoyl-3-isopropyl-2-oxo-6-phenyl-1,2,3,4-tetrahydropyrazin-1-yl}methylcarbonylamino-2-oxo-4-phenylbutyrate (Compound No. 2-22)

$[\alpha]_D^{20}$ −113.6° (c=1.0, methanol)

IR(Film,cm$^{-1}$)3314,3061,3027,1725,1689,1578,1528,1495,1447

Isopropyl (3S)-3-{(3RS)-4-(4-chlorobenzoyl)-3-isopropyl-2-oxo-6-phenyl-1,2,3,4-tetrahydropyrazin-1-yl}methylcarbonylamino-2-oxo-4-phenylbutyrate (Compound No. 2-23)

IR(Film,cm$^{-1}$)3789,1725,1689,1642

Isopropyl (3S)-3-{(3RS)-3-isopropyl-4-(4-methoxybenzoyl)-2-oxo-6-phenyl-1,2,3,4-tetrahydropyrazin-1-yl}methylcarbonylamino-2-oxo-4-phenylbutyrate (Compound No. 2-24)

IR(Film,cm$^{-1}$)3306,1725,1689,1633,1512

Isopropyl (3S)-3-{(3RS)-3-isopropyl-4-(4-nitrobenzoyl)-2-oxo-6-phenyl-1,2,3,4-tetrahydropyrazin-1-yl}methylcarbonylamino-2-oxo-4-phenylbutyrate (Compound No. 2-25)

IR(Film,cm$^{-1}$)3318,1740,1681,1650,1601,1526

Isopropyl (3S)-3-{(3RS)-3-isopropyl-2-oxo-6-phenyl-4-(3-phenylpropanoyl)-1,2,3,4-tetrahydropyrazin-1-yl}methylcarbonylamino-2-oxo-4-phenylbutyrate (Compound No. 2-26)

IR(Film,cm$^{-1}$)3310,3061,3027,2966,1725,1678,1647, 1527,1497

Isopropyl (3S)-3-{(3RS)-4-benzyloxycarbonyl-3-isopropyl-2-oxo-6-phenyl-1,2,3,4-tetrahydropyrazin-1-yl}methylcarbonylamino-2-oxo-4-phenylbutyrate (Compound No. 2-27)

IR(Film,cm$^{-1}$)3332,3028,2966,1745,1714,1688,1519

Isopropyl (3S)-3-{(3RS)-3-isopropyl-2-oxo-4-phenoxyacetyl-6-phenyl-1,2,3,4-tetrahydropyrazin-1-yl}methylcarbonylamino-2-oxo-4-phenylbutyrate (Compound No. 2-28)

IR(Film,cm$^{-1}$)3319,3062,3027,2978,2935,2874,1726, 1681,1601

Isopropyl (3S)-3-{(3RS)-3-isopropyl-2-oxo-6-phenyl-4-(2-thienylcarbonyl)-1,2,3,4-tetrahydropyrazin-1-yl}methylcarbonylamino-2-oxo-4-phenylbutyrate (Compound No. 2-29)

IR(Film,cm$^{-1}$)3326,2975,2935,1744,1688,1630,1517

Isopropyl (3S)-3-{(3RS)-3-isopropyl-2-oxo-6-phenyl-4-(2-pyridylcarbonyl)-1,2,3,4-tetrahydropyrazin-1-yl}methylcarbonylamino-2-oxo-4-phenylbutyrate (Compound No. 2-30)

IR(Film,cm$^{-1}$)3314,1725,1683,1600,1521

Isopropyl (3S)-3-{(3RS)-3-isopropyl-2-oxo-6-phenyl-4-(3-pyridylcarbonyl)-1,2,3,4-tetrahydropyrazin-1-yl}methylcarbonylamino-2-oxo-4-phenylbutyrate (Compound No. 2-31)

IR(Film,cm$^{-1}$)3319,2973,1726,1674,1589,1529,1447

Isopropyl (3S)-3-{(3RS)-3-isopropyl-2-oxo-6-phenyl-4-(4-pyridylcarbonyl)-1,2,3,4-tetrahydropyrazin-1-yl}methylcarbonylamino-2-oxo-4-phenylbutyrate (Compound No. 2-32)

IR(Film,cm$^{-1}$)3306,2978,1724,1687,1647,1599,1550, 1526,1495,1447

Isopropyl (3S)-3-{(3RS)-3-isopropyl-4-methanesulfonyl-2-oxo-6-phenyl-1,2,3,4-tetrahydropyrazin-1-yl}methylcarbonylamino-2-oxo-4-phenylbutyrate (Compound No. 2-33)

IR(Film,cm$^{-1}$)3358,3027,2978,2934,1727,1682,1525, 1496,1467

Isopropyl (3S)-3-{(3RS)-4-benzenesulfonyl-3-isopropyl-2-oxo-6-phenyl-1,2,3,4-tetrahydropyrazin-1-yl}methylcarbonylamino-2-oxo-4-phenylbutyrate (Compound No. 2-34)

IR(Film,cm$^{-1}$)3368,1726,1686,1447

Isopropyl (3S)-3-{(3RS)-4-acetyl-3-isopropyl-2-oxo-6-(3,4,5-trimethoxyphenyl)-1,2,3,4-tetrahydropyrazin-1-yl}methylcarbonylamino-2-oxo-4-phenylbutyrate (Compound No 2-35)

IR(Film,cm$^{-1}$)3311,2969,2839,1727,1679,1583,1507, 1456

Isopropyl (3S)-3-{(3RS)-4-benzoyl-3-isopropyl-2-oxo-6-(3,4,5-trimethoxyphenyl)-1,2,3,4-tetrahydropyrazin-1-yl}methylcarbonyl-amino-2-oxo-4-phenylbutyrate (Compound No. 2-36)

IR(Film,cm$^{-1}$)3323,2968,2938,2837,1727,1670,1582, 1507,1454

Isopropyl (3S)-3-{(3RS)-3-isopropyl-4-methoxyacetyl-2-oxo-6-(3,4,5-trimethoxyphenyl)-1,2,3,4-tetrahydropyrazin-1-yl}methylcarbonyl-amino-2-oxo-4-phenylbutyrate (Compound No. 2-37)

IR(Film,cm$^{-1}$)3311,2968,2938,2830,1726,1681,1583, 1508,1456

Isopropyl (3S)-3-{(3RS)-4-acetyl-6-(3,4-dimethoxyphenyl)-3isopropyl-2-oxo-1,2,3,4-tetrahydropyrazin-1-yl}methylcarbonylamino-2oxo-4-phenylbutyrate (Compound No. 2-38)

IR(Film,cm$^{-1}$)3323,3017,2968,2937,2839,1726,1678, 1603,1583,1516,1469

Isopropyl (3S)-3-{(3RS)-4-benzoyl-6-(3,4-dimethoxyphenyl)-3-isopropyl-2-oxo-1,2,3,4-tetrahydropyrazin-1-yl}methylcarbonylamino-2-oxo-4-phenylbutyrate (Compound No. 2-39)

IR(Film,cm$^{-1}$)3338,2967,2839,1726,1681,1603,1580, 1517,1449

Isopropyl (3S)-3-{(3RS)-6-(3,4-dimethoxyphenyl)-3-isopropyl-4-methoxyacetyl-2-oxo-1,2,3,4-tetrahydropyrazin-1-yl}methylcarbonyl-amino-2-oxo-4-phenylbutyrate (Compound No. 2-40)

IR(Film,cm$^{-1}$)3322,2967,2936,2838,1727,1680,1603, 1583,1517,1465

Isopropyl (3S)-3-{(3RS)-4-benzoyl-3-isopropyl-6-(3-methoxyphenyl)-2-oxo-1,2,3,4-tetrahydropyrazin-1-yl}methylcarbonylamino-2-oxo-4-phenylbutyrate (Compound No. 2-41)

Isopropyl (3S)-3-{(3RS)-4-acetyl-3-isopropyl-2-oxo-6-(3,4,5-triacetoxyphenyl)-1,2,3,4-tetrahydropyrazin-1-yl}methylcarbonyl-amino-2-oxo-4-phenylbutyrate (Compound No. 2-42)

IR(Film,cm$^{-1}$)3338,2986,2937,1781,1745,1682,1651, 1498,1455

Isopropyl (3S)-3-{(3RS)-4-benzoyl-3-isopropyl-2-oxo-6-(3,4,5-triacetoxyphenyl)-1,2,3,4-tetrahydropyrazin-1-yl}methylcarbonyl-amino-2-oxo-4-phenylbutyrate (Compound No. 2-43)

IR(Film,cm$^{-1}$)3308,2981,2936,1781,1726,1670,1522, 1498

Isopropyl (3S)-3-{(3RS)-4-acetyl-6-(3,4-diacetoxyphenyl)-3-isopropyl-2-oxo-1,2,3,4-tetrahydropyrazin-1-yl}methylcarbonylamino-2-oxo-4-phenylbutyrate (Compound No. 2-44)

IR(Film,cm$^{-1}$)3307,3021,2981,2936,1770,1725,1682, 1650,1576,1505

(2S)-2-{(3RS)-4-Acetyl-3-isopropyl-2-oxo-6-phenyl-1,2,3,4-tetrahydropyrazin-1-yl}methylcarbonylamino-1-oxo-3-phenyl-1-(1,3-thiazol-2-yl)propane (Compound No. 2-45)

(2S)-2-{(3RS)-4-Acetyl-3-isopropyl-2-oxo-6-phenyl-1,2,3,4-tetrahydropyrazin-1-yl}methylcarbonylamino-1-(1,3-benzothiazol-2-yl)-1-oxo-3-phenylpropane (Compound No. 2-46)

(2S)-2-{(3RS)-4-Acetyl-3-isopropyl-2-oxo-6-phenyl-1,2,3,4-tetrahydropyrazin-1-yl}methylcarbonylamino-1-(4,5-dihydro-1,3-oxazol-2-yl)-1-oxo-3-phenylpropane (Compound No. 2-47)

IR(Film,cm$^{-1}$)3307,2965,1750,1678,1542,1496,1446

(2S)-2-{(3RS)-4-Acetyl-3-isopropyl-2-oxo-6-phenyl-1,2,3,4-tetrahydropyrazin-1-yl}methylcarbonylamino-1-(4,5-dihydro-1,3-thiazol-2-yl)-1-oxo-3-phenylpropane (Compound No. 2-48)

IR(Film,cm$^{-1}$)3308,3012,2965,1751,1680,1529,1445

(2S)-1-(4,5-Dihydro-1,3-oxazol-2-yl)-2-{(3RS)-3-isopropyl-4-methoxyacetyl-2-oxo-6-phenyl-1,2,3,4-tetrahydropyrazin-1-yl}-methylcarbonylamino-1-oxo-3-phenylpropane (Compound No. 2-49)

IR(KBr,cm$^{-1}$)3306,2964,1746,1681,1530,1447

(2S)-1-(1-Aza-3-oxaspiro[4,4]non-1-en-2-yl)-2-{(3RS)-4-benzoyl-3-isopropyl-2-oxo-6-phenyl-1,2,3,4- tetrahydropyrazin-1-yl}methylcarbonyl-amino-1-oxo-3-phenylpropane (Compound No. 2-50)

IR(Film,cm$^{-1}$)3308,2964,2873,1731,1670,1519,1447

(2S)-1-(1-Aza-3-oxaspiro[4,4]non-1-en-2-yl)-2-{(3RS)-3-isopropyl-4-methoxyacetyl-2-oxo-6-phenyl-1,2,3,4-tetrahydropyrazin-1-yl}-methylcarbonylamino-1-oxo-3-phenylpropane (Compound No. 2-51)

IR(Film,cm$^{-1}$)3310,2963,1729,1681,1521,1448

(2S)-1-(4,4-Dimethyl-4,5-dihydro-1,3-oxazol-2-yl)-2-{(3RS)-3-isopropyl-4-methoxyacetyl-2-oxo-6-phenyl-1,2,3,4-tetrahydropyrazin-1-yl}-methylcarbonylamino-1-oxo-3-phenylpropane (Compound No. 2-52)

IR(Film,cm$^{-1}$)3305,3064,2971,1733,1663,1588,1570,1440

(2S)-2-{(3RS)-4-Benzenesulfonyl-3-isopropyl-2-oxo-6-phenyl-1,2,3,4-tetrahydropyrazin-1-yl}methylcarbonylamino-1-(4,4-dimethyl-4,5-dihydro-1,3-oxazol-2-yl)-1-oxo-3-phenylpropane (Compound No. 2-53)

IR(Film,cm$^{-1}$)3348,3063,3027,2968,2932,1734,1682,1531,1447

(2S)-1-(4,4-Dimethyl-4,5-dihydro-1,3-oxazol-2-yl)-2-{(3RS)-3-isopropyl-2-oxo-6-phenyl-4-pivaloyl-1,2,3,4-tetrahydropyrazin-1-yl}-methylcarbonylamino-1-oxo-3-phenylpropane (Compound No. 2-54)

IR(Film,cm$^{-1}$)3319,2970,1731,1679,1518,1448

(2S)-2-{(3RS)-4-Acetyl-3-isopropyl-2-oxo-6-phenyl-1,2,3,4-tetrahydropyrazin-1-yl}methylcarbonylamino-1-(5,5-dimethyl-4,5-dihydro-1,3-thiazol-2-yl)-1-oxo-3-phenylpropane (Compound No. 2-55)

IR(Film,cm$^{-1}$)3308,3013,2964,2930,1682,1581,1520,1446

(2S)-1-(5,5-Dimethyl-4,5-dihydro-1,3-thiazol-2-yl)-2-{(3R)-3-isopropyl-2-oxo-6-phenyl-4-(2-pyridylcarbonyl)-1,2,3,4-tetrahydropyrazin-1-yl}methylcarbonylamino-1-oxo-3-phenylpropane (Compound No. 2-56)

IR(Film,cm$^{-1}$)3317,3060,3024,2963,2928,1682,1644,1584,1568,1520,1468

(2S)-1-(5,5-Dimethyl-4,5-dihydro-1,3-thiazol-2-yl)-2-{(3RS)-3-isopropyl-2-oxo-6-phenyl-4-(3-pyridylcarbonyl)-1,2,3,4-tetrahydropyrazin-1-yl}methylcarbonylamino-1-oxo-3-phenylpropane (Compound No. 2-57)

IR(Film,cm$^{-1}$)3325,3015,2931,1682,1644,1588,1520,1446

Isopropyl (3S)-3-{(3R)-4-acetyl-6-(3-benzyloxyphenyl)-3-isopropyl-2-oxo-1,2,3,4-tetrahydropyrazin-1-yl}methylcarbonylamino-2-oxo-4-phenylbutyrate (Compound No. 2-58)

IR(Film,cm$^{-1}$)3306,1725,1680,1599

Isopropyl (3S)-3-[(3R)-4-acetyl-6-{3-(3-chlorobenzyloxy)phenyl}-3-isopropyl-2-oxo-1,2,3,4-tetrahydropyrazin-1-yl]methylcarbonylamino-2-oxo-4-phenylbutyrate (Compound No. 2-59)

IR(Film,cm$^{-1}$)3299,1725 1679,1599

Isopropyl (3S)-3-[(3R)-4-acetyl-6-{3-(3,5-dichlorobenzyloxy)-phenyl}-3-isopropyl-2-oxo-1,2,3,4-tetrahydropyrazin-1-yl]methylcarbonyl-amino-2-oxo-4-phenylbutyrate (Compound No. 2-60)

[α]$_D^{20}$–65.7° (c=0.51, methanol)
IR(Film,cm$^{-1}$)3304,1725,1679,1571,1432,1387

Isopropyl (3S)-3-{(2RS)-2-isopropyl-3-oxo-3,4-dihydro-2H-1,4-thiazin-4-yl}methylcarbonylamino-2-oxo-4-phenylbutyrate (Compound No. 2-61)

IR(Film,cm$^{-1}$)3305,1727,1665,1529,1271

Isopropyl (3S)-3-{(2RS)-5-ethyl-2-isopropyl-3-oxo-3,4-dihydro-2H-1,4-thiazin-4-yl}methylcarbonylamino-2-oxo-4-phenylbutyrate (Compound No. 2-62)

IR(Film,cm$^{-1}$)3324,3062,1726,1667,1524,1497,1455,1375,1258

Isopropyl (3S)-3-{(2RS)-2-isopropyl-3-oxo-5-phenyl-3,4-dihydro-2H-1,4-thiazin-4-yl}methylcarbonylamino-2-oxo-4-phenylbutyrate (Compound No. 2-63)

IR(Film,cm$^{-1}$)3305,1727,1665,1529,1271

Isopropyl (3S)-3-{(2RS)-5-(4-fluorophenyl)-2-isopropyl-3-oxo-3,4-dihydro-2H-1,4-thiazin-4-yl}methylcarbonyl-amino-2-oxo-4-phenylbutyrate (Compound No. 2-64)

IR(Film,cm$^{-1}$)3326,1726,1673,1508,1227

Isopropyl (3S)-3-{(2RS)-2-isopropyl-5-(4-methoxyphenyl)-3-oxo-3,4-dihydro-2H-1,4-thiazin-4-yl}methylcarbonylamino-2-oxo-4-phenylbutyrate (Compound No. 2-65)

IR(Film,cm$^{-1}$)3326,1725,1670,1511,1249

Isopropyl (3S)-3-{(2RS)-2-methyl-3-oxo-3,4-dihydro-2H-1,4-thiazin-4-yl}methylcarbonylamino-2-oxo-4-phenylbutyrate (Compound No. 2-66)

IR(Film,cm$^{-1}$)3304,1726,1673,1538

Isopropyl (3S)-3-{(2RS)-2-ethyl-3-oxo-3,4-dihydro-2H-1,4-thiazin-4-yl}methylcarbonylamino-2-oxo-4-phenylbutyrate (Compound No. 2-67)

IR(Film,cm$^{-1}$)3307,3064,3027,1725,1667,1527,1496,1454

Isopropyl (3S)-3-{(2RS)-3-oxo-2-propyl-3,4-dihydro-2H-1,4-thiazin-4-yl}methylcarbonylamino-2-oxo-4-phenylbutyrate (Compound No. 2-68)

Isopropyl (3S)-3-{(2RS)-2-methoxy-3-oxo-3,4-dihydro-2H-1,4-thiazin-4-yl}methylcarbonylamino-2-oxo-4-phenylbutyrate (Compound No. 2-69)

Isopropyl (3S)-3-[(1RS)-1-{(2RS)-2-isopropyl-3-oxo-3,4-dihydro-2H-1,4-thiazin-4-yl}ethyl]carbonylamino-2-oxo-4-phenylbutyrate (Compound No. 2-70)

Isopropyl (3S)-3-[(1RS)-1-{(2RS)-2-isopropyl-3-oxo-3,4-dihydro-2H-1,4-thiazin-4-yl}propyl]carbonylamino-2-oxo-4-phenylbutyrate (Compound No. 2-71)

Isopropyl (3S)-3-[1-{(2RS)-2-isopropyl-3-oxo-3,4-dihydro-2H-1,4-thiazin-4-yl}-2-phenylethyl]carbonylamino-2-oxo-4-phenylbutyrate (Compound No. 2-72)

(3S)-3-{(3RS)-4-Acetyl-3-isopropyl-2-oxo-6-phenyl-1,2,3,4-tetrahydropyrazin-1-yl}carbonylamino-2-oxo-4-phenylbutyramide (Compound No. 2-73)

N$^1$-Isopropyl-(3RS)-3-{(3RS)-4-acetyl-3-isopropyl-2-oxo-6-phenyl-1,2,3,4-tetrahydropyrazin-1-yl}methylcarbonylamino-2-oxo-4-phenylbutyramide (Compound No. 2-74)

IR(Film,cm$^{-1}$)3305,2970,2933,1671,1522

N$^1$,N$^1$-Dimethyl-(3RS)-3-{(3RS)-4-acetyl-3-isopropyl-2-oxo-6-phenyl-1,2,3,4-tetrahydropyrazin-1-yl}methylcarbonylamino-2-oxo-4-phenylbutyramide (Compound No. 2-75)

IR(Film,cm$^{-1}$)3305,3061,3029,2964,2934,1722,1682,1640,1540

Example 3

The following compound is obtained by a method similar to Example 1.

(2RS,3RS)-3-{(3RS)-4-Acetyl-3-isopropyl-2-oxo-6-phenyl-1,2,3,4-tetrahydropyrazin-1-yl}methylcarbonylamino-2-hydroxy-4-phenyl-1,1,1-trifluorobutane (Compound No. 3-1)

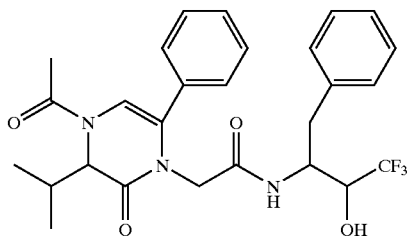

The following compounds are obtained by a method similar to Example 3.

IR(Film,cm$^{-1}$)3307,3064,3028,1669,1646,1546

(2RS,3RS)-3-{(3R)-4-Acetyl-3-isopropyl-2-oxo-6-phenyl-1,2,3,4-tetrahydropyrazin-1-yl}methylcarbonyl-amino-2-hydroxy-4-phenyl-1,1,1-trifluorobutane (Compound No. 3-2)

(2RS,3RS)-3-{(3S)-4-Acetyl-3-isopropyl-2-oxo-6-phenyl-1,2,3,4-tetrahydropyrazin-1-yl}methylcarbonyl-amino-2-hydroxy-4-phenyl-1,1,1-trifluorobutane (Compound No. 3-3)

(2RS,3RS)-3-(4-Acetyl-2-oxo-6-phenyl-1,2,3,4-tetrahydropyrazin-1-yl)methylcarbonylamino-2-hydroxy-4-phenyl-1,1,1-trifluorobutane (Compound No. 3-4)

IR(Film,cm$^{-1}$)3322,3064,3026,1675,1548,1497,1446

(2RS,3RS)-3-(4-Acetyl-3,3-dimethyl-2-oxo-6-phenyl-1,2,3,4-tetrahydropyrazin-1-yl)methylcarbonylamino-2-hydroxy-4-phenyl-1,1,1-trifluorobutane (Compound No. 3-5)

IR(Film,cm$^{-1}$)3322,3064,3026,1675,1548,1497,1446

(2RS,3RS)-3-{(3RS)-4-Acetyl-3-ethyl-2-oxo-6-phenyl-1,2,3,4-tetrahydropyrazin-1-yl}methylcarbonylamino-2-hydroxy-4-phenyl-1,1,1-trifluorobutane (Compound No. 3-6)

IR(Film,cm$^{-1}$)3308,3064,3027,1669,1646,1540,1498,1447

(2RS,3RS)-3-[(3RS)-4-Acetyl-3-{(1RS)-1-methylpropyl}-2-oxo-6-phenyl-1,2,3,4-tetrahydropyrazin-1-yl]methylcarbonylamino-2-hydroxy-4-phenyl-1,1,1-trifluorobutane (Compound No. 3-7)

IR(Film,cm$^{-1}$)3314,3064,3028,1670,1541,1497,1447

(2RS,3RS)-3-{(3RS)-4-Acetyl-3-isobutyl-2-oxo-6-phenyl-1,2,3,4-tetrahydropyrazin-1-yl}methylcarbonyl-amino-2-hydroxy-4-phenyl-1,1,1-trifluorobutane (Compound No. 3-8)

IR(Film,cm$^{-1}$)3315,3016,1671,1646,1548

(2RS,3RS)-3-{(3RS)-4-Acetyl-3-cyclohexyl-2-oxo-6-phenyl-1,2,3,4-tetrahydropyrazin-1-yl}methylcarbonyl-amino-2-hydroxy-4-phenyl-1,1,1-trifluorobutane (Compound No. 3-9)

IR(Film,cm$^{-1}$)3312,3064,3026,1670,1541,1448

(2RS,3RS)-3-[(3RS)-4-Acetyl-3-{(1RS)-1-tert-butyldimethylsilyloxy-ethyl}-2-oxo-6-phenyl-1,2,3,4-tetrahydropyrazin-1-yl]methylcarbonyl-amino-2-hydroxy-4-phenyl-1,1,1-trifluorobutane (Compound No. 3-10)

(2RS,3RS)-3-{(3RS)-4-Acetyl-3-methoxymethyl-2-oxo-6-phenyl-1,2,3,4-tetrahydropyrazin-1-yl}methylcarbonyl-amino-2-hydroxy-4-phenyl-1,1,1-trifluorobutane (Compound No. 3-11)

(2RS,3RS)-3-{(3RS)-4-Acetyl-3-(2-methoxyethyl)-2-oxo-6-phenyl-1,2,3,4-tetrahydropyrazin-1-yl}methylcarbonylamino-2-hydroxy-4-phenyl-1,1,1-trifluorobutane (Compound No. 3-12)

IR(Film,cm$^{-1}$)3307,3064,3026,1672,1649,1540,1447

(2RS,3RS)-3-{(3RS)-4-Acetyl-3,6-diphenyl-2-oxo-1,2,3,4-tetrahydropyrazin-1-yl}methylcarbonylamino-2-hydroxy-4-phenyl-1,1,1-trifluorobutane (Compound No. 3-13)

IR(Film,cm$^{-1}$)3316,3064,3027,1668,1549,1496,1448

(2RS,3RS)-3-{(3RS)-4-Formyl-3-isopropyl-2-oxo-6-phenyl-1,2,3,4-tetrahydrhopyrazin-1-yl}methylcarbonyl-amino-2-hydroxy-4-phenyl-1,1,1-trifluorobutane (Compound No. 3-14)

IR(Film,cm$^{-1}$)3307,3064,3027,2966,1676,1654,1540,1496,1447

(2RS,3RS)-2-Hydroxy-3-{(3RS)-4-isobutyryl-3-isopropyl-2-oxo-6-phenyl-1,2,3,4-tetrahydropyrazin-1-yl}methylcarbonylamino-4-phenyl-1,1,1-trifluorobutane (Compound No. 3-15)

IR(Film,cm$^{-1}$)3323,1665,1547

(2RS,3RS)-2-Hydroxy-3-{(3R)-4-isobutyryl-3-isopropyl-2-oxo-6-phenyl-1,2,3,4-tetrahydropyrazin-1-yl}methylcarbonylamino-4-phenyl-1,1,1-trifluorobutane (Compound No. 3-16)

IR(Film,cm$^{-1}$)3328,1666,1546

(2RS,3RS)-2-Hydroxy-3-{(3RS)-3-isopropyl-2-oxo-6-phenyl-4-pivaloyl-1,2,3,4-tetrahydropyrazin-1-yl}methylcarbonylamino-4-phenyl-1,1,1-trifluorobutane (Compound No. 3-17)

IR(Film,cm$^{-1}$)3789,1660,1547

(2RS,3RS)-3-{(3RS)-4-Cyclohexylcarbonyl-3-isopropyl-2-oxo-6-phenyl-1,2,3,4-tetrahydropyrazin-1-yl}methylcarbonylamino-2-hydroxy-4-phenyl-1,1,1-trifluorobutane (Compound No. 3-18)

IR(Film,cm$^{-1}$)3324,3064,3015,2934,2857,1666,1548,1497,1447

(2RS,3RS)-2-Hydroxy-3-{(3RS)-3-isopropyl-4-methoxycarbonyl-2-oxo-6-phenyl-1,2,3,4-tetrahydropyrazin-1-yl}methylcarbonylamino-4-phenyl-1,1,1-trifluorobutane (Compound No. 3-19)

IR(Film,cm$^{-1}$)3326,2964,1688,1536,1446

(2RS,3RS)-3-{(3RS)-4-Ethoxycarbonyl-3-isopropyl-2-oxo-6-phenyl-1,2,3,4-tetrahydropyrazin-1-yl}methylcarbonylamino-2-hydroxy-4-phenyl-1,1,1-trifluorobutane (Compound No. 3-20)

IR(Film,cm$^{-1}$)3327,3026,2967,1688

(2RS,3RS)-2-Hydroxy-3-{(3R)-3-isopropyl-4-methoxyacetyl-2-oxo-6-phenyl-1,2,3,4-tetrahydropyrazin-1-yl}methylcarbonylamino-4-phenyl-1,1,1-trifluorobutane (Compound No. 3-21)

IR(Film,cm$^{-1}$)3321,1678

(2RS,3RS)-3-{(3R)-4-Benzoyl-3-isopropyl-2-oxo-6-phenyl-1,2,3,4-tetrahydropyrazin-1-yl}methylcarbonyl-amino-2-hydroxy-4-phenyl-1,1,1-trifluorobutane (Compound No. 3-22)

IR(Film,cm$^{-1}$)3316,1666

(2RS,3RS)-3-{(3RS)-4-(4-Chlorobenzoyl)-3-isopropyl-2-oxo-6-phenyl-1,2,3,4-tetrahydropyrazin-1-yl}methylcarbonylamino-2-hydroxy-4-phenyl-1,1,1-trifluorobutane (Compound No. 3-23)

IR(Film,cm$^{-1}$)3786,1664,1548

(2RS,3RS)-2-Hydroxy-3-{(3RS)-3-isopropyl-4-(4-methoxybenzoyl)-2-oxo-6-phenyl-1,2,3,4-tetrahydropyrazin-1-yl}methylcarbonylamino-4-phenyl-1,1,1-trifluorobutane (Compound No. 3-24)

IR(Film,cm$^{-1}$)3319,1666,1660

(2RS,3RS)-2-Hydroxy-3-{(3RS)-3-isopropyl-4-(4-nitrobenzoyl)-2-oxo-6-phenyl-1,2,3,4-tetrahydropyrazin-1-yl}methylcarbonylamino-4-phenyl-1,1,1-trifluorobutane (Compound No. 3-25)

(2RS,3RS)-2-Hydroxy-3-{(3RS)-3-isopropyl-2-oxo-6-phenyl-4-(3-phenylpropanoyl)-1,2,3,4-tetrahydropyrazin-1-yl}methylcarbonylamino-4-phenyl-1,1,1-trifluorobutane (Compound No. 3-26)

(2RS,3RS)-3-{(3RS)-4-Benzyloxycarbonyl-3-isopropyl-2-oxo-6-phenyl-1,2,3,4-tetrahydropyrazin-1-yl}methylcarbonylamino-2-hydroxy-4phenyl-1,1,1-trifluorobutane (Compound No. 3-27)

IR(Film,cm$^{-1}$)3330,3064,3028,2966,1688,1549

(2RS,3RS)-2-Hydroxy-3-{(3RS)-3-isopropyl-2-oxo-4-phenoxyacetyl-6-phenyl-1,2,3,4-tetrahydropyrazin-1-yl}methylcarbonylamino-4-phenyl-1,1,1-trifluorobutane (Compound No. 3-28)

IR(Film,cm$^{-1}$)3324,1762,1682,1496

(2RS,3RS)-2-Hydroxy-3-{(3RS)-3-isopropyl-2-oxo-6-phenyl-4-(2-thienylcarbonyl)-1,2,3,4-tetrahydropyrazin-1-yl}methylcarbonylamino-4-phenyl-1,1,1-trifluorobutane (Compound No. 3-29)

IR(Film,cm$^{-1}$)3323,2966,1676,1628,1544

(2RS,3RS)-2-Hydroxy-3-{(3RS)-3-isopropyl-2-oxo-6-phenyl-4-(2-pyridylcarbonyl)-1,2,3,4-tetrahydropyrazin-1-yl}methylcarbonylamino-4-phenyl-1,1,1-trifluorobutane (Compound No. 3-30)

IR(Film,cm$^{-1}$)3321,1665,1541,1442

(2RS,3RS)-2-Hydroxy-3-{(3RS)-3-isopropyl-2-oxo-6-phenyl-4-(3-pyridylcarbonyl)-1,2,3,4-tetrahydropyrazin-1-yl}methylcarbonylamino-4-phenyl-1,1,1-trifluorobutane (Compound No. 3-31)

IR(Film,cm$^{-1}$)3322,3028,2967,1670,1638,1590,1549,1447

(2RS,3RS)-2-Hydroxy-3-{(3RS)-3-isopropyl-2-oxo-6-phenyl-4-(4-pyridylcarbonyl)-1,2,3,4-tetrahydropyrazin-1-yl}methylcarbonylamino-4-phenyl-1,1,1-trifluorobutane (Compound No. 3-32)

IR(Film,cm$^{-1}$)3325,3027,2967,1674,1642,1601,1551,1496,1447

(2RS,3RS)-2-Hydroxy-3-{(3RS)-3-isopropyl-4-methanesulfonyl-2-oxo-6-phenyl-1,2,3,4-tetrahydropyrazin-1-yl}methylcarbonylamino-4-phenyl-1,1,1-trifluorobutane (Compound No. 3-33)

(2RS,3RS)-3-{(3RS)-4-Benzenesulfonyl-3-isopropyl-2-oxo-6-phenyl-1,2,3,4-tetrahydropyrazin-1-yl}methylcarbonylamino-2-hydroxy-4-phenyl-1,1,1-trifluorobutane (Compound No. 3-34)

IR(Film,cm$^{-1}$)3369,1675,1538

(2RS,3RS)-3-{(3RS)-4-Acetyl-3-isopropyl-2-oxo-6-(3,4,5-trimethoxyphenyl)-1,2,3,4-tetrahydropyrazin-1-yl}methylcarbonyl-amino-4-phenyl-1,1,1-trifluorobutane (Compound No. 3-35)

IR(Film,cm$^{-1}$)3314,3086,3012,2968,2877,2835,1671,1583,1547,1507,1455

(2RS,3RS)-3-{(3RS)-4-Benzoyl-3-isopropyl-2-oxo-6-(3,4,5-trimethoxyphenyl)-1,2,3,4-tetrahydropyrazin-1-yl}methylcarbonyl-amino-2-hydroxy-4-phenyl-1,1,1-trifluorobutane (Compound No. 3-36)

IR(Film,cm$^{-1}$)3324,3065,3012,2966,2837,1665,1583,1546,1509,1453

(2RS,3RS)-2-Hydroxy-3-{(3RS)-3-isopropyl-4-methoxyacetyl-2-oxo-6-(3,4,5-trimethoxyphenyl)-1,2,3,4-tetrahydropyrazin-1-yl}methylcarbonyl-amino-4-phenyl-1,1,1-trifluorobutane (Compound No. 3-37)

IR(Film,cm$^{-1}$)3324,3066,3010,2966,2940,2830,1682,1584,1540,1507,1455

(2RS,3RS)-3-{(3RS)-4-Acetyl-6-(3,4-dimethoxyphenyl)-3-isopropyl-2-oxo-1,2,3,4-tetrahydropyrazin-1-yl}methylcarbonylamino-2-hydroxy-4-phenyl-1,1,1-trifluorobutane (Compound No. 3-38)

IR(Film,cm$^{-1}$)3324,3085,3017,2966,2937,2839,1670,1604,1582,1517,1465,1454

(2RS,3RS)-3-{(3RS)-4-Benzoyl-6-(3,4-dimethoxyphenyl)-3-isopropyl-2-oxo-1,2,3,4-tetrahydropyrazin-1-yl}methylcarbonylamino-2-hydroxy-4-phenyl-1,1,1-trifluorobutane (Compound No. 3-39)

IR(Film,cm$^{-1}$)3325,3064,3023,2965,2937,2839,1666,1602,1579,1517,1465,1447

(2RS,3RS)-3-{(3RS)-6-(3,4-Dimethoxyphenyl)-3-isopropyl-4-methoxymethyl-2-oxo-1,2,3,4-tetrahydropyrazin-1-yl}methylcarbonyl-amino-2-hydroxy-4-phenyl-1,1,1-trifluorobutane (Compound No. 3-40)

IR(Film,cm$^{-1}$)3326,3085,3013,2965,2837,1677,1604,1517,1453

(2RS,3RS)-3-{(3RS)-4-Benzoyl-3-isopropyl-6-(3-methoxyphenyl)-2-oxo-1,2,3,4-tetrahydropyrazin-1-yl}methylcarbonylamino-2-hydroxy-4-phenyl-1,1,1-trifluorobutane (Compound No. 3-41)

(2RS,3RS)-3-{(3RS)-4-Acetyl-3-isopropyl-2-oxo-6-(3,4,5-triacetoxyphenyl)-1,2,3,4-tetrahydropyrazin-1-yl}methylcarbonyl-amino-2-hydroxy-4-phenyl-1,1,1-trifluorobutane (Compound No. 3-42)

(2RS,3RS)-3-{(3RS)-4-Benzoyl-3-isopropyl-2-oxo-6-(3,4,5-triacetoxyphenyl)-1,2,3,4-tetrahydropyrazin-1-yl}methylcarbonyl-amino-2-hydroxy-4-phenyl-1,1,1-trifluorobutane (Compound No. 3-43)

(2RS,3RS)-3-{(3RS)-4-Acetyl-6-(3,4-diacetoxyphenyl)-3-isopropyl-2-oxo-1,2,3,4-tetrahydropyrazin-1-yl}methylcarbonylamino-2-hydroxy-4-phenyl-1,1,1-trifluorobutane (Compound No. 3-44)

(2RS,3RS)-3-{(3R)-4-Acetyl-6-(3-benzyloxyphenyl)-3-isopropyl-2-oxo-1,2,3,4-tetrahydropyrazin-1-yl}methylcarbonylamino-2-hydroxy-4-phenyl-1,1,1-trifluorobutane (Compound No. 3-45)

IR(Film,cm$^{-1}$)3311,1671

(2RS,3RS)-3-[(3R)-4-Acetyl-6-{3-(3-chlorobenzyloxy)phenyl}-3-isopropyl-2-oxo-1,2,3,4-tetrahydropyrazin-1-yl]methylcarbonylamino-2-hydroxy-4-phenyl-1,1,1-trifluorobutane (Compound No. 3-46)

IR(Film,cm$^{-1}$)3317,1671,1578,1492,1391,1276

(2RS,3RS)-3-[(3R)-4-Acetyl-6-{3-(3,5-dichlorobenzyloxy)phenyl}-3-isopropyl-2-oxo-1,2,3,4-tetrahydropyrazin-1-yl]methylcarbonylamino-2-hydroxy-4-phenyl-1,1,1-trifluorobutane (Compound No. 3-47)

IR(Film,cm$^{-1}$)3317,1671,1432,1391,1276,1213

(2RS,3RS)-2-{(3RS)-4-Benzoyl-3-isopropyl-2-oxo-6-phenyl-1,2,3,4-tetrahydropyrazin-1-yl}methylcarbonyl-amino-4,4,5,5,6,6,6-heptafluoro-3-hydroxy-1-phenylhexane (Compound No. 3-48)

IR(Film,cm$^{-1}$)3318,3064,3028,2967,1666,1639,1548, 1494,1448,1391

Example 4

(3RS)-3-{(3RS)-4-Acetyl-3-isopropyl-2-oxo-6-phenyl-1, 2,3,4-tetrahydropyrazin-1-yl}methylcarbonylamino-2-oxo-4-phenyl-1,1,1-trifluorobutane (Compound No. 4-1)

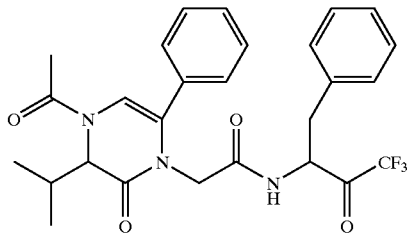

A solution of dimethyl sulfoxide (0.26 ml) in anhydrous methylene chloride (4.0 ml) is cooled with methanol/dry ice, oxalyl chloride (0.16 ml) is added to the solution, and the mixture is stirred for 10 minutes. To the mixture is added a solution of (2RS,3RS)-3-{(3RS)-4-acetyl-3-isopropyl-2-oxo-6-phenyl-1,2,3,4-tetrahydropyrazin-1-yl}methylcarbonylamino-2-hydroxy-4-phenyl-1,1,1-trifluorobutane (0.75 ml, Compound No. 2-1) in anhydrous methylene chloride (3.0 ml). The temperature is raised to 0° C., triethylamine (0.75 ml) is added thereto, and the whole is stirred for one hour. Ethyl acetate is added to the reaction mixture, the whole is washed with a saturated aqueous ammonium chloride solution and saturated brine successively, and the organic layer is dried over anhydrous magnesium sulfate. The organic layer is concentrated under reduced pressure, and the resulting residue is purified by silica gel column chromatography to give the titled compound (154 mg).

IR(Film,cm$^{-1}$)3295,3088,1668,1540

The following compounds are obtained by a method similar to Example 4.

(3RS)-3-{(3R)-4-Acetyl-3-isopropyl-2-oxo-6-phenyl-1, 2,3,4-tetrahydropyrazin-1-yl}methylcarbonylamino-2-oxo-4-phenyl-1,1,1-trifluorobutane (Compound No. 4-2)

(3RS)-3-{(3S)-4-Acetyl-3-isopropyl-2-oxo-6-phenyl-1,2, 3,4-tetrahydropyrazin-1-yl}methylcarbonylamino-2-oxo-4-phenyl-1,1,1-trifluorobutane (Compound No. 4-3)

(3RS)-3-{4-Acetyl-2-oxo-6-phenyl-1,2,3,4-tetrahydropyrazin-1-yl}-methylcarbonylamino-2-oxo-4-phenyl-1,1,1-trifluorobutane (Compound No. 4-4)

(3RS)-3-(4-Acetyl-3,3-dimethyl-2-oxo-6-phenyl-1,2,3,4-tetrahydropyrazin-1-yl)methylcarbonylamino-2-oxo-4-phenyl-1,1,1-trifluorobutane (Compound No. 4-5)

IR(Film,cm$^{-1}$)3312,1755,1661,1548,1495

(3RS)-3-{(3RS)-4-Acetyl-3-ethyl-2-oxo-6-phenyl-1,2,3, 4-tetrahydropyrazin-1-yl}methylcarbonylamino-2-oxo-4-phenyl-1,1,1-trifluorobutane (Compound No. 4-6)

IR(Film,cm$^{-1}$)3323,3064,3028,1672,1541,1497

(3RS)-3-[(3RS)-4-Acetyl-3-{(1RS)-1-methylpropyl}-2-oxo-6-phenyl-1,2,3,4-tetrahydropyrazin-1-yl] methylcarbonylamino-2-oxo-4-phenyl-1,1,1-trifluorobutane (Compound No. 4-7)

IR(Film,cm$^{-1}$)3292,1784,1671,1529,1496

(3RS)-3-{(3RS)-4-Acetyl-3-isobutyl-2-oxo-6-phenyl-1, 2,3,4-tetrahydropyrazin-1-yl}methylcarbonylamino-2-oxo-4-phenyl-1,1,1-trifluorobutane (Compound No. 4-8)

IR(Film,cm$^{-1}$)3304,3024,1782,1765,1679,1646,1530

(3RS)-3-{(3RS)-4-Acetyl-3-cyclohexyl-2-oxo-6-phenyl-1,2,3,4-tetrahydropyrazin-1-yl}methylcarbonylamino-2-oxo-4-phenyl-1,1,1-trifluorobutane (Compound No. 4-9)

IR(Film,cm$^{-1}$)3278,3025,1785,1678,1525,1448

(3RS)-3-[(3RS)-4-Acetyl-3-{(1RS)-1-tert-butyldimethylsilyloxyethyl}-2-oxo-6-phenyl-1,2,3,4-tetrahydropyrazin-1-yl]methylcarbonylamino-2-oxo-4-phenyl-1,1,1-trifluorobutane (Compound No. 4-10)

(3RS)-3-{(3RS)-4-Acetyl-3-methoxymethyl-2-oxo-6-phenyl-1,2,3,4-tetrahydropyrazin-1-yl}methylcarbonyl-amino-2-oxo-4-phenyl-1,1,1-trifluorobutane (Compound No. 4-11)

(3RS)-3-{(3RS)-4-Acetyl-3-(2-methoxyethyl)-2-oxo-6-phenyl-1,2,3,4-tetrahydropyrazin-1-yl}methylcarbonyl-amino-2-oxo-4-phenyl-1,1,1-trifluorobutane (Compound No. 4-12)

IR(Film,cm$^{-1}$)3316,3063,1676,1541,1446

(3RS)-3-{(3RS)-4-Acetyl-3,6-diphenyl-2-oxo-1,2,3,4-tetrahydropyrazin-1-yl}methylcarbonylamino-2-oxo-4-phenyl-1,1,1-trifluorobutane (Compound No. 4-13)

IR(Film,cm$^{-1}$)3271,3026,1783,1679,1526,1496,1447

(3RS)-3-{(3RS)-4-Formyl-3-isopropyl-2-oxo-6-phenyl-1,2,3,4-tetrahydropyrazin-1-yl}methylcarbonylamino-2-oxo-4-phenyl-1,1,1-trifluorobutane (Compound No. 4-14)

IR(Film,cm$^{-1}$)3306,3065,3026,2968,1672,1656,1535, 1497,1447

(3RS)-3-{(3RS)-4-Isobutyryl-3-isopropyl-2-oxo-6-phenyl-1,2,3,4-tetrahydropyrazin-1-yl}methylcarbonyl-anmino-2-oxo-4-phenyl-1,1,1-trifluorobutane (Compound No. 4-15)

IR(Film,cm$^{-1}$)3306,1763,1668,1540

(3RS)-3-{(3R)-4-Isobutyryl-3-isopropyl-2-oxo-6-phenyl-1,2,3,4-tetrahydropyrazin-1-yl}methylcarbonylamino-2-oxo-4-phenyl-1,1,1-trifluorobutane (Compound No. 4-16)

IR(Film,cm$^{-1}$)3305,1666,1537

(3RS)-3-{(3RS)-3-Isopropyl-2-oxo-6-phenyl-4-pivaloyl-1,2,3,4-tetrahydropyrazin-1-yl}methylcarbonylamino-2-oxo-4-phenyl-1,1,1-trifluorobutane (Compound No. 4-17)

IR(Film,cm$^{-1}$)3310,1666,1540

(3RS)-3-{(3RS)-4-Cyclohexylcarbonyl-3-isopropyl-2-oxo-6-phenyl-1,2,3,4-tetrahydropyrazin-1-yl}methylcarbonylamino-2-oxo-4-phenyl-1,1,1-trifluorobutane (Compound No. 4-18)

IR(Film,cm$^{-1}$)3286,3027,2934,2857,1717,1673,1638, 1521,1449

(3RS)-3-{(3RS)-3-Isopropyl-4-methoxycarbonyl-2-oxo-6-phenyl-1,2,3,4-tetrahydropyrazin-1-yl}methylcarbonyl-amino-2-oxo-4-phenyl-1,1,1-trifluorobutane (Compound No. 4-19)

IR(Film,cm$^{-1}$)3305,3027,2964,1784,1718,1689,1522, 1446

(3RS)-3-{(3RS)-4-Ethoxycarbonyl-3-isopropyl-2-oxo-6-phenyl-1,2,3,4-tetrahydropyrazin-1-yl}methylcarbonyl-amino-2-oxo-4-phenyl-1,1,1-trifluorobutane (Compound No. 4-20)

(3RS)-3-{(3R)-3-Isopropyl-4-methoxyacetyl-2-oxo-6-phenyl-1,2,3,4-tetrahydropyrazin-1-yl}methylcarbonyl-amino-2-oxo-4-phenyl-1,1,1-trifluorobutane (Compound No. 4-21)

IR(Film,cm$^{-1}$)3305,1678

(3RS)-3-{(3R)-4-Benzoyl-3-isopropyl-2-oxo-6-phenyl-1, 2,3,4-tetrahydropyrazin-1-yl}methylcarbonylamino-2-oxo-4-phenyl-1,1,1-trifluorobutane (Compound No. 4-22)

IR(Film,cm$^{-1}$)3745,3471,3256,3089,1689,1628

(3RS)-3-{(3RS)-4-(4-Chlorobenzoyl)-3-isopropyl-2-oxo-6-phenyl-1,2,3,4-tetrahydropyrazin-1-yl}methylcarbonylamino-2-oxo-4-phenyl-1,1,1-trifluorobutane (Compound No. 4-23)

IR(Film,cm$^{-1}$)3307,1666,1660,1596

(3RS)-3-{(3RS)-3-Isopropyl-4-(4-methoxybenzoyl)-2-oxo-6-phenyl-1,2,3,4-tetrahydropyrazin-1-yl}methylcarbonylamino-2-oxo-4-phenyl-1,1,1-trifluorobutane (Compound No. 4-24)

IR(Film,cm$^{-1}$)3305,1665,1660

(3RS)-3-{(3RS)-3-Isopropyl-4-(4-nitrobenzoyl)-2-oxo-6-phenyl-1,2,3,4-tetrahydropyrazin-1-yl}methylcarbonylamino-2-oxo-4-phenyl-1,1,1-trifluorobutane (Compound No. 4-25)

(3RS)-3-{(3RS)-3-Isopropyl-2-oxo-6-phenyl-4-(3-phenylpropanoy)-1,2,3,4-tetrahydropyrazin-1-yl}methylcarbonylamino-2-oxo-4-phenyl-1,1,1-trifluorobutane (Compound No. 4-26)

(3RS)-3-{(3RS)-4-Benzyloxycarbonyl-3-isopropyl-2-oxo-6-phenyl-1,2,3,4-tetrahydropyrazin-1-yl}methylcarbonylamino-2-oxo-4-phenyl-1,1,1-trifluorobutane (Compound No. 4-27)

(3RS)-3-{(3RS)-3-Isopropyl-2-oxo-4-phenoxyacetyl-6-phenyl-1,2,3,4-tetrahydropyrazin-1-yl}methylcarbonylamino-2-oxo-4-phenyl-1,1,1-trifluorobutane (Compound No. 4-28)

IR(Film,cm$^{-1}$)3321,1761,1677,1599,1542,1495,1448

(3RS)-3-{(3RS)-3-Isopropyl-2-oxo-6-phenyl-4-(2-thienylcarbonyl)-1,2,3,4-tetrahydropyrazin-1-yl}methylcarbonylamino-2-oxo-4-phenyl-1,1,1-trifluorobutane (Compound No. 4-29)

IR(Film,cm$^{-1}$)3322,3085,3028,2966,1782,1763,1687,1628,1518

(3RS)-3-{(3RS)-3-Isopropyl-2-oxo-6-phenyl-4-(2-pyridylcarbonyl)-1,2,3,4-tetrahydropyrazin-1-yl}methylcarbonylamino-2-oxo-4-phenyl-1,1,1-trifluorobutane (Compound No. 4-30)

IR(Film,cm$^{-1}$)3317,1670,1650,1549

(3RS)-3-{(3RS)-3-Isopropyl-2-oxo-6-phenyl-4-(3-pyridylcarbonyl)-1,2,3,4-tetrahydropyrazin-1-yl}methylcarbonylamino-2-oxo-4-phenyl-1,1,1-trifluorobutane (Compound No. 4-31)

IR(Film,cm$^{-1}$)3289,3026,2967,1721,1672,1644,1589,1526,1496,1446

(3RS)-3-{(3RS)-3-Isopropyl-2-oxo-6-phenyl-4-(4-pyridylcarbonyl)-1,2,3,4-tetrahydropyrazin-1-yl}methylcarbonylamino-2-oxo-4-phenyl-1,1,1-trifluorobutane (Compound No. 4-32)

IR(Film,cm$^{-1}$)3291,3025,2968,1787,1679,1599,1549,1495,1446

(3RS)-3-{(3RS)-3-Isopropyl-4-methanesulfonyl-2-oxo-6-phenyl-1,2,3,4-tetrahydropyrazin-1-yl}methylcarbonylamino-2-oxo-4-phenyl-1,1,1-trifluorobutane (Compound No. 4-33)

(3RS)-3-{(3RS)-4-Benzenesulfonyl-3-isopropyl-2-oxo-6-phenyl-1,2,3,4-tetrahydropyrazin-1-yl}methylcarbonylamino-2-oxo-4-phenyl-1,1,1-trifluorobutane (Compound No. 4-34)

IR(Film,cm$^{-1}$)3894,1672,1447

(3RS)-3-{(3RS)-4-Acetyl-3-isopropyl-2-oxo-6-(3,4,5-trimethoxyphenyl)-1,2,3,4-tetrahydropyrazin-1-yl}methylcarbonylamino-2-oxo-4-phenyl-1,1,1-trifluorobutane (Compound No. 4-35)

IR(Film,cm$^{-1}$)3314,3086,3012,2968,2877,2835,1671,1583,1547,1507,1455

(3RS)-3-{(3RS)-4-Benzoyl-3-isopropyl-2-oxo-6-(3,4,5-trimethoxyphenyl)-1,2,3,4-tetrahydropyrazin-1-yl}methylcarbonylamino-2-oxo-4-phenyl-1,1,1-trifluorobutane (Compound No. 4-36)

IR(Film,cm$^{-1}$)3324,3065,3012,2966,2837,1665,1583,1546,1509,1453

(3RS)-3-{(3RS)-3-Isopropyl-4-methoxyacetyl-2-oxo-6-(3,4,5-trimethoxyphenyl)-1,2,3,4-tetrahydropyrazin-1-yl}methylcarbonylamino-2-oxo-4-phenyl-1,1,1-trifluorobutane (Compound No. 4-37)

IR(Film,cm$^{-1}$)3324,3066,3010,2966,2940,2830,1682,1584,1540,1507,1455

(3RS)-3-{(3RS)-4-Acetyl-6-(3,4-dimethoxyphenyl)-3-isopropyl-2-oxo-1,2,3,4-tetrahydropyrazin-1-yl}methylcarbonylamino-2-oxo-4-phenyl-1,1,1-trifluorobutane (Compound No. 4-38)

IR(Film,cm$^{-1}$)3324,3085,3017,2966,2937,2839,1670,1604,1582,1517,1465,1454

(3RS)-3-{(3RS)-4-Benzoyl-6-(3,4-dimethoxyphenyl)-3-isopropyl-2-oxo-1,2,3,4-tetrahydropyrazin-1-yl}methylcarbonylamino-2-oxo-4-phenyl-1,1,1-trifluorobutane (Compound No. 4-39)

IR(Film,cm$^{-1}$)3325,3064,3023,2965,2937,2839,1666,1602,1579,1517,1465,1447

(3RS)-3-{(3RS)-6-(3,4-dimethoxyphenyl)-3-isopropyl-4-methoxyacetyl-2-oxo-1,2,3,4-tetrahydropyrazin-1-yl}methylcarbonylamino-2-oxo-4-phenyl-1,1,1-trifluorobutane (Compound No. 4-40)

IR(Film,cm$^{-1}$)3326,3085,3013,2965,2837,1677,1604,1517,1453

(3RS)-3-{(3RS)-4-Benzoyl-3-isopropyl-6-(3-methoxyphenyl)-2-oxo-1,2,3,4-tetrahydropyrazin-1-yl}methylcarbonylamino-2-oxo-4-phenyl-1,1,1-trifluorobutane (Compound No. 4-41)

(3RS)-3-{(3RS)-4-Acetyl-3-isopropyl-2-oxo-6-(3,4,5-triacetoxyphenyl)-1,2,3,4-tetrahydropyrazin-1-yl}methylcarbonylamino-2-oxo-4-phenyl-1,1,1-trifluorobutane (Compound No. 4-42)

(3RS)-3-{(3RS)-4-Benzoyl-3-isopropyl-2-oxo-6-(3,4,5-triacetoxyphenyl)-1,2,3,4-tetrahydropyrazin-1-yl}methylcarbonylamino-2-oxo-4-phenyl-1,1,1-trifluorobutane (Compound No. 4-43)

(3RS)-3-{(3RS)-4-Acetyl-6-(3,4-diacetoxyphenyl)-3-isopropyl-2-oxo-1,2,3,4-tetrahydropyrazin-1-yl}methylcarbonylamino-2-oxo-4-phenyl-1,1,1-trifluorobutane (Compound No. 4-44)

(3RS)-3-{(3R)-4-Acetyl-6-(3-benzyloxyphenyl)-3-isopropyl-2-oxo-1,2,3,4-tetrahydropyrazin-1-yl}methylcarbonylamino-2-oxo-4-phenyl-1,1,1-trifluorobutane (Compound No. 4-45)

IR(Film,cm$^{-1}$)3291,1682,1282

(3RS)-3-[(3R)-4-Acetyl-6-{3-(3-chlorobenzyloxy)phenyl}-3-isopropyl-2-oxo-1,2,3,4-tetrahydropyrazin-1-yl]methylcarbonylamino-2-oxo-4-phenyl-1,1,1-trifluorobutane (Compound No. 4-46)

IR(Film,cm$^{-1}$)3304,1670,1390,1278

(3RS)-3-[(3R)-4-Acetyl-6-{3-(3,5-dichlorobenzyloxy)phenyl}-3-isopropyl-2-oxo-1,2,3,4-tetrahydropyrazin-1-yl]methylcarbonylamino-2-oxo-4-phenyl-1,1,1-trifluorobutane (Compound No. 4-47)

$[\alpha]_D^{20}$ −65.7° (c=0.51, methanol)

IR(Film,cm⁻¹)3304,1672,1571,1433,1389,1286

(2RS)-2-{(3RS)-4-Benzoyl-3-isopropyl-2-oxo-6-phenyl-1,2,3,4-tetrahydropyrazin-1-yl}methylcarbonylamino-4,4,5,5,6,6,6-heptafluoro-3-oxo-1-phenylhexane (Compound No. 4-48)

IR(Film,cm⁻¹)3294,3063,3029,2966,1689,1668,1636,1577,1538,1495,1448,1388

Example 5

(1RS,2S)-2-{(3RS)-4-Acetyl-3-isopropyl-2-oxo-6-phenyl-1,2,3,4-tetrahydropyrazin-1-yl}methylcarbonylamino-3-phenyl-1-(1,3-thiazol-2-yl)-1-propanol (Compound No. 5-1)

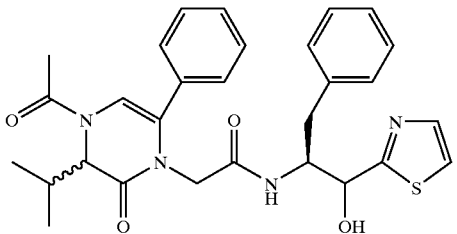

N-Methylmorpholine (66.4 μl) is added to a solution of {(3RS)-4-acetyl-3-isopropyl-2-oxo-6-phenyl-1,2,3,4-tetrahydropyrazin-1-yl}-acetic acid (162 mg, Reference compound No. 51-1) in tetrahydrofuran (2.5 ml). The mixture is cooled to −10° C., isobutyl chloroformate (65.4 μl) is added to the mixture, and the whole is stirred for 15 minutes. A mixed solution of (1RS,2S)-2-amino-3-phenyl-1-(1,3-thiazol-2-yl)-1-propanol hydrochloride (150 mg, Reference compound No. 10-2) and N-methylmorpholine (132.6 μl) in tetrahydrofuran (2.5 ml) and dimethyl sulfoxide (1 ml) is added thereto, and the whole is stirred overnight. Water is added to the reaction mixture, and the whole is extracted with ethyl acetate. The extract is washed with an aqueous sodium hydrogencarbonate solution, water and saturated brine successively and dried over magnesium sulfate. The extract is concentrated under reduced pressure, and the resulting residue is purified by column chromatography to give the titled compound (162.9 mg).

The following compounds are obtained by a method similar to Example 5.

(1RS,2S)-2-{(3RS)-4-Acetyl-3-isopropyl-2-oxo-6-phenyl-1,2,3,4-tetrahydropyrazin-1-yl}methylcarbonyl-amino-1-(1,3-benzothiazol-2-yl)-3-phenyl-1-propanol (Compound No. 5-2)

(1RS,2S)-2-{(3RS)-4-Acetyl-3-isopropyl-2-oxo-6-phenyl-1,2,3,4-tetrahydropyrazin-1-yl}methylcarbonyl-amino-1-(4,5-dihydro-1,3-oxazol-2-yl)-3-phenyl-1-propanol (Compound No. 5-3)

IR(Film,cm⁻¹)3307,3061,2965,1749,1674,1540,1446

(1RS,2S)-2-{(3RS)-4-Acetyl-3-isopropyl-2-oxo-6-phenyl-1,2,3,4-tetrahydropyrazin-1-yl}methylcarbonyl-amino-1-(4,5-dihydro-1,3-thiazol-2-yl)-3-phenyl-1-propanol (Compound No. 5-4)

IR(Film,cm⁻¹)3307,3011,2965,1681,1532,1446

(1RS,2S)-1-(4,5-Dihydro-1,3-oxazol-2-yl)-2-{(3RS)-3-isopropyl-4-methoxyacetyl-2-oxo-6-phenyl-1,2,3,4-tetrahydropyrazin-1-yl}-methylcarbonylamino-3-phenyl-1-propanol (Compound No. 5-5)

IR(KBr,cm⁻¹)3324,3062,2964,1746,1678,1534,1496,1447

(1RS,2S)-1-(1-Aza-3-oxaspiro[4,4]non-1-en-2-yl)-2-{(3RS)-4-benzoyl-3-isopropyl-2-oxo-6-phenyl-1,2,3,4-tetrahydropyrazin-1-yl}-methylcarbonylamino-3-phenyl-1-propanol (Compound No. 5-6)

IR(Film,cm⁻¹)3307,3011,2965,1681,1532,1446

(1RS,2S)-1-(1-Aza-3-oxaspiro[4,4]non-1-en-2-yl)-2-{(3RS)-3-isopropyl-4-methoxyacetyl-2-oxo-6-phenyl-1,2,3,4-tetrahydropyrazin-1-yl}-methylcarbonylamino-3-phenyl-1-propanol (Compound No. 5-7)

IR(Film,cm⁻¹)3326,3062,3010,2963,2874,1682,1526,1447 (

1RS,2S)-1-(4,4-Dimethyl-3,4-dihydro-1,3-oxazol-2-yl)-3-{(3RS)-3-isopropyl-4-methoxyacetyl-2-oxo-6-phenyl-1,2,3,4-tetrahydropyrazin-1-yl}-methylcarbonylamino-3-phenyl-1-propanol (Compound No. 5-8)

IR(Film,cm⁻¹)3323,3062,2966,2932,1681,1540,1450

(1RS,2S)-2-{(3RS)-4-Benzenesulfonyl-3-isopropyl-2-oxo-6-phenyl-1,2,3,4-tetrahydropyrazin-1-yl}methylcarbonylamino-1-(4,4-dimethyl-3,4-dihydro-1,3-oxazol-2-yl)-3-phenyl-1-propanol (Compound No. 5-9)

IR(Film,cm⁻¹)3368,3063,3027,2967,2933,2874,1682,1538,1496,1447

(1RS,2S)-1-(4,4-Dimethyl-3,4-dihydro-1,3-oxazol-2-yl)-2-{(3RS)-3-isopropyl-2-oxo-6-phenyl-4-pivaloyl-1,2,3,4-tetrahydropyrazin-1-yl}-methylcarbonylamino-3-phenyl-1-propanol (Compound No. 5-10)

IR(Film,cm⁺¹)3325,3062,2968,2933,2874,1665,1540,1496,1446

(1RS,2S)-2-{(3RS)-4-Acetyl-3-isopropyl-2-oxo-6-phenyl-1,2,3,4-tetrahydropyrazin-1-yl}methylcarbonyl-amino-1-(5,5-dimethyl-4,5-dihydro-1,3-thiazol-2-yl)-3-phenyl-1-propanol (Compound No. 5-11)

IR(Film,cm⁻¹)3324,3011,2965,2930,1682,1650,1520,1446

(1RS,2S)-1-(5,5-Dimethyl-4,5-dihydro-1,3-thiazol-2-yl)-2-{(3R)-3-isopropyl-2-oxo-6-phenyl-4-(2-pyridylcarbonyl)-1,2,3,4-tetrahydropyrazin-1-yl}methylcarbonyl-amino-3-phenyl-1-propanol (Compound-No. 5-12)

IR(Film,cm⁻¹)3326,3010,2964,2928,1680,1585,1568,1529,1439

(1RS,2S)-1-(5,5-Dimethyl-4,5-dihydro-1,3-thiazol-2-yl)-2-{(3RS)-3-isopropyl-2-oxo-6-phenyl-4-(3-pyridylcarbonyl)-1,2,3,4-tetrahydropyrazin-1-yl}methylcarbonylamino-3-phenyl-1-propanol (Compound No. 5-13)

IR(Film ,cm⁻¹)3330,3012,2964,2930,1682,1589,1520,1496,1446

Isopropyl (2RS,3S)-2-hydroxy-3-{(2RS)-2-isopropyl-3-oxo-3,4-dihydro-2H-1,4-thiazin-4-yl}methylcarbonyl-amino-4-phenylbutyrate (Compound No. 5-14)

IR(Film,cm⁻¹)3325,1732,1667,1537,1495,1387,1265

Isopropyl (2RS,3S)-3-{(2RS)-5-ethyl-2-isopropyl-3-oxo-3,4-dihydro-2H-1,4-thiazin-4-yl}methylcarbonylamino-2-hydroxy-4-phenylbutyrate (Compound No. 5-15)

IR(Film,cm⁻¹)3393,1730,1666,1529,1454,1373,1263

Isopropyl (2RS,3S)-2-hydroxy-3-{(2RS)-2-isopropyl-3-oxo-5-phenyl-3,4-dihydro-2H-1,4-thiazin-4-yl}methylcarbonylamino-4-phenylbutyrate (Compound No. 5-16)

IR(Film,cm⁻¹)3388,1731,1672,1523

Isopropyl (2RS,3S)-3-{(2RS)-5-(4-fluorophenyl)-2-isopropyl-3-oxo-3,4-dihydro-2H-1,4-thiazin-4-yl}methylcarbonylamino-2-hydroxy-4-phenylbutyrate (Compound No. 5-17)

IR(Film,cm$^{-1}$)3369,1733,1668,1508,1225

Isopropyl (2RS,3S)-2-hydroxy-3-{(2RS)-2-isopropyl-5-(4-methoxyphenyl)-3-oxo-3,4-dihydro-2H-1,4-thiazin-4-yl}methylcarbonylamino-4-phenylbutyrate (Compound No. 5-18)

IR(Film,cm$^{-1}$)3391,1731,1667,1511,1249

Isopropyl (2RS,3S)-2-hydroxy-3-{(2RS)-2-methyl-3-oxo-3,4-dihydro-2H-1,4-thiazin-4-yl}methylcarbonylamino-4-phenylbutyrate (Compound No. 5-19)

IR(Film,cm$^{-1}$)3409,1731,1665,1539,1496

Isopropyl (2RS,3S)-3-{(2RS)-2-ethyl-3-oxo-3,4-dihydro-2H-1,4-thiazin-4-yl}methylcarbonylamino-2-hydroxy-4-phenylbutyrate (Compound No. 5-20)

IR(Film,cm$^{-1}$)3328,3064,1732,1667,1528,1496,1454

Isopropyl (2RS,3S)-2-hydroxy-3-{(2RS)-3-oxo-2-propyl-3,4-dihydro-2H-1,4-thiazin-4-yl}methylcarbonylamino-4-phenylbutyrate (Compound No. 5-21)

Isopropyl (2RS,3S)-2-hydroxy-3-{(2RS)-2-methoxy-3-oxo-3,4-dihydro-2H-1,4-thiazin-4-yl}methylcarbonylamino-4-phenylbutyrate (Compound No. 5-22)

Isopropyl (2RS,3S)-2-hydroxy-3-[(1RS)-1-{(2RS)-2-isopropyl-3-oxo-3,4-dihydro-2H-1,4-thiazin-4-yl}ethyl]carbonylamino-4-phenylbutyrate (Compound No. 5-23)

Isopropyl (2RS,3S)-2-hydroxy-3-[(1RS)-1-{(2RS)-2-isopropyl-3-oxo-3,4-dihydro-2H-1,4-thiazin-4-yl}propyl]carbonylamino-4-phenylbutyrate (Compound No. 5-24)

Isopropyl (2RS,3S)-3-[(1RS)-1-{(2RS)-2-isopropyl-3-oxo-3,4-dihydro-2H-1,4-thiazin-4-yl}-2-phenylethyl]carbonylamino-2-hydroxy-4-phenylbutyrate (Compound No. 5-25)

(2RS,3S)-3-{(3R)-4-Acetyl-3-isopropyl-2-oxo-6-phenyl-1,2,3,4-tetrahydropyrazin-1-yl}methylcarbonylamino-1-tert-butyldimethylsilyloxy-4-phenyl-2-butanol (Compound No. 5-26)

IR(Film,cm$^{-1}$)3325,2957,2929,1674,1388

(2RS,3S)-3-{(3RS)-4-Acetyl-3-isopropyl-2-oxo-6-phenyl-1,2,3,4-tetrahydropyrazin-1-yl}carbonylamino-2-hydroxy-4-phenylbutyramide (Compound No. 5-27)

N$^1$-Isopropyl-(2RS,3S)-3-{(3RS)-4-acetyl-3-isopropyl-2-oxo-6-phenyl-1,2,3,4-tetrahydropyrazin-1-yl}methylcarbonylamino-2-hydroxy-4-phenylbutyramide (Compound No. 5-28)

IR(Film,cm$^{-1}$)3307,1671,1532

N$^1$,N$^1$-Dimethyl-(2RS,3S)-3-{(3RS)-4-acetyl-3-isopropyl-2-oxo-6-phenyl-1,2,3,4-tetrahydropyrazin-1-yl}methylcarbonylamino-2-hydroxy-4-phenylbutyramide (Compound No. 5-29)

IR(Film,cm$^{-1}$)3326,2963,1676,1535,1387,1276

Example 6

(2S)-2-{(3RS)-4-Acetyl-3-isopropyl-2-oxo-6-phenyl-1,2,3,4-tetrahydropyrazin-1-yl}methylcarbonylamino-3-phenyl-1-propanol (Compound No. 6-1)

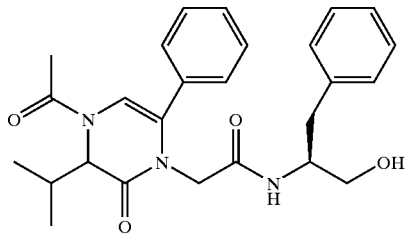

N-Methylmorpholine (525 μl), hydroxybenzotriazole (647 mg) and L-phenylalaninol (491 mg) are added to a solution of {(3RS)-4-acetyl-3-isopropyl-2-oxo-6-phenyl-1,2,3,4-tetrahydropyrazin-1-yl}acetic acid (1.01 g, Reference compound No. 51-1) in methylene chloride (25 ml). The mixture is cooled with ice, 1-(3-dimethylaminopropyl)-3-ethylcarbodiimide hydrochloride is added to the mixture, and the whole is stirred for three days. Ethyl acetate is added to the reaction mixture, and the whole is washed with a 0.1 N aqueous sodium hydroxide solution, saturated brine, 1 N hydrochloric acid and saturated brine successively. The organic layer is dried over anhydrous magnesium sulfate and concentrated under reduced pressure, and the resulting residue is purified by silica gel column chromatography to give the titled compound (1.37 g).

IR(Film,cm$^{-1}$)3318,2963,1670,1540

The following compounds are obtained by a method similar to Example 6.

(2S)-2-{(3RS)-4-Isobutyryl-3-isopropyl-2-oxo-6-phenyl-1,2,3,4-tetrahydropyrazin-1-yl}methylcarbonylamino-3-phenyl-1-propanol (Compound No. 6-2)

IR(Film,cm$^{-1}$)3325,1668,1540

(2S)-2-{(3R)-4-Isobutyryl-3-isopropyl-2-oxo-6-phenyl-1,2,3,4-tetrahydropyrazin-1-yl}methylcarbonylamino-3-phenyl-1-propanol (Compound No. 6-3)

(2S)-2-{(3RS)-4-Benzoyl-3-isopropyl-2-oxo-6-phenyl-1,2,3,4-tetrahydropyrazin-1-yl}methylcarbonylamino-3-phenyl-1-propanol (Compound No. 6-4)

IR(Film,cm$^{-1}$)3325,1667,1660

(2S)-2-{(3R)-3-Isopropyl-2-oxo-6-phenyl-4-(4-pyridylcarbonyl)-1,2,3,4-tetrahydropyrazin-1-yl}methylcarbonylamino-3-phenyl-1-propanol (Compound No. 6-5)

[α]$_D^{20}$ −121.6° (c=0.54, dimethyl sulfoxide)
IR(KBr,cm$^{-1}$)3288,1691,1674,1645,1601,1552

(2S)-2-{(3R)-3-Isopropyl-2-oxo-6-phenyl-4-(3-pyridylcarbonyl)-1,2,3,4-tetrahydropyrazin-1-yl}methylcarbonylamino-3-phenyl-1-propanol (Compound No. 6-6)

[α]$_D^{20}$ −121.7° (c=0.97, methanol)
IR(Film,cm$^{-1}$)3327,2962,2927,1669,1644,1446

(2S)-2-{(3RS)-3-Isopropyl-2-oxo-6-phenyl-4-(2-pyridylcarbonyl)-1,2,3,4-tetrahydropyrazin-1-yl}methylcarbonylamino-3-phenyl-1-propanol (Compound No. 6-7)

IR(Film,cm$^{-1}$)3327,1669

(2S)-2-{(3R)-3-Isopropyl-2-oxo-6-phenyl-4-(2-pyridylcarbonyl)-1,2,3,4-tetrahydropyrazin-1-yl}methylcarbonylamino-3-phenyl-1-propanol (Compound No. 6-8)

[α]$_D$$^{20}$ −185.0° (c=1.0, methanol)
IR(Filmn,cm$^{-1}$)3326,1670,1441

(2S)-2-{(3R)-4-Acetyl-3-isopropyl-2-oxo-6-phenyl-1,2,3,4-tetrahydropyrazin-1-yl}methylcarbonylamino-3-phenyl-1-propanol (Compound No. 6-9)

[α]$_D$$^{20}$ −97.1° (c=1.0, methanol)
IR(Film,cm$^{-1}$)3321,1670,1548,1391

Example 7

(2S)-2-{(3RS)-4-Acetyl-3-isopropyl-2-oxo-6-phenyl-1,2,3,4-tetrahydropyrazin 1-yl}methylcarbonylamino-3-phenylpropanal (Compound No. 7-1)

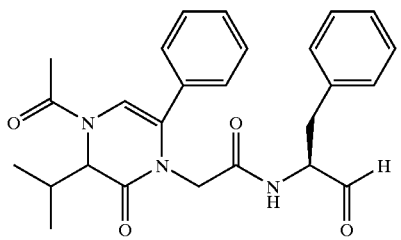

Triethylamine (2.60 ml) is added to a solution of (2S)-2-{(3RS)-4-acetyl-3-isopropyl-2-oxo-6-phenyl-1,2,3,4-tetrahydropyrazin-1-yl}-methylcarbonylamino-3-phenyl-1-propanol (1.37 g, Compound No. 6-1) in dimethyl sulfoxide (16 ml). A sulfur trioxide-pyridine complex (1.7 g) is added to the mixture, and the whole is stirred overnight. Water is added to the reaction mixture, and the whole is stirred for one hour and extracted with ethyl acetate. The extract is washed with a saturated aqueous ammonium chloride solution, water and saturated brine successively and dried over anhydrous magnesium sulfate. The extract is concentrated under reduced pressure, and the resulting residue is purified by silica gel column chromatography to give the titled compound (631 mg).

IR(Film,cm$^{-1}$)3306,3025,2964,1735,1673,1538

The following compounds are obtained by a method similar to Example 7.

(2S)-2-{(3RS)-4-Isobutyryl-3-isopropyl-2-oxo-6-phenyl-1,2,3,4-tetrahydropyrazin-1-yl}methylcarbonylamino-3-phenylpropanal (Compound No. 7-2)

(2S)-2-{(3R)-4-Isobutyryl-3-isopropyl-2-oxo-6-phenyl-1,2,3,4-tetrahydropyrazin-1-yl}methylcarbonylamino-3-phenylpropanal (Compound No. 7-3)

(2S)-2-{(3RS)-4-Benzoyl-3-isopropyl-2-oxo-6-phenyl-1,2,3,4-tetrahydropyrazin-1-yl}methylcarbonylamino-3-phenylpropanal (Compound No. 7-4)

IR(Film,cm$^{-1}$)3311,1734,1668

(2S)-2-{(3R)-3-Isopropyl-2-oxo-6-phenyl-4-(4-pyridylcarbonyl)-1,2,3,4-tetrahydropyrazin-1-yl}methylcarbonylamino-3-phenylpropanal (Compound No. 7-5)

(2S)-2-{(3R)-3-Isopropyl-2-oxo-6-phenyl-4-(3-pyridylcarbonyl)-1,2,3,4-tetrahydropyrazin-1-yl}methylcarbonylamino-3-phenylpropanal (Compound No. 7-6)

[α]$_D$$^{20}$ −106.5° (c=0.99, chloroform)
IR(Film,cm$^{-1}$)3326,2963,2925,1668,1643,1588,1539,1446

(2S)-2-{(3RS)-3-Isopropyl-2-oxo-6-phenyl-4-(2-pyridylcarbonyl)-1,2,3,4-tetrahydropyrazin-1-yl}methylcarbonylamino-3-phenylpropanal (Compound No. 7-7)

(2S)-2-{(3R)-3-Isopropyl-2-oxo-6-phenyl-4-(2-pyridylcarbonyl)-1,2,3,4-tetrahydropyrazin-1-yl}methylcarbonylamino-3-phenylpropanal (Compound No. 7-8)

[α]$_D$$^{20}$ −175.8° (c=1.0, chloroform)
IR(Film,cm$^{-1}$)1734,1682,1437

(2S)-2-{(3R)-4-Acetyl-3-isopropyl-2-oxo-6-phenyl-1,2,3,4-tetrahydropyrazin-1-yl}methylcarbonylamino-3-phenylpropanal (Compound No. 7-9)

[α]$_D$$^{20}$ −102.1° (c=0.93, methanol)
IR(Film,cm$^{-1}$)3308,1740

(3S)-3-{(3R)-4-Acetyl-3-isopropyl-2-oxo-6-phenyl-1,2,3,4-tetrahydropyrazin-1-yl}methylcarbonylamino-1-tert-butyldimethylsilyloxy-2-oxo-4-phenylbutane (Compound No. 7-10)

IR(Film,cm$^{-1}$)3307,2930,2856,1680,1528,1388

Example 8

(2RS,3S)-3-{(3RS)-4-Acetyl-3-isopropyl-2-oxo-6-phenyl-1,2,3,4-tetrahydropyrazin-1-yl}methylcarbonylamino-2-hydroxy-4-phenylbutanenitrile (Compound No. 8-1)

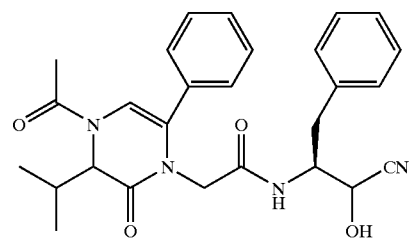

(2S)-2-{(3RS)-4-Acetyl-3-isopropyl-2-oxo-6-phenyl-1,2,3,4-tetrahydropyrazin-1-yl}methylcarbonylamino-3-phenylpropanal (630 mg, Compound No. 7-1) is suspended in water (6 ml). Sodium hydrogensulfite (160 mg), water (6 ml) and ethyl acetate (18 ml) are added to the suspension, and the mixture is stirred for 30 minutes. Potassium cyanide (105 mg) is added to the mixture, and the whole is stirred for one day. Water is added to the reaction mixture, and the whole is extracted with ethyl acetate. The extract is washed with water and saturated brine successively and dried over anhydrous magnesium sulfate. The extract is concentrated under reduced pressure, and the resulting residue is purified by silica gel column chromatography to give the titled compound (624 mg).

IR(Film,cm$^{-1}$)3305,1669,1540

The following compounds are obtained by a method similar to Example 8.

(2RS,3S)-2-Hydroxy-3-{(3RS)-4-isobutyryl-3-isopropyl-2-oxo-6-phenyl-1,2,3,4-tetrahydropyrazin-1-yl}methylcarbonylamino-4-phenylbutanenitrile (Compound No. 8-2)

IR(Film,cm$^{-1}$)3308,1670

(2RS,3S)-2-Hydroxy-3-{(3R)-4-isobutyryl-3-isopropyl-2-oxo-6-phenyl-1,2,3,4-tetrahydropyrazin-1-yl}methylcarbonylamino-4-phenylbutanenitrile (Compound No. 8-3)

IR(Film,cm$^{-1}$)3310,1666,1536,1446

(2RS,3S)-3-{(3RS)-4-Benzoyl-3-isopropyl-2-oxo-6-phenyl-1,2,3,4-tetrahydropyrazin-1-yl}methylcarbonylamino-2-hydroxy-4-phenylbutanenitrile (Compound No. 8-4)

IR(Film,cm$^{-1}$)3306,1666,1447

(2RS,3S)-2-Hydroxy-3-{(3R)-3-isopropyl-2-oxo-6-phenyl-4-(4-pyridylcarbonyl)-1,2,3,4-tetrahydropyrazin-1-yl}methylcarbonylamino-4-phenylbutanenitrile (Compound No. 8-5)

IR(Film,cm$^{-1}$)3310,1672,1601,1551,1495,1446

(2RS,3S)-2-Hydroxy-3-{(3R)-3-isopropyl-2-oxo-6-phenyl-4-(3-pyridylcarbonyl)-1,2,3,4-tetrahydropyrazin-1-yl}methylcarbonylamino-4-phenylbutanenitrile (Compound No. 8-6)

IR(Film,cm$^{-1}$)3356,2956,1662,1648,1540,1450,1426

(2RS,3S)-2-Hydroxy-3-{(3RS)-3-isopropyl-2-oxo-6-phenyl-4-(2-pyridylcarbonyl)-1,2,3,4-tetrahydropyrazin-1-yl}methylcarbonylamino-4-phenylbutanenitrile (Compound No. 8-7)

IR(Film,cm$^{-1}$)3306,1672

(2RS,3S)-2-Hydroxy-3-{(3R)-3-isopropyl-2-oxo-6-phenyl-4-(2-pyridylcarbonyl)-1,2,3,4-tetrahydropyrazin-1-yl}methylcarbonylamino-4-phenylbutanenitrile (Compound No. 8-8)

IR(Film,cm$^{-1}$)3314,1672,1643

Example 9

(1RS,2S)-2-{(3RS)-4-Acetyl-3-isopropyl-2-oxo-6-phenyl-1,2,3,4-tetrahydropyrazin-1-yl}methylcarbonylanmino-1-(4,4-dimethyl-4,5-dihydro-1,3-oxazol-2-yl)-3-phenyl-1-propanol (Compound No. 9-1)

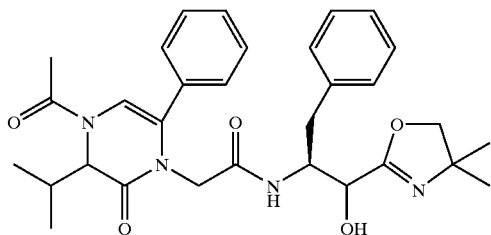

Acetyl chloride (1.1ml) is added dropwise to a solution of ethanol (0.95 ml) in chloroform (2ml) under ice cooling. Then, to the mixture is added a solution of (2RS,3S)-3-{(3RS)-4-acetyl-3-isopropyl-2-oxo-6-phenyl-1,2,3,4-tetrahydropyrazin-1-yl}methylcarbonylamino-2-hydroxy-4-phenylbutanenitrile (250 mg, Compound No. 8-1) in chloroform (3 ml), and the whole is stirred for one hour. The reaction mixture is concentrated under reduced pressure, ethanol (4 ml) and 2-amino-2-methyl-1-propanol (75 μl) are added to the resulting residue, and the whole is refluxed for one day. The reaction mixture is allowed to stand at room temperature, ethyl acetate is added to the reaction mixture, and the whole is washed with saturated brine. The organic layer is dried over anhydrous magnesium sulfate and concentrated under reduced pressure, and the resulting residue is purified by silica gel column chromatography to give the titled compound (113 mg).

IR(Film,cm$^{-1}$)3307,1674

The following compounds are obtained by a method similar to Example 9.

(1RS,2S)-1-(4,4-Dimethyl-4,5-dihydro-1,3-oxazol-2-yl)-2-{(3RS)-4-isobutyryl-3-isopropyl-2-oxo-6-phenyl-1,2,3,4-tetrahydropyrazin-1-yl}-methylcarbonylamino-3-phenyl-1-propanol (Compound No. 9-2)

IR(Film,cm$^{-1}$)3319,1674,1536

(1RS,2S)-1-(4,4-Dimethyl-4,5-dihydro-1,3-oxazol-2-yl)-2-{(3R)-4-isobutyryl-3-isopropyl-2-oxo-6-phenyl-1,2,3,4-tetrahydropyrazin-1-yl}-methylcarbonylamino-3-phenyl-1-propanol (Compound No. 9-3)

IR(Film,cm$^{-1}$)3318,1674,1536

(1RS,2S)-1-(5,5-Dimethyl-4,5-dihydro-1,3-thiazol-2-yl)-2-{(3RS)-4-isobutyryl-3-isopropyl-2-oxo-6-phenyl-1,2,3,4-tetrahydropyrazin-1-yl}-methylcarbonylamino-3-phenyl-1-propanol (Compound No. 9-4)

IR(Film,cm$^{-1}$)3324,2968,2932,1682,1446

(1RS,2S)-1-(5,5-Dimethyl-4,5-dihydro-1,3-thiazol-2-yl)-2-{(3R)-4-isobutyryl-3-isopropyl-2-oxo-6-phenyl-1,2,3,4-tetrahydropyrazin-1-yl}-methylcarbonylamino-3-phenyl-1-propanol (Compound No. 9-5)

IR(Film,cm$^{-1}$)3324,2967,1682,1522,1446

(1RS,2S)-1-(1-Aza-3-oxaspiro[4,4]non-1-en-2-yl)-2-{(3RS)-4-isobutyryl-3-isopropyl-2-oxo-6-phenyl-1,2,3,4-tetrahydropyrazin-1-yl}-methylcarbonylamino-3-phenyl-1-propanol (Compound No. 9-6)

IR(Film,cm$^{-1}$)3325,1671,1538

(1RS,2S)-2-{(3RS)-4-Benzoyl-3-isopropyl-2-oxo-6-phenyl-1,2,3,4-tetrahydropyrazin-1-yl}methylcarbonyl-amino-1-(4,4-dimethyl-4,5-dihydro-1,3-oxazol-2-yl)-3-phenyl-1-propanol (Compound No. 9-7)

IR(Film,cm$^{-1}$)3309,1668

(1RS,2S)-2-{(3RS)-4-Benzoyl-3-isopropyl-2-oxo-6-phenyl-1,2,3,4-tetrahydropyrazin-1-yl}methylcarbonyl-amino-1-(5,5-dimethyl-4,5-dihydro-1,3-thiazol-2-yl)-3-phenyl-1-propanol (Compound No. 9-8)

(1RS,2S)-1-(4,4-Dimethyl-4,5-dihydro-1,3-oxazol-2-yl)-2-{(3R)-3-isopropyl-2-oxo-6-phenyl-4-(4-pyridyl-carbonyl)-1,2,3,4-tetrahydropyrazin-1-yl}methylcarbonyl-amino-3-phenyl-1-propanol (Compound No. 9-9)

IR(Film,cm$^{-1}$)3291,1673,1599,1551,1446

(1RS,2S)-1-(5,5-Dimethyl-4,5-dihydro-1,3-thiazol-2-yl)-2-{(3R)-3-isopropyl-2-oxo-6-phenyl-4-(4-pyridyl-carbonyl)-1,2,3,4-tetrahydropyrazin-1-yl}methyl-carbonylamino-3-phenyl-1-propanol (Compound No. 9-10)

IR(Film,cm$^{-1}$)3324,1682,1650,1552

(1RS,2S)-1-(4,4-Dimethyl-4,5-dihydro-1,3-oxazol-2-yl)-2-{(3R)-3-isopropyl-2-oxo-6-phenyl-4-(3-pyridyl-carbonyl)-1,2,3,4-tetrahydropyrazin-1-yl}methyl-carbonylamino-3-phenyl-1-propanol (Compound No. 9-11)

IR(Film,cm$^{-1}$)3324,2966,1673,1644

(1RS,2S)-1-(4,4-Dimethyl-4,5-dihydro-1,3-oxazol-2-yl)-2-{(3RS)-3-isopropyl-2-oxo-6-phenyl-4-(2-pyridylcarbonyl)-1,2,3,4-tetrahydropyrazin-1-yl}methylcarbonylamino-3-phenyl-1-propanol (Compound No. 9-12)

IR(Film,cm$^{-1}$)3321,1672

(1RS,2S)-1-(4,4-Dimethyl-4,5-dihydro-1,3-oxazol-2-yl)-2-{(3R)-3-isopropyl-2-oxo-6-phenyl-4-(2-pyridyl-carbonyl)-1,2,3,4-tetrahydropyrazin-1-yl}methyl-carbonylamino-3-phenyl-1-propanol (Compound No. 9-13)

IR(Film,cm$^{-1}$)3324,1673,1539,1437

Example 10

(2S)-2-{(3RS)-4-Acetyl-3-isopropyl-2-oxo-6-phenyl-1,2,3,4-tetrahydropyrazin-1-yl}methylcarbonylamino-1-(4,4-dimethyl-4,5-dihydro-1,3-oxazol-2-yl)-1-oxo-3-phenylpropane (Compound No. 10-1)

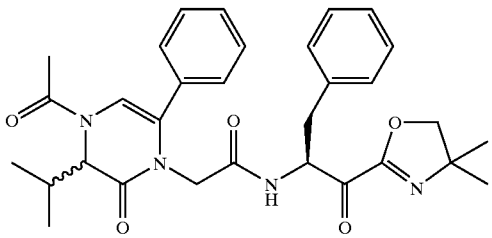

Dess-Martin oxidizing reagent (293 mg) and tert-butanol (650 μl) are added to a solution of (1RS,2S)-2-{(3RS)-4-acetyl-3-isopropyl-2-oxo-6-phenyl-1,2,3,4-tetrahydropyrazin-1-yl}methylcarbonylamino-1-(4,4-dimethyl-4,5-dihydro-1,3-oxazol-2-yl)-3-phenyl-1-propanol (93.3 mg, Compound No. 9-13) in methylene chloride (2.5 ml), and the mixture is stirred for one day. A saturated aqueous sodium hydrogencarbonate solution (6 ml) and an aqueous sodium thiosulfate solution (6 ml) are added to the reaction mixture, and the whole is stirred and then extracted with ethyl acetate. The extract is washed with an aqueous sodium thiosulfate solution, a saturated aqueous sodium hydrogencarbonate solution and saturated brine successively and dried over anhydrous magnesium sulfate. The extract is concentrated under reduced pressure, and the resulting residue is purified by silica gel column chromatography to give the titled compound (43.8 mg).

IR(Film,cm$^{-1}$)3306,1682,1520

The following compounds are obtained by a method similar to Example 10.

(2S)-1-(4,4-Dimethyl-4,5-dihydro-1,3-oxazol-2-yl)-2-{(3RS)-4-isobutyryl-3-isopropyl-2-oxo-6-phenyl-1,2,3,4-tetrahydropyrazin-1-yl}-methylcarbonylamino-1-oxo-3-phenylpropane (Compound No. 10-2)

IR(Film,cm$^{-1}$)3324,1700,1678

(2S)-1-(4,4-Dimethyl-4,5-dihydro-1,3-oxazol-2-yl)-2-{(3R)-4-isobutyryl-3-isopropyl-2-oxo-6-phenyl-1,2,3,4-tetrahydropyrazin-1-yl}-methylcarbonylamino-1-oxo-3-phenylpropane (Compound No. 10-3)

IR(Film,cm$^{-1}$)3323,1726,1682,1518

(2S)-1-(5,5-Dimethyl-4,5-dihydro-1,3-thiazol-2-yl)-2-{(3RS)-4-isobutyryl-3-isopropyl-2-oxo-6-phenyl-1,2,3,4-tetrahydropyrazin-1-yl}-methylcarbonylamino-1-oxo-3-phenylpropane (Compound No. 10-4)

IR(Film,cm$^{-1}$)2967,1681,1516,1446

(2S)-1-(5,5-Dimethyl-4,5-dihydro-1,3-thiazol-2-yl)-2-{(3R)-4-isobutyryl-3-isopropyl-2-oxo-6-phenyl-1,2,3,4-tetrahydropyrazin-1-yl}-methylcarbonylamino-1-oxo-3-phenylpropane (Compound No. 10-5)

$[\alpha]_D^{20}$ −80.8° (c=1.0, dimethyl sulfoxide)
IR(Film,cm$^{-1}$)3325,2967,1682,1646,1514,1446

(2S)-1-(1-Aza-3-oxaspiro[4,4]non-1-en-2-yl)-2-{(3RS)-4-isobutyryl-3-isopropyl-2-oxo-6-phenyl-1,2,3,4-tetrahydropyrazin-1-yl}methylcarbonylamino-1-oxo-3-phenylpropane (Compound No. 10-6)

IR(Film,cm$^{-1}$)3323,1678

(2S)-2-{(3RS)-4-Benzoyl-3-isopropyl-2-oxo-6-phenyl-1,2,3,4-tetrahydropyrazin-1-yl}methylcarbonylamino-1-(4,4-dimethyl-4,5-dihydro-1,3-oxazol-2-yl)-1-oxo-3-phenylpropane (Compound No. 10-7)

IR(Film,cm$^{-1}$)3320,1727,1684,1578

(2S)-2-{(3RS)-4-Benzoyl-3-isopropyl-2-oxo-6-phenyl-1,2,3,4-tetrahydropyrazin-1-yl}methylcarbonylamino-1-(5,5-dimethyl-4,5-dihydro-1,3-thiazol-2-yl)-2-oxo-3-phenylpropane (Compound No. 10-8)

(2S)-1-(4,4-Dimethyl-4,5-dihydro-1,3-oxazol-2-yl)-2-{(3R)-3-isopropyl-2-oxo-6-phenyl-4-(4-pyridylcarbonyl)-1,2,3,4-tetrahydropyrazin-1-yl}methylcarbonylamino-1-oxo-3-phenylpropane (Compound No. 10-9)

(2S)-1-(5,5-Dimethyl-4,5-dihydro-1,3-thiazol-2-yl)-2-{(3R)-3-isopropyl-2-oxo-6-phenyl-4-(4-pyridylcarbonyl)-1,2,3,4-tetrahydropyrazin-1-yl}methylcarbonylamino-1-oxo-3-phenylpropane (Compound No. 10-10)

mp 100.0–125.0° C.
$[\alpha]_D^{20}$ −107.8° (c=1.0, methanol)
IR(KBr,cm$^{-1}$)3218,1684

(2S)-1-(4,4-Dimethyl-4,5-dihydro-1,3-oxazol-2-yl)-2-{(3R)-3-isopropyl-2-oxo-6-phenyl-4-(3-pyridylcarbonyl)-1,2,3,4-tetrahydropyrazin-1-yl}methylcarbonylamino-1-oxo-3-phenylpropane (Compound No. 10-11)

$[\alpha]_D^{20}$ −104.9° (c=1.0, dimethyl sulfoxide)
IR(Film,cm$^{-1}$)3325,3023,2969,1723,1678,1642,1589,1517,1447

(2S)-1-(4,4-Dimethyl-4,5-dihydro-1,3-oxazol-2-yl)-2-{(3RS)-3-isopropyl-2-oxo-6-phenyl-4-(2-pyridylcarbonyl)-1,2,3,4-tetrahydropyrazin-1-yl}methylcarbonylamino-1-oxo-3-phenylpropane (Compound No. 10-12)

IR(Film,cm$^{-1}$)3324,1736,1681,1514

(2S)-1-(4,4-Dimethyl-4,5-dihydro-1,3-oxazol-2-yl)-2-{(3R)-3-isopropyl-2-oxo-6-phenyl-4-(2-pyridylcarbonyl)-1,2,3,4-tetrahydropyrazin-1-yl}methylcarbonylamino-1-oxo-3-phenylpropane (Compound No. 10-13)

$[\alpha]_D^{20}$ −126.6° (c=0.98, dimethyl sulfoxide)
IR(Film,cm$^{-1}$)3324,3061,3014,2970,2934,1737,1682,1641,1586,1568,1514,1468

(2S)-{(3RS)-4-Acetyl-3-isopropyl-2-oxo-6-phenyl-1,2,3,4-tetrahydropyrazin-1-yl}-1-oxo-3-phenyl-1-(1H-1,2,3,4-tetrazol-5-yl)-propane (Compound No. 10-14)

IR(Film,cm$^{-1}$)3204,1673,1529,1391,756

Example 11

(3S)-3-{(3R)-4-Acetyl-3-isopropyl-2-oxo-6-phenyl-1,2,3,4-tetrahydropyrazin-1-yl}methylcarbonylamino-2-oxo-4-phenylbutyric acid (Compound No. 11-1)

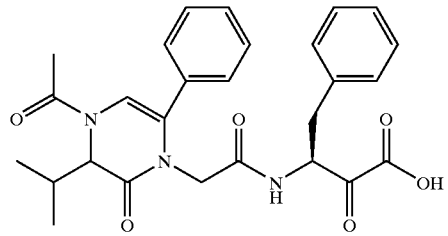

Water (0.45 ml) and a 1N aqueous lithium hydroxide solution (55 μl) are added to a solution of isopropyl (3S)-3-{(3R)-4-acetyl-3-isopropyl-2-oxo-6-phenyl-1,2,3,4-tetrahydropyrazin-1-yl}methylcarbonylamino-2-oxo-4-phenylbutyrate (24.5 mg, Compound No. 2-2) in methanol (0.5 ml), and the mixture is stirred for one hour. The reaction mixture is concentrated under reduced pressure, and 1 N hydrochloric acid is added to the concentrate to acidify the system. The whole is extracted with ethyl acetate, and the extract is washed with water and a saturated aqueous sodium hydrogencarbonate solution successively and dried over magnesium sulfate. The extract is concentrated under reduced pressure, and the resulting residue is purified by silica gel column chromatography to give the titled compound (21.8 mg).

IR(KBr,cm$^{-1}$)3305,2965,1671,1534,1497,1389

Example 12

(3S)-3-{(3R)-4-Acetyl-3-isopropyl-2-oxo-6-phenyl-1,2,3,4-tetrahydropyrazin-1-yl}methylcarbonylamino-2-oxo-4-phenyl-1-butanol (Compound No. 12-1)

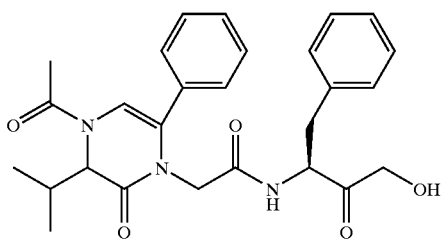

A 1.0 M tetrabutylammonium fluoride/tetrahydrofuran solution (0.5 ml) is added to a solution of (3S)-3-{(3R)-4-acetyl-3-isopropyl-2-oxo-6-phenyl-1,2,3,4-tetrahydropyrazin-1-yl}methylcarbonylamino-1-tert-butyldimethylsilyloxy-2-oxo-4-phenylbutane (130 mg, Compound No. 7-10) in tetrahydrofuran (0.5 ml), and the mixture is stirred for 2.5 hours. The reaction mixture is concentrated under reduced pressure, and the resulting residue is purified by silica gel column chromatography to give the titled compound (25.2 mg).

IR(Film,cm$^{-1}$)3849,3305,2963,1674,1529,1388

Example 13

(2S)-2-{(3RS)-4-Acetyl-3-isopropyl-2-oxo-6-phenyl-1,2,3,4-tetrahydropyrazin-1-yl}methylcarbonylamino-3-phenylpropionic acid (Compound No. 13-1)

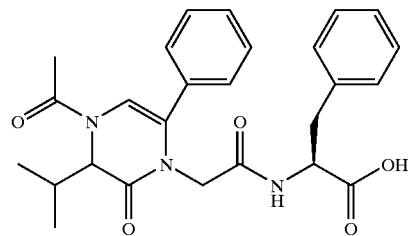

A 4 N aqueous sodium hydroxide solution (7.2 ml) is added to a solution of methyl (2S)-2-{(3RS)-4-acetyl-3-isopropyl-2-oxo-6-phenyl-1,2,3,4-tetrahydropyrazin-1-yl}methylcarbonylamino-3-phenylpropionate (4.60 g, Compound No. 1-48) in ethanol (30 ml), and the mixture is stirred for 4.5 hours. The reaction mixture is washed with ether, then 2N hydrochloric acid is added to the reaction mixture to acidify the system, and the whole is extracted with ethyl acetate. The extract is washed with saturated brine and dried over anhydrous magnesium sulfate. The extract is concentrated under reduced pressure to give the titled compound (4.46 g).

IR(Film,cm$^{-1}$)3306,3016,1732 1679,1530,1446,1391

Example 14

4-Nitrophenyl (2S)-2-{(3RS)-4-acetyl-3-isopropyl-2-oxo-6-phenyl-1,2,3,4-tetrahycdropyrazin-1-yl}methylcarbonylamino-3-phenylpropionate (Compound No. 14-1)

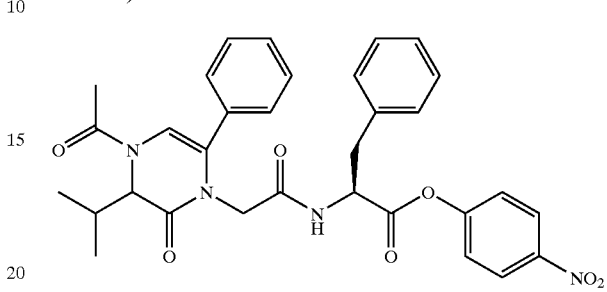

4-Nitrophenol (1.39 g) and dicyclohexylcarbodiimide (2 01 g) are added to a solution of (2S)-2-{(3RS)-4-acetyl-3-isopropyl-2-oxo-6-phenyl-1,2,3,4-tetrahydropyrazin-1-yl}methylcarbonylamino-3-phenylpropionic acid (4.30 g, Compound No. 13-1) in ethyl acetate (100 ml), and the mixture is stirred overnight. The resulting impurity is filtered out, then the filtrate is concentrated under reduced pressure, and the resulting residue is purified by silica gel column chromatography to give the titled compound (4.52 g).

IR(Film,cm$^{-1}$)3303,3025,1769,1679,1592,1524,1491,1446,1390

Example 15

3-[(2S)-2-{(3RS)-4-Acetyl-3-isopropyl-2-oxo-6-phenyl-1,2,3,4-tetrahydropyrazin-1-yl}methylcarbonylamino-3-phenylpropanoyl]-1-methylhydantoin (Compound No. 15-1)

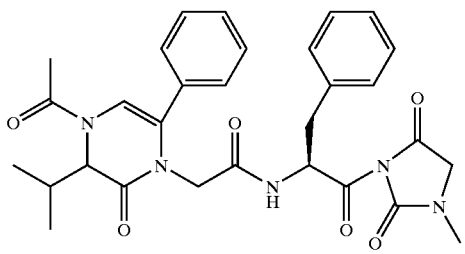

60% Sodium hydride (200 mg) is added to a solution of 1-methylhydantoin (571 mg) in anhydrous tetrahydrofuran (20 ml), and the mixture is stirred for 20 minutes. Then, 4-nitrophenyl (2S)-2-{(3RS)-4-acetyl-3-isopropyl-2-oxo-6-phenyl-1,2,3,4-tetrahydropyrazin-1-yl}methylcarbonyl-amino-3-phenylpropionate (1.17 g, Compound No. 14-1) is added to the mixture, and the whole is stirred for three days. A saturated aqueous ammonium chloride solution is added to the reaction mixture, and the whole is extracted with ethyl acetate. The extract is washed with a saturated aqueous sodium hydrogencarbonate solution and saturated brine successively and dried over anhydrous magnesium sulfate. The extract is concentrated under reduced pressure, and the resulting residue is purified by silica gel column chromatography to give the titled compound (116 mg).

IR(Film,cm$^{-1}$)3303,3016,2966,2935,1739,1526,1417,1391

Example 16

(2S)-2-{(3RS)-4-Acetyl-3-isopropyl-2-oxo-6-phenyl-1,2,3,4-tetrahydropyrazin-1-yl}methylcarbonylamino-1-(2,3-dihydrofuran-5-yl)-1-oxo-3-phenylpropane (Compound No. 16-1)

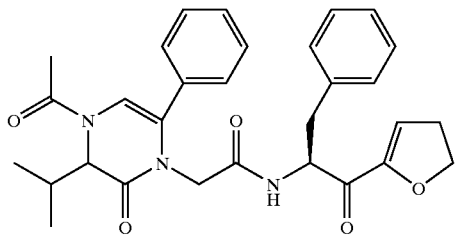

A solution of 2,3-dihydrofuran (80 μl) in anhydrous tetrahydrofuran (2 ml) is cooled to −78° C., a 1.55 N tert-butyllithium/pentane solution (660 g 1) is added thereto, and the mixture is stirred for one hour. The mixture is added to a solution of $N^1$-methoxy-$N^1$-methyl-(2S)-2-{(3RS)-4-acetyl-3-isopropyl-2-oxo-6-phenyl-1,2,3,4-tetrahydropyrazin-1-yl}methylcarbonylamino-3-phenylpropionamide (295 mg, Compound No. 1-51) in anhydrous tetrahydrofuran (3 ml) cooled at −78° C., and the whole is stirred for two hours. The temperature is raised to 0° C., and the reaction mixture is stirred for 30 minutes. A saturated aqueous ammonium chloride solution is added to the reaction mixture, and the whole is extracted with ethyl acetate. The extract is washed with saturated brine and dried over anhydrous magnesium sulfate. The extract is concentrated under reduced pressure, and the resulting residue is purified by silica gel column chromatography to give the titled compound (38.4 mg).

IR(Film,cm$^{-1}$)3307,1679,1388

Example 17

(3S)-3-{(3RS)-4-Acetyl-3-isopropyl-2-oxo-6-phenyl-1,2,3,4-tetrahydropyrazin-1-yl}methylcarbonylamino-2-oxo-4-phenylbutane (Compound No. 17-1)

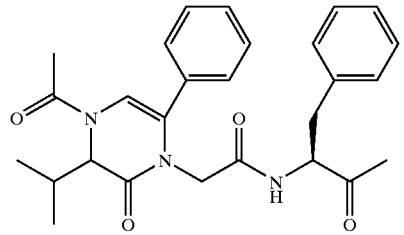

A solution of $N^1$-methoxy-$N^1$-methyl-(2S)-2-{(3RS)-4-acetyl-3-isopropyl-2-oxo-6-phenyl-1,2,3,4-tetrahydropyrazin-1-yl}-methylcarbonylamino-3-phenylpropionamide (122 mg, Compound No. 1-51) in anhydrous tetrahydrofuran (2 ml) is cooled to −78° C., a 1.0 M methyllithium/tetrahydrofuran/cumene solution (1.2 ml) is added thereto, and the mixture is stirred for 15 minutes. A saturated aqueous ammonium chloride solution is added to the reaction mixture, and the temperature is raised to 0° C. The whole is extracted with ethyl acetate, and the extract is washed with saturated brine and dried over anhydrous magnesium sulfate. The extract is concentrated under reduced pressure, and the resulting residue is purified by silica gel column chromatography to give the titled compound (53.8 mg).

IR(Film,cm$^{-1}$)3305,1700,1660

Example 18

(2RS,3S)-2-Acetoxy-3-{(3RS)-4-acetyl-3-isopropyl-2-oxo-6-phenyl-1,2,3,4-tetrahydropyrazin-1-yl}methylcarbonylamino-4-phenylbutanenitrile (Compound No. 18-1)

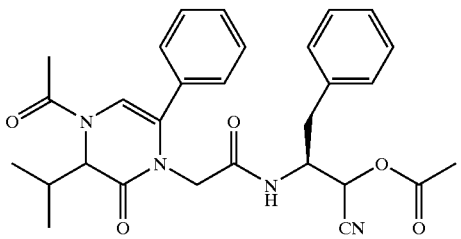

Pyridine (0.15 ml) is added to a solution of (2RS,3S)-3-{(3RS)-4-acetyl-3-isopropyl-2-oxo-6-phenyl-1,2,3,4-tetrahydropyrazin-1-yl}-methylcarbonylamino-2-hydroxy-4-phenylbutanenitrile (291 mg, Compound No. 8-1) in methylene chloride (3 ml). The mixture is cooled with ice, acetic anhydride (115 μl) and dimethylaminopyridine (catalytic amount) are added to the mixture, and the whole is stirred for six hours. Ethyl acetate is added to the reaction mixture, and the whole is washed with 1 N hydrochloric acid and saturated brine successively. The organic layer is concentrated under reduced pressure, and the resulting residue is purified by silica gel column chromatography to give the titled compound (317 mg).

IR(Film,cm$^{-1}$)3305,1758,1682,1538,1388,1320,1275,757

Example 19

(1RS,2S)-2-{(3RS)-4-Acetyl-3-isopropyl-2-oxo-6-phenyl-1,2,3,4-tetrahydropyrazin-1-yl}-3-phenyl-1-(1H-1,2,3,4-tetrazol-5-yl)-1-propanol (Compound No. 19-1)

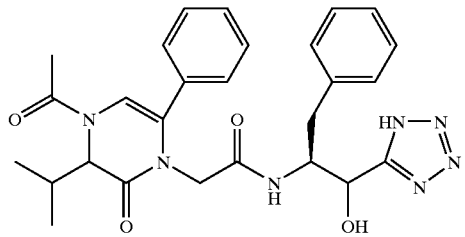

Sodium azide (75.3 mg) and aluminum chloride (386 mg) are added to a solution of (2RS,3S)-2-acetoxy-3-{(3RS)-4-acetyl-3-isopropyl-2-oxo-6-phenyl-1,2,3,4-tetrahydropyrazin-1-yl}methylcarbonylamino-4-phenylbutanenitrile (299 mg, Compound No. 18-1) in tetrahydrofuran (3.5 ml), and the mixture is stirred for two hours. The reaction mixture is warmed to 60° C. and stirred for three hours. The reaction mixture is cooled to room temperature, then water is added to the reaction mixture, and the whole is extracted with ethyl acetate. The extract is washed with saturated brine and dried over anhydrous magnesium sulfate. The extract is concentrated under reduced pressure, and the resulting residue is purified by silica gel column chromatography to give the titled compound (242 mg).

IR(Film,cm$^{-1}$)3292,1667,1529,1391,756

Example 20

(2S)-2-{(3RS)-3-Isopropyl-2-oxo-4-methoxyacetyl-6-phenyl-1,2,3,4-tetrahydropyrazin-1-yl}methylcarbonylamino-1-oxo-1-(piperazin-1-yl)-3-phenylpropane hydrochloride (Compound No. 20-1)

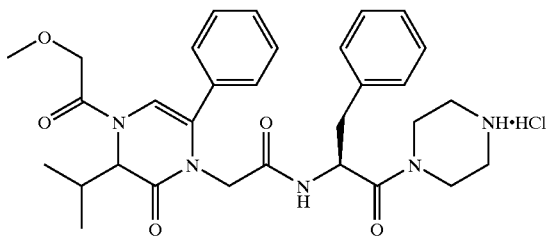

A 4 N hydrogen chloride/ethyl acetate solution (0.24 ml) is added to a solution of (2S)-1-(4-tert-butoxycarbonylpiperazin-1-yl)-2-{(3RS)-3-isopropyl-4-methoxyacetyl-2-oxo-6-phenyl-1,2,3,4-tetrahydropyrazin-1-yl}methylcarbonylamino-1-oxo-3-phenylpropane (190 mg, Compound No. 1-55) in ethyl acetate (3 ml), and the mixture is stirred for one hour. The reaction mixture is concentrated under reduced pressure to give the titled compound (146 mg).

mp 120° C.
IR(Film,cm$^{-1}$)3450,2963,1684,1652,1544,1496,1448,1389

Example 21

3-[(2R)-4-{(1S)-1-Benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]-1-methylpyridinium iodide (Compound No. 21-1)

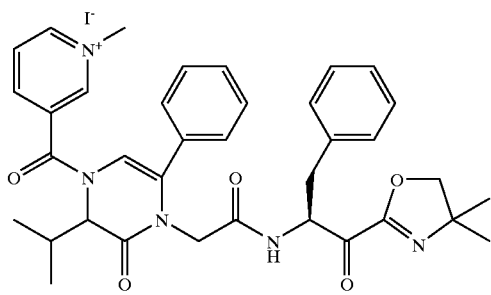

Methyl iodide (246 μl) is added to a solution of (2S)-1-(4,4-dimethyl-4,5-dihydro-1,3-oxazol-2-yl)-2-{(3R)-3-isopropyl-2-oxo-6-phenyl-4-(3-pyridylcarbonyl)-1,2,3,4-tetrahydropyrazin-1-yl}-methylcarbonylamino-1-oxo-3-phenylpropane (80 mg) in acetonitrile (2 ml), and the mixture is stirred overnight. The reaction mixture is concentrated under reduced pressure, and acetonitrile/diethyl ether is added to the resulting residue to precipitate crystals. The precipitated crystals are filtered off to give the titled compound (75 mg).

mp 160.0° C.
[α]$_D^{20}$ −106.4° (c=1.0, dimethyl sulfoxide)
IR(KBr,cm$^{-1}$)3421,3050,2967,1726,1676,1447

The following compounds are obtained by a method similar to Example 21.

3-[(2R)-4-{(1S)-1-Benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]-1-methoxycarbonylmethylpyridinium bromide (Compound No. 21-2)

mp 140.0° C.
[α]$_D^{20}$ −113.1° (c=1.0, dimethylsulfoxide)
IR(KBr,cm$^{-1}$)3350,3200,3030,2968,1755,1675,1542,1447

1-Benzyl-3-[(2R)-4-{(1S)-1-benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]pyridinium bromide (Compound No. 21-3)

mp135–150° C.
[α]$_D^{20}$ −110.1° (c=1.0, dimethyl sulfoxide)
IR(KBr,cm$^{-1}$)3400,3188,3031,2966,1725,1674,1455,1446

3-[(2R)-4-{(1S)-1-Benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]-1-carbamoylmethylpyridinium bromide (Compound No. 21-4)

mp 110.0° C.
[α]$_D^{20}$ −103.1° (c=0.98, dimethyl sulfoxide)
IR(KBr,cm$^{-1}$)3165,2968,1674

3-[(2R)-4-{(1S)-1-Benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]-1-[(E,E)-3,7,11-trimethyl-2,6,10-dodecathorin-1-yl]pyridinium bromide (Compound No. 21-5)

mp95–120° C.
[α]$_D^{20}$ −79.9° (c=0.99, dimethyl sulfoxide)
IR(KBr,cm$^{-1}$)3198,2965,1679,1518,1446

3-[(2RS)-4-{(1RS)-1-Benzyl-2-oxo-3,3,3-trifluoropropylcarbamoylmethyl}-2-isopropyl-3-oxo-5-phenyl-1,2,3,4-tetrahydro-1-pyrazinylcarbonyl]-1-methylpyridinium iodide (Compound No. 21-6)

IR(KBr,cm$^{-1}$)3436,1785,1677,1447

4-[(2RS)-4-{(1RS)-1-Benzyl-2-oxo-3,3,3-trifluoropropylcarbamoyl -methyl}-2-isopropyl-3-oxo-5-phenyl-1,2,3,4-tetrahydro-1-pyrazinylcarbonyl]-1-methylpyridinium iodide (Compound No. 21-7)

IR(KBr,cm$^{-1}$)3428,1786,1682

4-[(2R)-4-{(1S)-1-Benzyl-(4,4-dimethyl-4,5-dihydro-1,3-oxazol-2-yl)-2-oxopropylcarbamoylmethyl}-2-isopropyl-3-oxo-5-phenyl-1,2,3,4-tetrahydro-1-pyrazinylcarbonyl]-1-methyloxycarbonylmethylpyridinium bromide (Compound No. 21-8)

IR(KBr,cm$^{-1}$)3856,1753,1677

1-Benzyl-4-[(2R)-4-{(1S)-1-benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]pyridinium bromide (Compound No. 21-9)

IR(KBr,cm$^{-1}$)3369,1730,1677

4-[(2R)-4-{(1S)-1-Benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]-1-(3-methyl-2-butenyl)pyridinium bromide (Compound No. 21-10)

IR(KBr,cm$^{-1}$)3600–2000,1742,1677

4-[(2R)-4-{(1S)-1-Benzyl-2-(4,4-dimethyl-4,5-dihydro-1,3-oxazol-2-yl)-2-oxoethylcarbamoylmethyl}-2-isopropyl-3-oxo-5-phenyl-1,2,3,4-tetrahydro-1-pyrazinylcarbonyl]-1-

{(2E)-3,7-dimethyl-2,6-octadienyl}-pyridinium bromide (Compound No. 21-11)

IR(KBr,cm$^{-1}$)3560–2300,1752,1676,1529

4-{(2R)-4-[(1S)-1-Benzyl-2-(4,4-dimethyl-4,5-dihydro-1,3-oxazol-2-yl)-2-oxoethylcarbamoylmethyl]-2-isopropyl-3-oxo-5-phenyl-1,2,3,4-tetrahydro-1-pyrazinylcarbonyl}-1-(carbamoylmethyl)pyridinium iodide (Compound No. 21-12)

mp78.0–85.0° C.

IR(KBr,cm$^{-1}$)3305,1671

Formulation

General formulation examples of oral preparations and eyedrops using the present compounds are shown below.

| 1) Tablet | |
|---|---|
| Formulation 1 in | 100 mg |
| Present compound | 1 mg |
| Lactose | 66.4 mg |
| Cornstarch | 20 mg |
| Calcium carboxymethylcellulose | 6 mg |
| Hydroxypropylcellulose | 4 mg |
| Magnesium stearate | 0.6 mg |

Tablets according to the formulation as above are coated with 2 mg/tablet of a coating agent (this is a conventional coating agent such as hydroxypropylmethylcellulose, macrogol or silicone resin) to obtain desired coated tablets. (The same is applied to tablets mentioned below.) Desired tablets can be obtained by changing the amounts of the present compound and the additives appropriately.

| 2) Capsule | |
|---|---|
| Formulation 1 in | 150 mg |
| Present compound | 5 mg |
| Lactose | 145 mg |

Desired capsules can be obtained by changing the mixing ratio of the present compound to lactose appropriately.

| 3) Eyedrops | |
|---|---|
| Formulation 1 in | 10 ml |
| Present compound | 1 mg |
| Concentrated glycerin | 250 mg |
| Polysorbate 80 | 200 mg |
| Sodium dihydrogenphosphate dihydrate | 20 mg |
| 1N Sodium hydroxide | q.s. |
| 1N Hydrochloric acid | q.s. |
| Sterile purified water | q.s. |

Desired eyedrops can be obtained by changing the amounts of the present compound and the additives appropriately.

Pharmacological Test

1) Chymase Inhibitory Effect

Chymase (enzyme) causes angiotensin I (substrate) to liberate a dipeptide (His-Leu) by the enzyme reaction with the substrate. It was reported that an enzymatic activity of chymase can be measured by measuring fluorescence intensity of the resulting peptide (Biochem. Biophys. Res. Com., 149 (3) 1186 (1987)). Since drugs having chymase inhibitory activities suppress this liberation of the dipeptide, the chymase inhibitory activities of the drugs can be measured by measuring fluorescence intensity. In the present pharmacological test, chymase inhibitory effects of the present compounds were studied by using chymase extracted from a dog cardiac tissue (J. Biol. Chem., 265 (36), 22348 (1990)).

Experimental Method

[1. Preparation of Chymase Enzyme Solution]

1. A beagle is killed by drawing blood under Nembutal anesthesia, a heart is enucleated, and left ventricle is separated.
2. This left ventricle is finely minced, and the tissue weight is measured.
3. A 0.02 M Tris-HCl buffer (pH 7.4) is added to the tissue in an amount of 10 times by volume the tissue weight. The obtained mixture is homogenized at 8,000 rpm for 20 seconds and then centrifuged at 4° C. and 21,000 rpm for 30 minutes, and the resulting supernatant is discarded.
4. The same procedure as the above 3 is repeated twice for the residue. Then, a 0.02 M Tris-HCl buffer (pH 7.4) containing 1% Triton X-100 and 0.01 M potassium chloride is added to the residue in an amount of 10 times by volume the amount of the residue. The obtained mixture is homogenized at 8,000 rpm for 20 seconds, then incubated at 4° C. for one hour and centrifuged at 21,000 rpm for 30 minutes, and the supernatant is discarded.
5. A 0.02 M Tris-HCl buffer (pH 7.4) containing 1% Triton X-100 and 0.5 M potassium chloride is added to the residue in an amount of 10 times by volume the amount of the residue. The obtained mixture is homogenized at 8,000 rpm for 20 seconds, then incubated at 4° C. for one hour and centrifuged at 21,000 rpm for 30 minutes, and the supernatant is discarded.
6. A 0.02 M Tris-HCl buffer (pH 7.4) containing 1% Triton X-100 and 2.0 M potassium chloride is added to the residue in an amount of 10 times the amount of the residue. The obtained mixture is homogenized at 8,000 rpm for 20 seconds, then incubated at 4° C. for one hour and centrifuged at 21,000 rpm for 30 minutes. The obtained supernatant is used as a chymase enzyme solution.

[2. Preparation of Reaction Buffer]

Tris-HCl and disodium ethylenediaminetetraacetate are dissolved in water so that their concentrations are 92.3 mM and 12.0 mM respectively to prepare a reaction buffer adjusted to pH 8.

[3. Preparation of Substrate Solution]

Angiotensin I is dissolved in water to prepare a 1.54 mM substrate solution.

[4. Preparation of Test Compound Solution]

A test compound is dissolved in dimethyl sulfoxide to prepare $3.0\times10^{-3}$ M, $3.0\times10^{-4}$ M, $3.0\times10^{-5}$ M and $3.0\times10^{-6}$ M test compound solutions.

[5. Measurement of Chymase Enzymatic Activity]

1. The reaction buffer (32.5 μl), the substrate solution (75.0 μl), the chymase enzyme solution (37.5 μl) and the test compound solution (5 μl) are mixed.
2. The obtained mixture is incubated at 37° C. for one hour.
3. To the mixture is added 15% trichloroacetic acid (225 μl), and the whole is centrifuged at 4° C. and 14,000 rpm for five minutes.
4. The supernatant is taken out. A 1% orthophthalaldehyde/methanol solution (165 μl) is added to 300 μl of this supernatant, and the whole is stirred and allowed to stand at room temperature for 10 minutes.
5. 1.5 M Hydrochloric acid (300 μl) is added to the resulting mixture, and the whole is stirred and centrifuged at 4° C. and 14,000 rpm for two minutes.

6. The supernatant is taken out and irradiated with light having a wavelength of 340 nm, and fluorescence intensity is measured at a wavelength of 455 nm.

The blank of this test is defined as follows. The same procedures as in the above 1 to 6 are repeated provided that a 20 mM Ths-HCl buffer (pH 7.4, 37.5 µl) containing 1% Triton X-100 and 2.0 M potassium chloride is used instead of the chymase enzyme solution (37.5 µl), and dimethyl sulfoxide (5 µl) is used instead of the test compound solution (5 µl) in the above 1. The obtained absorbance is the blank value. The control of this test is defined as follows. The same procedures as in the above 1 to 6 are repeated provided that dimethyl sulfoxide (5 µl) is used instead of the test compound solution (5 µl) in the above 1. The obtained absorbance is the control value.

[6. Calculation of Chymase Inhibition Rate]

Chymase inhibition rates of the test compounds are calculated by the following equation from the measured fluorescence intensity.

Chymase inhibition rate (%)=[1-(Fluorescence intensity in using test compound solution-Blank fluorescence intensity)/(Control fluorescence intensity-Blank fluorescence intensity)]×100

[7. Results]

Concentrations required to inhibit a chymase enzymatic activity by 50% were calculated from the obtained chymase inhibition rates of the test compounds.

As examples of test results, Table 1 shows concentrations of the following test compounds (Compound Nos. 2-2 2, 2-31, 2-32, 2-34, 2-46, 2-47, 2-48, 2-63, 2-65, 4-1 and 10-7) required to inhibit the chymase enzymatic activity by 50%, i.e., $IC_{50}$.

TABLE 1

| Test compound | $IC_{50}$ (M) |
| --- | --- |
| Compound No. 2–22 | $0.20 \times 10^{-6}$ |
| Compound No. 2–31 | $0.21 \times 10^{-6}$ |
| Compound No. 2–32 | $0.36 \times 10^{-6}$ |
| Compound No. 2–34 | $0.25 \times 10^{-6}$ |
| Compound No. 2–46 | $3.80 \times 10^{-6}$ |
| Compound No. 2–47 | $0.50 \times 10^{-6}$ |
| Compound No. 2–48 | $1.20 \times 10^{-6}$ |
| Compound No. 2–63 | $0.32 \times 10^{-6}$ |
| Compound No. 2–65 | $0.28 \times 10^{-6}$ |
| Compound No. 4–1 | $1.50 \times 10^{-6}$ |
| Compound No. 10–7 | $0.37 \times 10^{-6}$ |

Table 1 shows that the present compounds exhibited excellent chymase inhibition effects.

From the above-mentioned results, the present compounds are expected to be useful as drugs, particularly to be effective in treating various diseases originating from chymase such as cardiac infarction, heart failure, blood-vessel restenosis after PTCA, hypertension, diabetes complication, allergic diseases and asthma.

Industrial Applicability

The present invention relates to novel 3-oxo-3,4-dihydro-2H-1,4-thiazine derivatives or 2-oxo-1,2,3,4-tetrahydropyrazine derivatives. These derivatives are expected to be effective in treating various diseases caused by chymase such as cardiac infarction, heart failure, blood-vessel restenosis after PTCA, hypertension, diabetes complication, allergic diseases and asthma.

What is claimed is:

1. A compound represented by the following formula [I] or a salt thereof,

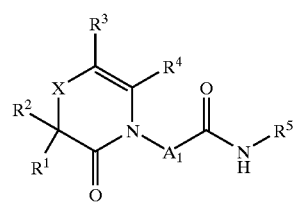

wherein

X is $R^6$—$(A_2)_n$—N, $R^1$ and $R^2$, being the same or different, are hydrogen, lower alkyl, cycloalkyl or aryl, $R^3$ and $R^4$, being the same or different, are hydrogen, lower alkyl, cycloalkyl, aryl or an aromatic heterocycle, $R^5$ is hydrogen, lower alkyl, cycloalkyl, aryl or —$A_3$—$A_4$—$R^7$, $R^6$ is hydrogen, lower alkyl, cycloalkyl, hydroxy, lower alkoxy, aryl, aryloxy or an aromatic heterocycle, $R^7$ is hydrogen, lower alkyl, hydroxy, lower alkoxy, aryl, aryloxy, amino, lower alkylamino, arylamino, an aromatic heterocycle or a nonaromatic heterocycle, n is 0 or 1, $A_1$ is lower alkylene, $A_2$ is carbonyl or sulfonyl, $A_3$ is lower alkylene, $A_4$ is carbonyl or oxalyl, each lower alkyl defined above is unsubstituted or substituted by halogen, hydroxy, lower alkoxy, aryl or aryloxy, each lower alkoxy defined above is unsubstituted or substituted by aryl, and each lower alkylene defined above is unsubstituted or substituted by aryl.

2. The compound or a salt thereof as claimed in claim 1, wherein $R^7$ is the nonaromatic heterocycle which is selected from the group consisting of pyrrolidine, pyrroline, tetrahydrofuran, dihydrofuran, tetrahydrothiophene, dihydrothiophene, imidazolidine, imidazoline, oxazolidine, oxazoline, 4,4-dimethyloxazoline, thiazolidine, thiazoline, 5,5-dimethylthiazoline, pyrazolidine, pyrazoline, piperidine, tetrahydropiperidine, dihydropiperidine, tetrahydropyran, dihydropyran, pyran, piperazine, morpholine, thiomorpholine, homopiperidine, homopiperazine and homombrpholine or $R^7$ is the aromatic heterocycle which is selected from the group consisting of pyrrole, furan, thiophene, imidazole, oxazole, thiazole, pyrazole, isoxazole, isothiazole, pyridine, pyrazine, pyrimidine, indole, isoindole, benzimidazole, benzoxazole, benzothiazole and quinoline.

3. The compound or a salt thereof as claimed in claim 1, wherein n is 1 in the formula [I].

4. The compound or a salt thereof as claimed in claim 3, wherein $R^6$ is lower alkyl, aryl or an aromatic heterocycle in the formula [I].

5. The compound or a salt thereof as claimed in claim 4, wherein $R^3$, $R^4$, $R^6$ or $R^7$ is the aromatic heterocycle which is selected from the group consisting of pyridine and thiophene.

6. The compound or a salt thereof as claimed in claim 1, wherein $R^5$ is —$A_3$—$A_4$—$R^7$, and $A_3$ is lower alkylene which is unsubstituted or substituted by phenyl in the formula [I].

7. The compound or a salt thereof as claimed in claim 6, wherein $R^7$ is lower alkyl, lower alkoxy, an aromatic heterocycle or a nonaromatic heterocycle in the formula [I].

8. The compound or a salt thereof as claimed in claim 7, wherein $R^7$ is the nonaromatic heterocycle which is selected from the group consisting of pyrrolidine, dihydrofuran, oxazolidine, 4,4-dimethyloxazoline, thiazoline, 5,5-dimethylthiazoline, piperidine, piperazine and morpholine or $R^7$ is the aromatic heterocycle which is selected from the group consisting of oxazole, thiazole and benzothiazole.

9. A pharmaceutical composition comprising a pharmaceutically effective amount of the compound or a salt thereof as claimed in claim 1 as an active ingredient in combination with a pharmaceutically acceptable carrier.

10. A compound represented by the following formula [II] or a salt thereof,

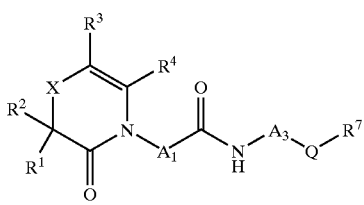

wherein

X is $R^6$—$(A_2)_n$—N, $R^1$ and $R^2$, being the same or different, are hydrogen, lower alkyl, cycloalkyl or aryl, $R^3$ and $R^4$, being the same or different, are hydrogen, lower alkyl, cycloalkyl, aryl or an aromatic heterocycle, $R^6$ is hydrogen, lower alkyl, cycloalkyl, hydroxy, lower alkoxy, aryl, aryloxy or an aromatic heterocycle, $R^7$ is hydrogen, lower alkyl, hydroxy, lower alkoxy, aryl, aryloxy, amino, lower alkylamino, arylamino, an aromatic heterocycle or a nonaromatic heterocycle, n is 0 or 1, $A_1$ is lower alkylene, $A_2$ is carbonyl or sulfonyl, $A_3$ is lower alkylene, Q is —CH(OH)CO— or —CH(OH)—, each lower alkyl defined above is unsubstituted or substituted by halogen, hydroxy, lower alkoxy, aryl or aryloxy, each lower alkoxy defined above is unsubstituted or substituted by aryl, and each lower alkylene defined above is unsubstituted or substituted by aryl.

11. A method of inhibiting chymase in a patient to treat a disease caused by chymase which is selected from the group consisting of cardiac infarction, heart failure, blood-vessel restenosis after PCTA, hypertension, diabetes complication, an allergic disease and asthma comprising administering to a patient in need thereof a pharmaceutically effective amount of the compound or a salt thereof according to claim 1, alone or in a combination with a pharmaceutically acceptable carrier.

12. The method as claimed in claim 11, wherein the administering to a patient is carried out orally.

13. The method as claimed in claim 11, wherein the administering to a patient is carried out parenterally.

14. The method as claimed in claim 11, wherein the administering to a patient is carried out by applying eye-drops.

15. The compound or a salt thereof as claimed in claim 1, wherein $R^3$ or $R^4$ is an aromatic heterocycle which is selected from the group consisting of pyrrole, furan, thiophene, imidazole, oxazole, thiazole, pyrazole, isoxazole, isothiazole, pyridine, pyrazine, pyrimidine, indole, isoindole, benzimidazole, benzoxazole, benzothiazole and quinoline.

16. The compound or a salt thereof a claimed in claim 1, wherein $R^6$ is an aromatic heterocycle which is selected from the group consisting of pyrrole, furan, thiophene, imidazole, oxazole, thiazole, pyrazole, isoxazole, isothiazole, pyridine, pyrazine, pyrimidine, indole, isoindole, benzimidazole, benzoxazole, benzothiazole and quinoline.

* * * * *